US012727810B2

(12) United States Patent
Nenadovic et al.

(10) Patent No.: US 12,727,810 B2
(45) **Date of Patent: *Sep. 8, 2026**

(54) SYSTEM, PROCESS, AND DEVICES FOR REAL-TIME BRAIN MONITORING

(71) Applicant: BRAINSVIEW INC., Mississauga (CA)

(72) Inventors: Vera Nenadovic, Mississauga (CA); Ramon Mariano Guevara Erra, Saint-Rémy-lès-Chevreuse (FR); Jason Boulet, Hamilton (CA)

(73) Assignee: BRAINSVIEW INC., Mississauga (CA)

( * ) Notice: Subject to any disclaimer, the term of this patent is extended or adjusted under 35 U.S.C. 154(b) by 778 days.

This patent is subject to a terminal disclaimer.

(21) Appl. No.: 17/572,532

(22) Filed: Jan. 10, 2022

(65) Prior Publication Data

US 2022/0160287 A1 May 26, 2022

Related U.S. Application Data

(63) Continuation-in-part of application No. 16/081,333, filed as application No. PCT/CA2017/050293 on Mar. 3, 2017, now Pat. No. 11,219,400, application No. 17/572,532 is a continuation-in-part of application No. 16/158,711, filed on Oct. 12, 2018, now Pat. No. 11,219,394, which is a continuation-in-part of application No. 16/081,333, filed as application No. PCT/CA2017/050293 on Mar. 3, 2017, now Pat. No. 11,219,400, application No. 17/572,532 is a continuation-in-part of application No. 16/198,153, filed on Nov. 21, 2018, now Pat. No. 11,317,874, which is a continuation-in-part of application No. 16/081,333, (Continued)

(51) Int. Cl.

| | |
|---|---|
| *A61B 5/384* | (2021.01) |
| *A61B 5/00* | (2006.01) |
| *A61B 5/16* | (2006.01) |
| *G16H 10/60* | (2018.01) |
| *G16H 20/70* | (2018.01) |
| *G16H 40/67* | (2018.01) |
| *G16H 50/30* | (2018.01) |

(52) U.S. Cl.

CPC ............. *A61B 5/384* (2021.01); *A61B 5/165* (2013.01); *A61B 5/4094* (2013.01); *A61B 5/7475* (2013.01); *G16H 10/60* (2018.01); *G16H 20/70* (2018.01); *G16H 40/67* (2018.01); *G16H 50/30* (2018.01)

(58) Field of Classification Search

None

See application file for complete search history.

(56) References Cited

U.S. PATENT DOCUMENTS

2008/0091118 A1* 4/2008 Georgopoulos ....... A61B 5/245 600/544

* cited by examiner

*Primary Examiner* — Jacqueline Cheng
*Assistant Examiner* — Jairo H Portillo
(74) *Attorney, Agent, or Firm* — Norton Rose Fulbright Canada LLP

(57) ABSTRACT

Systems, processes and devices for real-time brain monitoring to generate and control an interface of a display device with a visual representation of a Brain Value Index for entropy, a connectivity map and treatment guidance. Systems, processes and devices for real-time brain monitoring capture sensor data, process the data and dynamically update the interface in real-time.

20 Claims, 51 Drawing Sheets

Related U.S. Application Data filed as application No. PCT/CA2017/050293 on Mar. 3, 2017, now Pat. No. 11,219,400.

(60) Provisional application No. 62/590,058, filed on Nov. 22, 2017, provisional application No. 62/571,405, filed on Oct. 12, 2017, provisional application No. 62/365,506, filed on Jul. 22, 2016, provisional application No. 62/303,635, filed on Mar. 4, 2016.

2600

2700

2800

SYSTEM, PROCESS, AND DEVICES FOR REAL-TIME BRAIN MONITORING

CROSS REFERENCE TO RELATED APPLICATIONS

This application is a continuation-in-part of U.S. patent application Ser. No. 16/081,333 filed Aug. 30, 2018, which is a 371 of International Patent Application No. PCT/CA2017/050293 filed Mar. 3, 2017, which claims the benefit of U.S. Provisional Patent Application Nos. 62/303,635 and 62/365,506 filed Mar. 4, 2016 and Jul. 22, 2016 respectively, all of which are hereby incorporated by reference in their entirety.

This application is a continuation-in-part of U.S. patent application Ser. No. 16/158,711 filed Oct. 12, 2018, which is a continuation-in-part of U.S. patent application Ser. No. 16/081,333 filed Aug. 30, 2018, which is a 371 of International Patent Application No. PCT/CA2017/050293 filed Mar. 3, 2017, which claims the benefit of U.S. Provisional Patent Application Nos. 62/303,635 and 62/365,506 filed Mar. 4, 2016 and Jul. 22, 2016 respectively; U.S. patent application Ser. No. 16/158,711 filed Oct. 12, 2018 also claims the benefit of U.S. Provisional Patent Application No. 62/571,405 filed Oct. 12, 2017, all of which are hereby incorporated by reference in their entirety.

This application is a continuation-in-part of U.S. patent application Ser. No. 16/198,153 filed Nov. 21, 2018, which is a continuation-in-part of U.S. patent application Ser. No. 16/081,333 filed Aug. 30, 2018, which is a 371 of International Patent Application No. PCT/CA2017/050293 filed Mar. 3, 2017, which claims the benefit of U.S. Provisional Patent Application Nos. 62/303,635 and 62/365,506 filed Mar. 4, 2016 and Jul. 22, 2016 respectively; U.S. patent application Ser. No. 16/198,153 filed Nov. 21, 2018 also claims the benefit of U.S. Provisional Patent Application No. 62/590,058 filed Nov. 22, 2017, all of which are hereby incorporated by reference in their entirety.

FIELD

The improvements generally relate to the field of monitoring patients using sensors and computing devices.

INTRODUCTION

Consciousness can be considered an emergent property of brain matter. Patients with brain related disorders may have different levels of consciousness. Neurophysiologic recordings of brain activity may demonstrate fluctuating patterns of cellular interactions.

Anxiety disorders are commonly occurring mental health disorders accounting for 18% of mental illnesses. Anxiety can be described as an emergent property of brain electrical activity that recruits neuronal networks to create the physiological response associated with anxiety. Neurophysiologic recordings of brain activity may demonstrate fluctuating patterns of cellular interactions. Alcohol, which also alters neuronal networks, is commonly used to self-medicate and deal with the symptoms of anxiety.

Infantile spasms (IS), now known as epileptic spasms is a rare paediatric epilepsy disorder occurring in infancy and hypsarrhythmia is the characteristic, observed, high amplitude electroencephalographic (EEG) pattern. Epileptic spasms and hypsarrhythmia can be described as an emergent property of abnormal brain electrical activity wherein abnormal neuronal networks are created and result in physiological response associated with epileptic spasms, developmental delay or regression and the accompanying hypsarrhythmia EEG pattern. Neurophysiologic recordings of brain activity may demonstrate fluctuating patterns of cellular interactions. Adrenocorticotrophic hormone (ACTH) and vigabatrin, are medications which also alter neuronal networks, and commonly used to manage the symptoms of epileptic spasms and correct the hypsarrhythmia pattern. Early treatment with medication and infant stimulation is important for improved developmental outcome. Also associated with IS the electrodecremental event (EDE), which appears on the EEG as an attenuation of the signal and correlates with the observed clinical spasm.

SUMMARY

In accordance with an aspect, there is provided a system for real-time brain monitoring. The system comprises at least one processor, and a memory comprising instructions which when executed by the at least one processor configure the at least one processor to receive sensor data obtained by a collector device coupled to a plurality of sensors for pre-processing real-time raw sensor data acquired from the plurality of sensors for monitoring a patient's brain, determine using the sensor data a connectivity matrix having connectivity values, a connectivity value for each pair of channels, and a real-time brain value index corresponding to a real-time brain state of the patient, generate visual elements for an interface in real-time, and send signals to display the interface with the visual elements based on the issued control commands from the server. Each sensor corresponding to a channel. The visual elements represent the real-time brain value index to depict the brain state of the patient and a connectivity map for the connectivity matrix. The connectivity map visually indicates the channels of the sensors and a connecting line between a pair of channels representing a strength of connection between the pair of channels. The at least one processor is configured to issue control commands to update the interface using the generated visual elements.

In accordance with another aspect, there is provided a method of real-time brain monitoring. The method comprises receiving sensor data obtained by a collector device coupled to a plurality of sensors for pre-processing real-time raw sensor data acquired from the plurality of sensors for monitoring a patient's brain, determining using the sensor data a connectivity matrix having connectivity values, a connectivity value for each pair of channels, and a real-time brain value index corresponding to a real-time brain state of the patient, generating visual elements for an interface in real-time, and sending signals to display the interface with the visual elements based on the issued control commands from the server. Each sensor corresponding to a channel. The visual elements represent the real-time brain value index to depict the brain state of the patient and a connectivity map for the connectivity matrix. The connectivity map visually indicates the channels of the sensors and a connecting line between a pair of channels representing a strength of connection between the pair of channels. The at least one processor is configured to issue control commands to update the interface using the generated visual elements.

In accordance with another aspect, there is provided a system for real-time brain monitoring. The system comprises at least one processor, and a memory comprising instructions which when executed by the at least one processor configure the at least one processor to receive sensor data obtained by a collector device coupled to a plurality of sensors for pre-processing real-time raw sensor data acquired from the plurality of sensors for monitoring a patient's brain, determine a connectivity matrix having connectivity values, generate visual elements for an interface in real-time, and send signals to display the interface the interface with the visual elements based on the issued control commands from the server. Each sensor corresponding to a channel. The visual elements represent a connectivity map for the connectivity matrix, the real-time brain value index and the treatment data. The visual elements depict the channels, connections between the channels, and strengths of the connections. The at least one processor is configured to issue control commands to update the interface. The brain value index corresponds to a real-time brain state of the patient.

In accordance with another aspect, there is provided a method for real-time brain monitoring. The method comprises receiving sensor data obtained by a collector device coupled to a plurality of sensors for pre-processing real-time raw sensor data acquired from the plurality of sensors for monitoring a patient's brain, determining a connectivity matrix having connectivity values, generating visual elements for an interface in real-time, and sending signals to display the interface the interface with the visual elements based on the issued control commands from the server. Each sensor corresponding to a channel. The visual elements represent a connectivity map for the connectivity matrix, the real-time brain value index and the treatment data. The visual elements depict the channels, connections between the channels, and strengths of the connections. The at least one processor is configured to issue control commands to update the interface. The brain value index corresponds to a real-time brain state of the patient.

In accordance with another aspect, there is provided a system for real-time brain monitoring. The system has a plurality of sensors for acquisition of (near) real-time raw sensor data for monitoring a patient's brain, each sensor corresponding to a channel. The system has a collector device coupled to the plurality of sensors for pre-processing the real-time raw sensor data. The system has a server with an acquisition unit to receive sensor data from the collector device. The server has a processor to compute, using the sensor data, a connectivity matrix having connectivity values, a connectivity value for each pair of channels, and a real-time brain value index corresponding to a real-time brain state of the patient. The server has a presentation unit to generate visual elements for an interface in real-time, the visual elements representing the real-time brain value index to depict the brain state of the patient and a connectivity map for the connectivity matrix, the connectivity map visually indicating the channels monitored by the sensors and a connecting line between a pair of channels representing a strength of connection between the pair of channels, the server system having a display controller to issue control commands to update the interface using the generated visual elements. The system has a display device to display and update the interface with the visual elements based on the issued control commands from the server.

In some embodiments, the server computes, for each pair of channels, a phase synchronization value for an angle between the respective pair of channels using the sensor data for the respective pair of channels, wherein entries of the connectivity matrix are the phase synchronization values the pairs of channels.

In some embodiments, the server generates a boolean connectivity matrix based on the connectivity matrix, such that an entry of the boolean connectivity matrix is 0 if a corresponding connectivity value is lower than a threshold value, and 1 if a corresponding connectivity value is higher than the threshold value, wherein the server computes the threshold value from sensor data for a normal adult with eyes open, wherein a connected channel is defined as an entry that is 1, wherein the server generates the brain value index using the boolean connectivity matrix.

In some embodiments, the brain value index may be computed based a total number of possible pairs of channels given a specific channel montage N=Nc!/2!(Nc−p)!, Nc being a number of channels, p being a number of connected pairs of channels, p being calculated using a threshold value and the connectivity values of the connectivity matrix.

In accordance with one aspect, there is provided a system for real-time brain monitoring having a plurality of sensors for acquisition of (near) real-time raw sensor data for a patient's brain; a collector device coupled to the plurality of sensors for pre-processing the real-time raw sensor data; a server for processing the real-time raw sensor data to compute a connectivity matrix for brain entropy, a real-time brain value index and treatment guidance, the server system having a display controller to issue control commands to continuously update an interface in real-time, the brain value index corresponding to a real-time brain state; and a display device having the interface to generate and update a visual representation of the real-time brain value index and the treatment guidance based on the issued control commands from the server.

In some embodiments, the treatment guidance triggers treatment for organ donation upon detecting that the patient is a candidate for organ donation.

In some embodiments, the server computes the connectivity matrix for brain entropy.

In some embodiments, the treatment guidance provides a monitoring state, an intervention state and a resuscitate state.

In some embodiments, the display device provides feedback data to refine or update the processing by the server.

In some embodiments, the server computes phase synchronization for each channel pair angle, where the entries of the connectivity matrix are values for each pair combination.

In some embodiments, the server computes the connectivity matrix as a Boolean connectivity matrix where the entries are, 0 if a corresponding index is lower than a threshold, and 1 if higher, where the server computes a threshold from the average of indices of normal adults with eyes open, where connected channels are defined as entries 1.

In some embodiments, the brain value index or functionality index or brain viability index (BVI) calculation may be defined using a total number of possible connections given a specific channel montage as N=Nc!/p!(Nc−p)!(Nc is 8 to 12) where Nc is the number of channels or electrodes, and where p (the number of connected pairs of channels) is calculated for that instance using a threshold value, wherein the server system computes an entropy value associated of the p values and calculates a normalized entropy to a value between 0 and 1.

In some embodiments, the server implements machine learning to compute the brain value index based on historical data for the patient or other patients.

In some embodiments, the server implements machine learning to generate recommended treatments as part of the treatment guidance based on historical data for the patient or other patients.

In some embodiments, the real-time raw sensor data is linked with a patient identifier and time indicia.

In accordance with another aspect, there is provided a processing device for real-time brain monitoring having a network interface for acquisition of real-time raw sensor data for a patient's brain; a server for processing the real-time raw sensor data to compute a connectivity matrix for brain entropy, a real-time brain value index and treatment guidance, the server system having a display controller to issue control commands to an interface, the brain value index corresponding to a real-time brain state; a storage device for storing computed real-time brain value indices; and a display device having the interface to generate and update a visual representation of the real-time brain value index and the treatment guidance based on the issued control commands from the server.

In accordance with another aspect, there is provided a process for real-time brain monitoring involving acquiring real-time raw sensor data for a patient's brain from a plurality of sensors; pre-processing the real-time raw sensor data; processing, at a server, the real-time raw sensor data to compute a connectivity matrix for brain entropy, a real-time brain value index and treatment guidance, the server system having a display controller to issue control commands to an interface, the brain value index corresponding to a real-time brain state; generating and updating, on a display device having the interface, a visual representation of the real-time brain value index and the treatment guidance based on the issued control commands from the server.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

In the figures.

DETAILED DESCRIPTION

Embodiments described herein relate to systems, processes and devices for real-time brain monitoring using sensors and signal processing rules. As an example, the real-time monitoring may detect different brain states of a patient for different use cases. Example use cases include brain wave signal pattern detection for patients of a specific age range, migraines, anxiety disorders, epilepsy, infantile spasms (now known as epileptic spasms) and hypsarrhythmia or electrodecremental events, concussions, comatose or other brain injury. The systems, processes and devices for real-time brain monitoring may use sensors to acquire neurological or brainwave signal data and process the signal data to compute a real-time, changing brain state index or brain value index. The system may automatically suggest treatment for the purposes of recovery based on the brain value index. For example, treatment may be for anxiety disorders, or for epileptic spasms and hypsarrhythmia or decremental events, based on the brain value index. Each anxiety disorder can be associated with a threshold value or range of values configured for a patient. The computed brain value index can be compared with the threshold value or range of values to determine an anxiety disorder, for example. It should be noted that the references to “epileptic spasms” and “infantile spasms” herein are interchangeable. Infantile spasms are now known as epileptic spasms.

Figure 1:
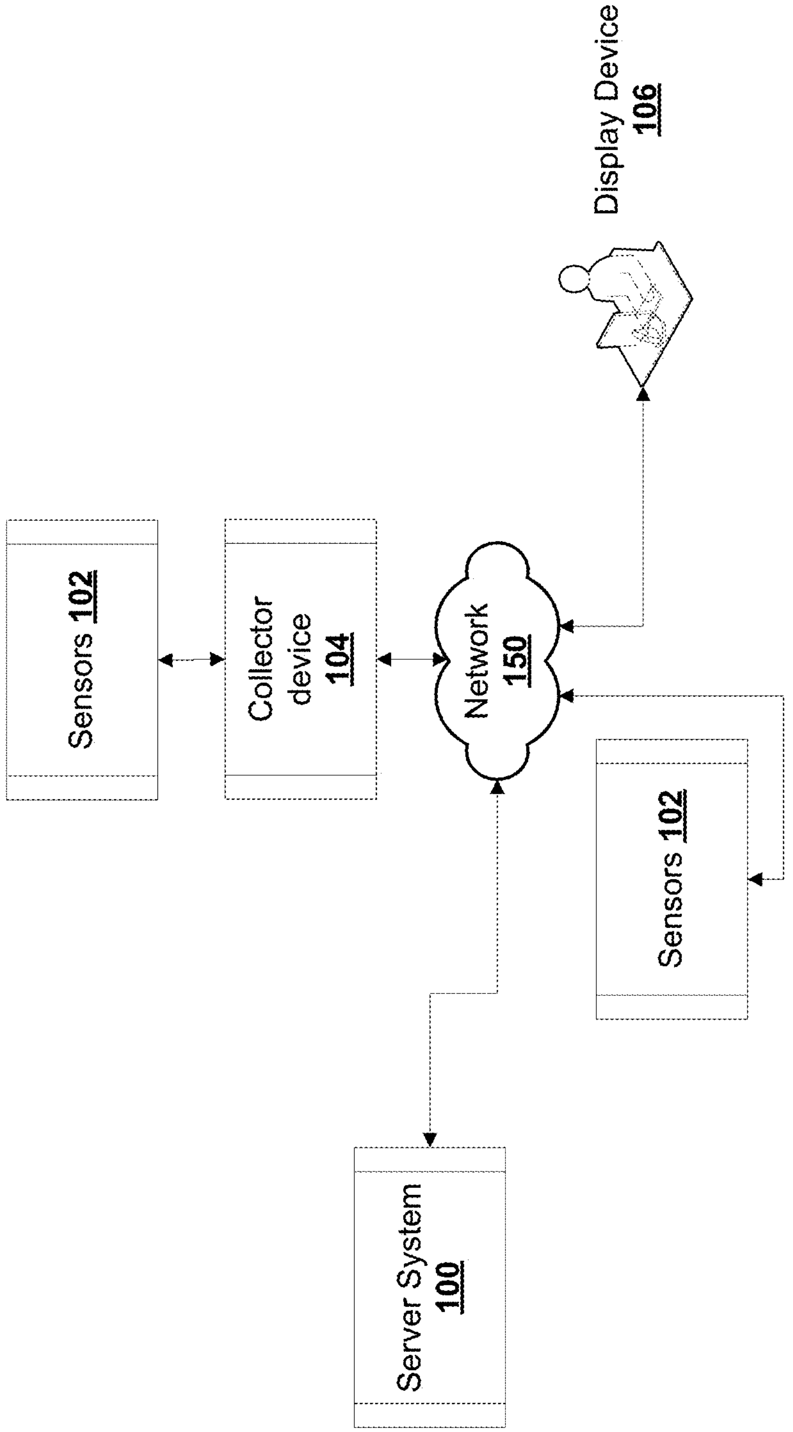
FIG. 1 is a diagram of a system for real-time brain monitoring according to some embodiments.

FIG. 1 shows an example system for real-time brain monitoring. The system may include sensors 102 coupled to a patient for real-time brain state monitoring. The sensors 102 may include electroencephalography (EEG) sensors (e.g. electrodes) to record electrical activity of the brain when placed on the scalp of the patient, for example. The sensors 102 may generate brainwave signal data for the patient. The sensors 102 measure voltage fluctuations resulting from spontaneous electrical activity, neural oscillations or brainwaves over a period of time. Accordingly, the brainwave signal data may be time coded. Sensors 102 may also include other types of biological sensors to generate additional biological or physiological data signals such as heart rate, temperature, and so on. The sensors 102 data feeds include time codes that can be cross-referenced to timecodes of other data feeds.

The system includes a collector device 104 coupled to the sensors 102 for pre-processing the real-time raw sensor data. A server system 100 processes the real-time raw sensor data to compute a connectivity matrix, a real-time brain value index, treatment guidance and other data. The server system 100 has a display controller to issue control commands to a display device 106 to continuously update an interface in real-time. The brain value index (BVI) can correspond to a real-time brain state. For example, the brain state can correspond to an anxiety state (or different levels of anxiety). The anxiety state can correspond to a threshold value or a range of threshold values. There can be different anxiety states (no, low, medium, severe, panic attack). The display device 106 has an interface to generate and update a visual representation of the real-time BVI and the treatment guidance based on the issued control commands from the server.

Sensor 102 can refer to an electrode for gathering physiological information from a patient or control subject. Sensors 102 can refer to channels and are located on a portion of a patient’s brain. In some instances, sensor 102, electrode and channel may be used interchangeably. Example sensors 102 can include an EKG (heart rate), EEG (brainwave) and other bio-signal devices. Montage can refer to a specific arrangement of EEG electrodes on the scalp. For example, there can be the international 10-20 montage of 10 to 20 electrodes or a subset of these.

In some embodiments, the sensors 102 can be EEG sensors to acquire raw EEG data from the patient. The sensors 102 include electrodes to record electrical activity of a brain of the patient as brainwave signals or raw EEG data. The sensors 102 can be placed at different locations on a patient’s scalp or head to capture the brainwave signals. The EEG data can refer to the recording of electrical activity of a brain (e.g. brainwave signals) captured by the sensors 102 over a period of time. As noted, a sensor 102 includes an electrode configured to capture brainwave activity. The electrode can be referred to as an EEG channel. The sensors 102 can include multiple EEG channels to capture brainwave signals. The electrodes can be positioned on different locations of the patient’s scalp and head to represent different channels. The EEG channels can refer to different locations on the patient. The sensors 102 can involve different EEG channels or a different arrangement or layout of positions of electrodes on the patient’s scalp and head. The sensors 102 provide an electrode network or array that evolves depending on the desired number of EEG channels and the position of the EEG channels relative to the patient’s scalp or head. Different parts of the brain serve different functions and placement of the electrodes on different parts of the brain can capture brainwave data signals that correspond to different cognitive functions. In some embodiments, the sensors 102 are configured for acquisition of (near) real-time raw sensor data for a patient’s brain (e.g. brainwave signal data).

In some embodiments, the system includes a wearable device with particular sensor 102 or electrode placements to standardize the positioning of sensors 102 or electrodes to access brainwave signal data at specific brain locations that serve specific brain functions. The wearable device can have attachments for electrodes at particular positions and the electrodes can be removably attached to the wearable device at the different positions to provide a variety of attachment options and configurations for positioning the electrodes. By way of example, electrode placements can capture brainwave data signals representing activity at the prefrontal cortex and frontal lobe. A location or site of an electrode or EEG channel can be identified or referenced by a letter for the lobe and a number for the hemisphere location. For example, the letters F, T, C, P and O stand for frontal, temporal, central, parietal, and occipital lobes, respectively. Even numbers can refer to electrode positions on the right hemisphere, whereas odd numbers refer to those on the left hemisphere. A “z” (zero) can refer to an electrode placed on the midline. Example EEG channels can include T3, F7, F8, T4, T5, O1, O2, T6. In addition to these combinations, the letter codes A, Pg and Fp can identify the earlobes, naso-pharyngeal and frontal polar sites respectively. Two anatomical landmarks can be used for the positioning of the EEG electrodes. One landmark is the nasion which is a depressed area between the eyes, just above the bridge of the nose and another landmark is the inion, which is the lowest point of the skull from the back of the head and is normally indicated by a prominent bump.

For ease of application, particularly in an intensive care setting where patients are in a recumbent position, embodiments described herein can employ a coronal EEG montage which combines both ease of application to the scalp and provides important information from frontal, temporal and occipital lobes. The frontal and temporal regions are particularly vulnerable in all types of brain injury. This montage coupled to server system 100 can provide information on functioning within a hemisphere when examining relationships between frontal and occipital electrodes. This also provides information on functioning across hemispheres when the relationship between pairs of electrodes is examined: F7 and F8, T3 and T4, and so on. The eight electrode montage can be processed in real-time and results in 28 possible electrode pairs (N=Nc!/p!(Nc−p)! Where p is the number of connected pairs and Nc is the number of electrodes or sensors 102 in the system (8 in this example). For this example there can be 14 different functionality or Brain Value Indices, the number being constrained by the number of electrodes and the arrangement, as will be explained herein. Fewer electrodes can result in fewer indices. More electrodes can result in more indices. For example, more electrodes, such as the 144 channels of magenetoencephalography (MEG) produce 10296 possible pairs. They can be processed retrospectively using the processes described herein to calculate the phase synchrony, connectivity and entropy indices.

Figure 10:
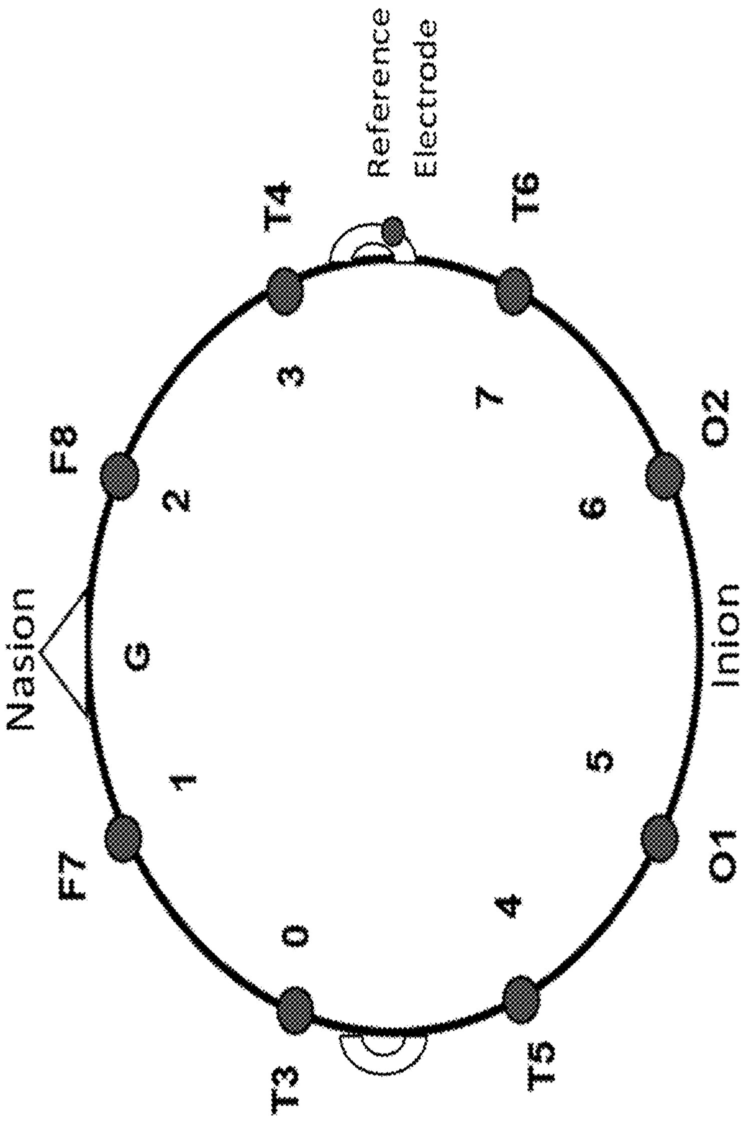
FIG. 10 is an example hardware arrangement of sensors to acquire EEG data.

FIG. 10 shows an example hardware setup for sensors 102. The sensors 102 or electrodes can be arranged as a subset of the international 10-20 montage for EEG electrode placement. The montage is coronal in that when looking down at the head of the subject, the right side of the head from the nose (Nasion) to the back of the head (Inion) is identified by even numbers and the left side of the head, by odd numbers. The electrodes thus follow the circumference of the head in the horizontal plane. The letters correspond to the lobes that underlie the electrodes: Frontal, (F), Temporal (T) and Occipital (O). The ground (G) electrode is in the middle of the forehead and the reference electrode is placed on either ear. For this example, the right ear may be used for the ground. The eight electrodes are numbered starting with 0 that corresponds to T3 which is left anterior temporal and the numbers continue across the front of the head to the right anterior temporal electrode. The numbering resumes starting with the left posterior temporal electrode (T5) and continues across the back of the head to the right posterior temporal electrode. Accordingly, the electrodes correspond to EEG channels T3, F7, F8, T4, T5, O1, O2, T6.

In some embodiments, the real-time raw sensor data is linked with a patient identifier and time indicia. For example, the recording can be automatically saved with a file name of “DATE-TIME-LENGTH.bin” When the recording is stopped, a study code or patient identifier can be added to the file.

Referring back to FIG. 1, a collector device 104 is coupled to the sensors 102 for pre-processing the real-time raw sensor data or brainwave signal data. The sensors 102 provide raw sensor data (e.g. raw EEG data) to the collector device 104. The collector device 104 is configured to pre-process the sensor data, such as by filtering out noise, to generate filtered brainwave signal data. As further examples, the collector device 104 may implement pre-processing for artifact reduction, reduction of volume conduction and reference electrode removal, for example. The collector device 104 connects to a server system 100 via network 150 to transmit the brainwave data collected from sensors 102. In some example embodiments, server system 100 may be directly connected to sensors 102 to directly receive the raw sensor data or brainwave signal data to provide a stand-alone solution.

The server system 100 is configured to process the real-time raw sensor data or brainwave signal data to compute a connectivity matrix for brain entropy, a real-time brain value index (BVI) and treatment guidance. The brain value index can also be referred to as a functionality index or brain viability index. The brain value index can correspond to a real-time brain state of a patient.

The server system 100 is configured to compute, using the sensor data, a connectivity matrix having connectivity values, a connectivity value for each pair of channels. The server system 100 is configured to generate visual elements in real-time that represent the real-time brain value index to depict the brain state of the patient and a connectivity map for the connectivity matrix. The connectivity map visually depicts the channels and a connecting line between a pair of channels representing the strength of connection between the pair of channels. The connectivity map may show multiple connecting lines between channel pairs. The brain state can indicate different anxiety states or disorders, for example.

Sensors 102 can include different types of sensors to capture different biological and brainwave data. Sensors 102 correspond to different channels. The server system 100 processes the sensor data using processing rules to detect patterns and evaluate cortical and subcortical activity in conscious and unconscious states. The server system 100 computes a connectivity matrix for brain entropy to evaluate the number of “connections” between areas of the brain and the associated entropy and complexity. Conscious states may result from higher entropy and complexity that are dependent on the number of configurations of connected pairwise combinations computed from the raw signals. The number of pairwise channel connection combinations sets a limit on the number of possible configurations.

As channels may be connected or not connected, entropy and complexity can be maximized when the number of connected channel configurations is equal to half of all possible channel configurations. Entropy occurs when the individual is processing sensory inputs in a normal manner (e.g. awake with open eyes). Half of the number of configurations of interactions may represent the most probable distribution of energy and is associated with conscious awareness. These results encapsulate three main theories of cognition: the metastability of brain states, the global workspace theory and the information integrated theory. Consciousness may represent thus an optimal channel for accessing sources of free energy and is an emergent property of the distribution of energy (information) in the nervous system. Too much connectivity or too little connectivity may indicate abnormal brain states.

In the case of anxiety, while the patient is conscious, he or she is not fully functional as seen in the physiological changes (increased heart rate, gastrointestinal upset, sweating, increased respiratory rate). Thus the entropy and connectivity are lower than in the non-anxious, conscious state.

In the case of epileptic spasms and hypsarrhythmia, while the patient is conscious, he or she is not fully functional as seen in the physiological changes (increased heart rate, gastrointestinal upset, sweating, increased respiratory rate). Thus the entropy and connectivity are lower than in the non-anxious, conscious state.

Server system 100 computes the Brain Value Index (BVI) using the connectivity matrix in some embodiments. The connectivity matrix includes values corresponding to connections between different channel pairs which are calculated using the sensor data. BVI may be used interchangeably herein with normalized entropy and functionality index.

Figure 11A:
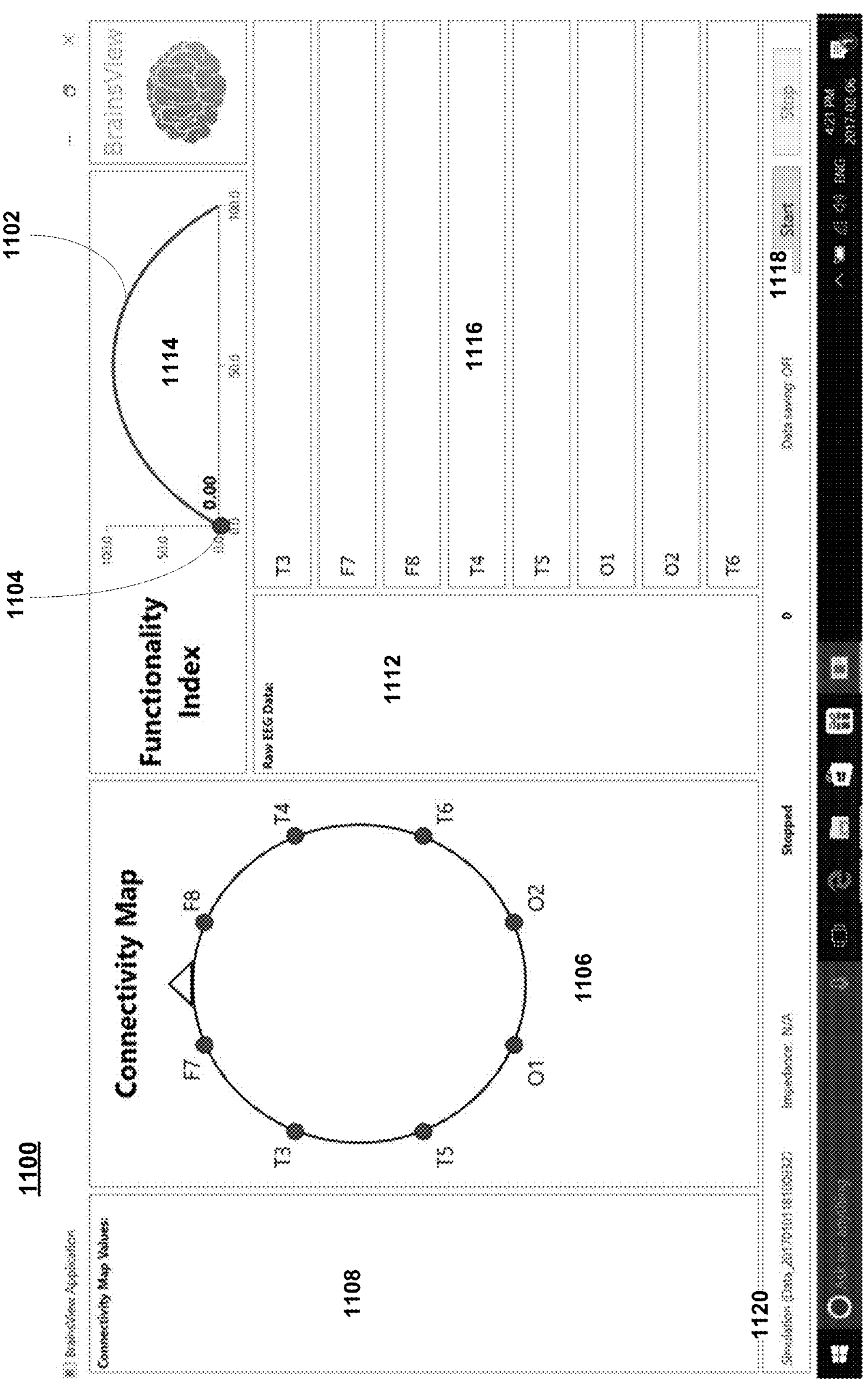
FIG. 11A is an example interface with visual representations as described herein.

Referring to FIG. 11A there is shown an example interface 1100 with a BVI marker 1104 visually depicted along a curve 1102 as a portion of a graphical display. The BVI marker 1104 can move along the curve 1102 to different positions in response to BVI values computed in real-time by server system 100.

Server system 100 can generate a visual element for an interface 1100 that depicts an inverted U-shaped curve 1102 to plot the number of connected channels against entropy or BVI values. In this example, the x-axis represents the number of connected channels normalized on a scale of 0 to 100, with 100 indicating that all possible channels are connected, 0 indicating that no channels are connected, and 50 indicating that half of the number of channels are connected. The maximum BVI value is at the centre of the curve 1102 which can occur when half of the channels are connected. The BVI values can go down when more or less than half of the number of possible channels are connected. The U-shaped curve 1102 reflects this proportional relationship between the number of connected channels and the BVI value. Server system 100 can generate a visual element for a BVI marker 1104 at a position along the U-shaped curve 1102 to indicate the real-time BVI value on interface 1100.

The BVI values can be used for market research with clinicians, for example. In statistical thermodynamics, entropy is a measure of the number of microscopic configurations that a thermodynamic system can have when in a state as specified by certain macroscopic variables. In the case of brain function, entropy can be the number of connections between neuronal networks in a specific brain state, where the alert, awake state with eyes open represents a connection set and is the total information contained within functional neuronal networks. For example, normalized entropy can be computed based on the BVI (e.g. regular entropy) value divided by the maximum entropy (at the peak of a curve 1102), and multiplied by 100. This can provide the clinically useful 0 to 100 values along the axes of the inverted U-shaped curve 1102. For the maximum entropy, the BVI will be 100 and the number of connected channels will be 50.

Figure 30:
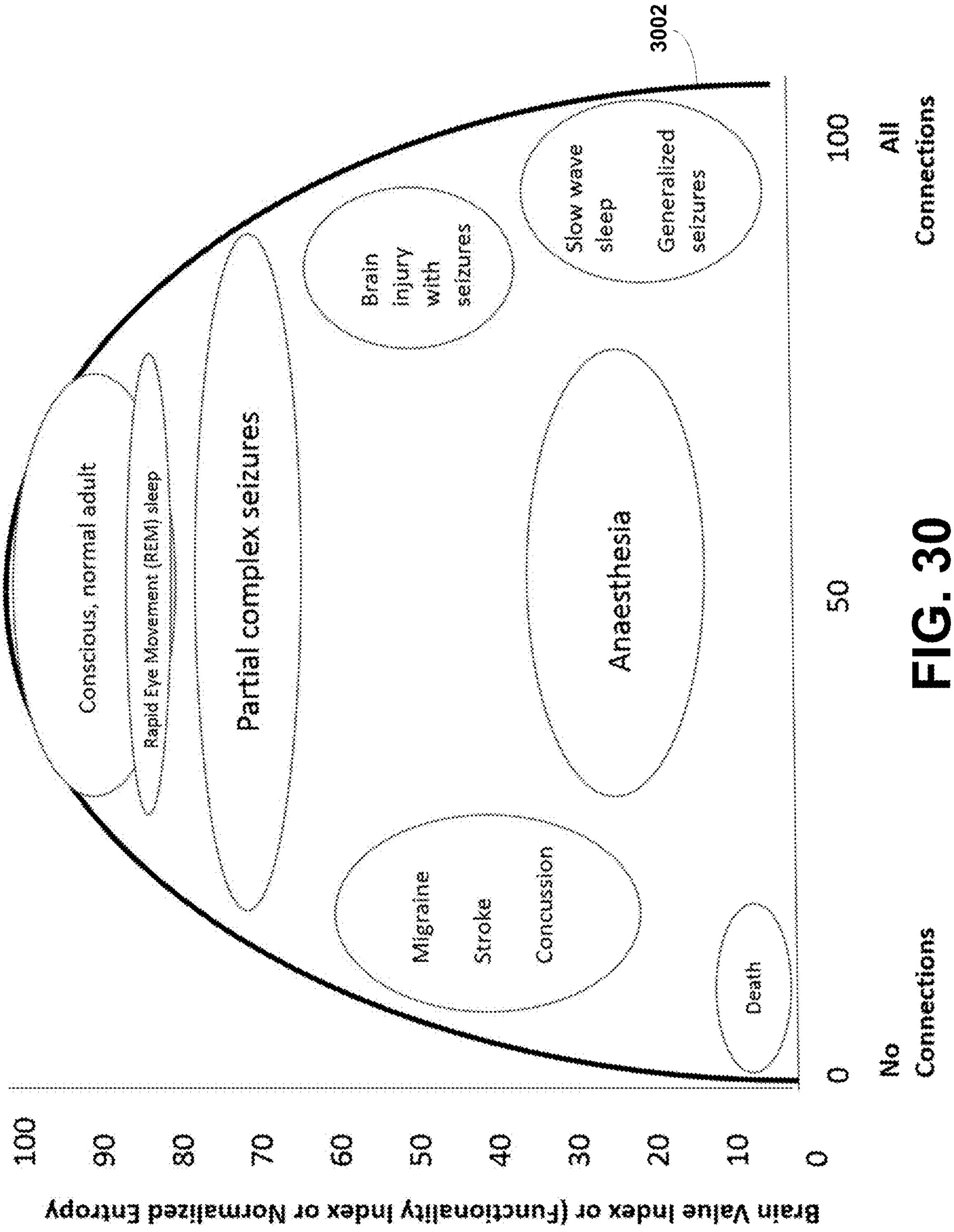
FIG. 30 is an example interface with a visual representation for brain value index values as described herein.

Referring to FIG. 30 there is shown a graphical representation of the inverted U-shaped curve 3002 that plots the number of connections against the BVI values. Different regions or positions along the curve can correspond to different brain states and conditions. The interface can assist a clinician to identify brain states by generating a specific visual representation of data. The brain value index is plotted against the number of connections shown in the connectivity matrix in some embodiments. The position of the BVI marker along the curve 3002 corresponds to different brain states, such as the examples shown. This transformation of a complex data set of raw brainwave signals provides a clear visualization for a clinician.

In some embodiments, the server 100 computes a connectivity matrix from the brainwave data. The connectivity matrix is used by the server system 100 in order to compute the BVI values. In some embodiments, the server 100 computes phase synchronization for each channel pair angle. The entries of the connectivity matrix are values for each pair combination. The server 100 can use the entries to generate a visual connecting line between channel pairs in the connectivity map.

Connectivity is a function of phase synchrony values computed by server 100, also known as the R index, and can be an integer between 0 and 1, for example. Phase synchrony (synchronization) evaluates the connectivity between 2 oscillating signals, such as the EEG waveform output from 2 channels. It is an integer value between 0 and 1. Server 100 can calculate phase synchrony using the Hilbert as follows: $R=\langle e^{(i\Delta\theta)}\rangle$ where $\Delta\theta$ is the phase difference (or angle) between two signals. The value can be dependent on the length of time specified for the calculation (1 second running window for our device) and the frequency of the signal (3 Hz for our device).

Server 100 can generate a connectivity map for an interface of a display that indicates the channels and connecting lines between channel pairs based on the strength of connection between a respective channel pair.

Referring back to FIG. 11A there is shown a connectivity map 1106 as part of interface 1100. The connectivity map 1106 visually depicts an arrangement of channels. In some embodiments, server system 100 is configured to generate connecting lines between channels of the connectivity map 1106 to indicate the strength of the connection between channels. For example, a lighter line can indicate a weaker connection (e.g. lower connectivity value) than a darker line. The connectivity map values may be computed using the sensor data. Accordingly, the connecting line changes visually depending on the strength of the connection. The interface 1100 can also include a listing of connectivity map values. Each channel pair can have a corresponding connectivity map value. A list of values may be displayed as visual elements 1108 and may range between 0 and 1. The raw EEG data may also be displayed for each channel.

For example, the connectivity map 1106 can be a graphical depiction of the 8 electrodes (channels) representing the strength of the connectivity (e.g. phase synchronization) between each of the possible channel pairs. The threshold of a phase synchrony value can be 0.45, for example. The threshold can be calculated by server 100 using sensor data from normal adult subjects in the awake state with eyes open. Four levels of connectivity strength are defined by the following ranges and illustrated with connecting lines of different colours and thicknesses. The example connecting lines are shown as light grey and 1 point thickness defines connectivity between a pair of electrodes with a phase synchrony value of 0.45 to <0.6; Medium grey and 1.5 point thickness for a phase synchrony value of 0.6 to <0.8; Dark grey and 2 point thickness for a phase synchrony value of 0.8 to <0.9; and black with a 3 point thickness for a phase synchrony value of 0.9 to 1.0<0.6. This is an example visual representation.

The server 100 computes the connectivity matrix by calculating entropy from the phase synchrony values for each electrode pair. The server 100 can also compute a boolean matrix such that each electrode pair's phase synchrony is compared to the threshold (0.45) and assigned a "0" if it is below the threshold or "1" if it is above the threshold. This threshold generates a simplified view of the complex data while still giving clinically useful discernible output.

In some embodiments, the server computes the connectivity matrix as a boolean connectivity matrix where the entries are, 0 if a corresponding index is lower than a threshold, and 1 if higher, where the server computes a threshold from the average of indices of normal adults with eyes open, where connected channels are defined as entries 1. The threshold of the phase synchronization (R) can be generated from averaging the mean phase synchrony value for control subjects at 3 Hz over 10 second epochs in the alert state with eyes open.

The server system 100 calculates a Brain Value Index (BVI) or Functionality Index or "normalized entropy" using connectivity values for the channel pairs of the total number of possible connections. Phase synchronization is calculated for each pair of channels and a "connectivity" matrix S is obtained, whose entries are the average values of the synchrony index for each pair combination. From this one, a boolean connectivity matrix B is calculated, with 0 entry if the corresponding synchrony index is lower than a threshold, and 1 if higher. We define two channels "connected" if the corresponding entry in matrix B is 1. Then we use the combinations of connected channels as a 'complexity' measure. The total number of possible pairs of channels given a specific channel montage is N=Nc!/p!(Nc−p)! where p is the number of connected pairs and Nc is the total number of channels or electrodes in the recording system, such as 144-146 in case of MEG sensors, between 19 and 28 in case of scalp EEG and 8 channels in an example prototype. The channel numbers are specified, below, in each case. For instance, in example MEG recordings there may be Nc=144, thus N=10296 possible pairs of connected sensors. For each subject server system 100 calculates p (the number of connected pairs of channels) in the different behavioural stages, using the threshold of the synchrony index of 0.45 based on the average phase synchronization of normal adults in the alert state with eyes open, and estimate the number of possible combinations of those p pairs, C, using the binomial coefficient again: C=N!/p!(N−p)!. These calculations represent the combinatorial problem: given a maximum total of N pairs of connected signals, in how many ways our experimental observation of p connected pairs (that is, the number of 1's in matrix B) can be arranged. The entropy and Lempel-Ziv complexity associated with those p values are then computed by server 100. In the final step, each entropy value is divided by the maximal entropy value (e.g. 50 for a normal adult) and then multiplied by 100. A normal brain needs to synchronize (measured by the phase synchrony values). If the brain is too connected then it may be over excited and if not connected at all then may be non-responsive. Examples visual representations of different brain states are shown in FIG. 30.

The possible values for the Brain Value Index are constrained by the number of channels and configuration of electrodes. In the 8 channel example prototype there can be 14 different values of the brain value index (rounded to whole numbers): 22, 37, 49, 59, 67, 74, 81, 84, 90, 94, 96, 98, 99, 100. There are 28 possible connections or channel pairs. There may be half the number of BVI values, or 14. For the example with 8 channels, the normalized entropy can be 1 of 14 possible values on either side of the curve. A further possible value is the maximum entropy value (centre of the curve), which is also a unique value. That is, there are 14 other unique values (in addition to the maximum entropy value) on each side of the centre point. Accordingly, for this example, there can be 29 total values. There is also a 0 value when there are 0 connections.

The BVI values are based on the total number of possible connections for a given number of channels. In the example with 8 channels there are 28 possible connections (plus 1 for the 'no connection case'). For each 'number of connections' at a given point in time, server 100 can calculate the Brain Value Index, which only depends on the number of connections, so this is why there are only 15 possible normalized entropy values in this example since the curve is symmetric.

An approximation for entropy S or Brain Value Index can be represented as:

$$\text{Entropy}(N)=C*\log(C/(C-N))-N*\log(N/(C-N))$$

where

C=the maximum number of total pairs of connections

N=the number of active connections log=the natural logarithm

The normalized entropy can be represented as:

$$\text{normalizedEntropy}=100*\text{Entropy}/\text{maxEntropy}$$

where maxEntropy is:

$$\text{maxEntropy}=\text{Entropy}(C/2)$$

or $$\text{maxEntropy}=C*\log(C/(C-(C/2)))-(C/2)*\log((C/2)/(C-(C/2)))$$

A different number of electrodes can generate different set of possible values for the Brain Value Index. For example, they can be intermediate values on the curve.

The server system 100 has a display controller to issue control commands to continuously update an interface at a display device 106 in real-time. The display device 106 has an interface to generate and update a visual representation of the real-time brain value index and the treatment guidance based on the issued control commands from the server system 100. In some example embodiments, the collector device 104 and server system 100 may couple to display device 106 to control rendering on display device 106 and provide visualizations of the brainwave data from the sensors 102, brain value index and connectivity matrix. Feedback data received in response to the display on display device 106 of the visualizations of the brainwave data from the sensors 102 may also be used to refine collector device 104 processes, for example.

The server system 100 processes the brainwave data for real-time brain monitoring. The server system 100 connects to display device 106 to control rendering on display device 106 and provide visualizations of data in real-time as interface elements of an interface. Feedback data may be received at display device 106 which may be used for machine learning or training to refine server system 100 processing rules, for example. The server system 100 may be remote or local to other components to provide remote input, remote monitoring or remote viewing in various embodiments. The server system 100 may integrate anonymized sensor data from other patients with similar treatments or conditions for machine learning and benchmarking. The server system 100 may integrate historical data for the patient for machine learning and benchmarking. In some embodiments, the server system 100 can access a cloud storage device that correlates patient data.

The server system 100 is configured for real-time brain monitoring and generates output data to update an interface on a display device 106 with interface elements to provide visual representations of the output data and a treatment guide for the patient. Accordingly, the server system 100 provides discernible effects at least at the interface of display device 106. For example, the treatment guide can indicate or recommend the patient as a potential organ donor based on the computed brain state being within an organ donation threshold or range. For example, organ donation happens in an intensive care unit (ICU) and occurs for certain patients when recovery is not expected, for example. Currently the primary pathway by which a patient becomes an organ donor is through brain death. This represents a small percentage of patient deaths. Donation after cardiac death can increase the number of available organs for transplantation. Determination of the time of death is critical to satisfy the dead donor rule, while maximizing organ viability after cardiac death because of lack of blood flow with a non-beating heart. Organ donation may be determined using the organ donation threshold or range that is configured to detect when recovery is not expected based on the brain value index computed using brainwave signals of the patient. Currently, for organ donation after cardiac death, the potential donor, i.e. the patient is identified and then observed and monitored with a cardiac monitor in the operating room until the cardiac arrest occurs. The time of observation is not predictable and varies with individual patients.

Figure 25:
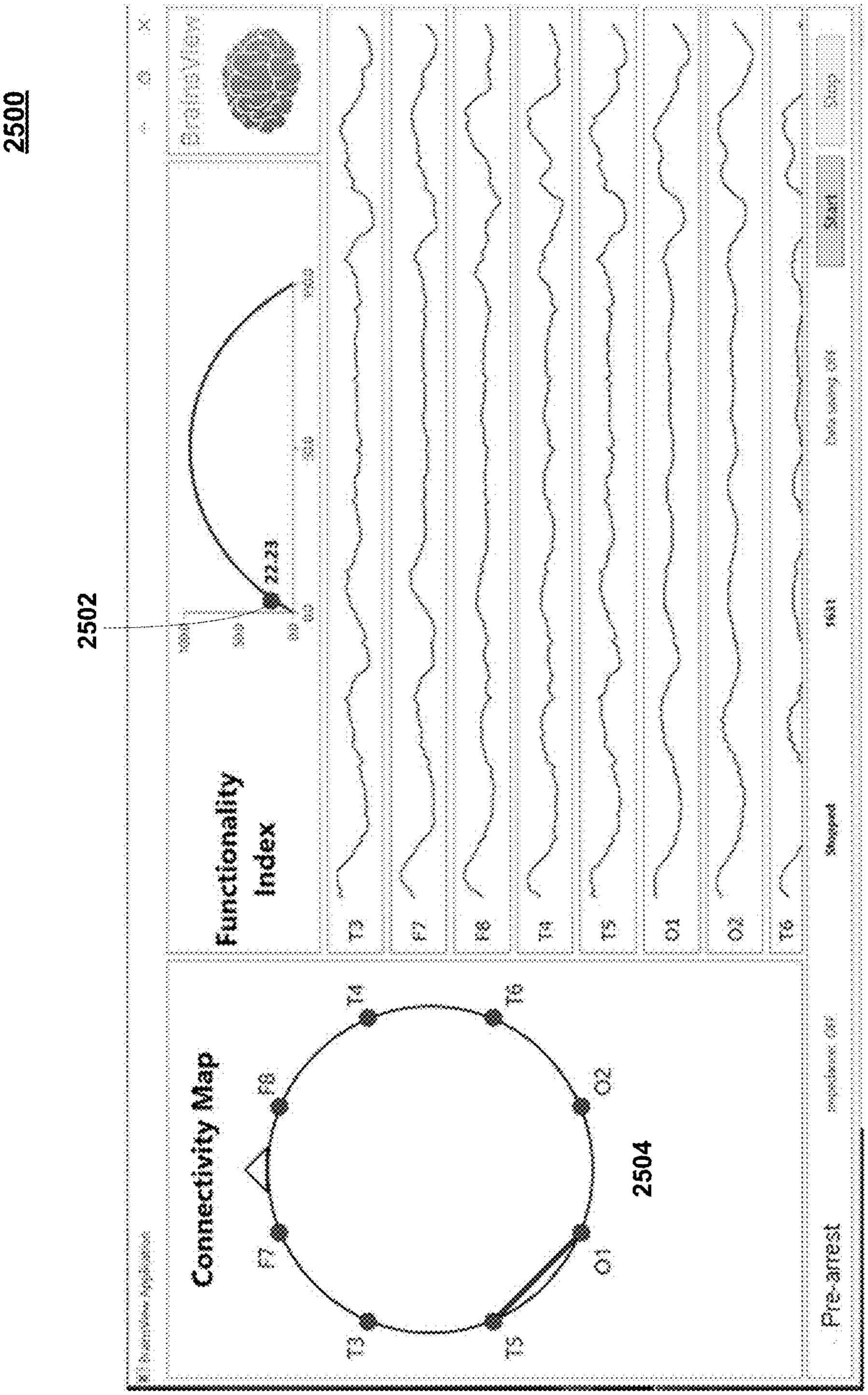
FIG. 25 is an example interface with visual representations as described herein.

FIG. 25 provides an example of patient data that illustrates how the system 100 can be used in organ donation after cardiac death. Cardiac arrest has focused on the changes in heart rhythm. Brain changes occur prior to cardiac arrest. Being able to better monitor cardiac arrest patients who have been resuscitated or those at risk for cardiac death would benefit both the patient and the organ donation programs. The interface 2500 provides a graphical display of EEG data signals (slow waves), Functionality Index (22 on the left side of the curve) or BVI marker 2502 and Connectivity Map (T5 and O1 only) 2504 of a patient who was being monitored in a coma with an EEG sensor hardware device. The original EEG recording used 19 channels, so the 8 channels corresponding to the prototype device can be extracted to be processed and displayed. This EEG pattern and Functionality Index preceded the patient's subsequent cardiac arrest by 2 minutes. Consistent functionality index below 37 has been associated with patient death and would be a trigger for either resuscitation or preparation for organ donation.

Graphical Display

The server system 100 processes the brainwave data to identify or detect features or patterns of optimal (or suboptimal) brain organization that allows for adequate processing of sensory stimuli and that may guide the emergence of cognition and consciousness. The server system 100 processes the brainwave data to identify or detect indicators of conscious and unconscious states of a patient's brain. As an example, normal wakeful states may be characterised by greater number of possible configurations of interactions within a patient's brain network. The greater number of interactions within a patient's brain network (information exchange) can represent highest entropy values and the brainwave data can indicate a probable distribution of information and energy. The server system 100 processes the brainwave data to identify or detect interactions within the brain network or lack thereof.

Consciousness arises from the organization of matter and may be considered an emergent property of the brain organization. Neurophysiologic recordings of brain activity (e.g. brainwave signals captured by EEG sensors) can show persistent fluctuating patterns of cellular interactions within a patient's brain network. This variability in fluctuating patterns of cellular interactions indicates a range of brain states. A brain has different configurations of connections of widely distributed networks that exchange information, and support the flexibility needed to process sensory inputs and cognition. Fluctuations in brain coordinated activity and metastable dynamics may be captured by EEG sensors as brainwave signals and used clinically to evaluate brain function. There may be certain general organization of cell ensembles that may be optimal for processing of sensory inputs (i.e. conscious awareness). An organising principle is the tendency toward maximal or more probable distribution of energy/matter. Brain organization may be a manifestation of the tendency towards a widespread distribution of energy or maximal information exchange. The server system 100 processes the brainwave data to implement real-time brain monitoring to evaluate and understand brain function and the interactions within the brain network.

The server system 100 captures brain waves signals using sensors 102. The server system 100 computes a (near) real-time brain value index to determine and evaluate a brain state. The server system 100 defines boundaries or ranges of values for the brain value index in order to define different brain states. That is, a particular brain state is associated with a range of values for the brain value index.

The server system 100 implements real-time brain monitoring by processing the brainwave signals captured by sensors 102 to compute the brain value index as an assessment of the patient's brain state.

In some embodiments, the server system 100 monitors brain function using sensors 102 and generates an interface on display device 106 to provide a visual representation of treatment guidance and an indicator for the real-time, changing brain value index. The server system 100 controls and updates the interface on display device 106 in real-time to update the visual representation of the brain value index and treatment guidance. The treatment guidance may include an indication or recommendation to continue the current treatment (monitor mode), re-evaluate the patient and adjust treatment (intervention mode), urgently intervene (resuscitation mode). The treatment guidance may also indicate if the patient is deemed or determined to be a candidate for organ donation based on the brain value index. These are illustrative example treatment guides and visual representations for the interface. The server system 100 integrates the brainwave data with other biological data such as brain and heart variability measures (e.g. received from sensors 102) with machine learning rules to provide individualized patient monitoring using the real-time, changing brain value index and treatment guidance. The interface on display device 106 may provide a graphical display of treatment guidance and the real-time brain value index for a patient may be self-referential with real-time updates.

In some embodiments, the server system 100 implements machine learning to compute the brain value index based on historical data for the patient or other patients. In a first step, a classifier algorithm is created by system 100. Each patient has a series of Functionality Index values and a known outcome (e.g. A dichotomous outcome of alive or dead). The output from the training set is used with a test set of new patient data in order to identify the patent state such as an anxiety state or an epileptic spasms and hypsarrhythmia state. Patient outcome based on new recordings would be predicted based on accumulation of Functionality Index values.

The interface provides a real-time indication of different brain states determined based on the real-time, changing brain value index computed by processing brainwave signals, along with treatment guidance for the different brain states. The interface can provide an indication of the brain value index using a graph representing ranges of brain function and with an indicator along the graph representing the real-time brain value index.

In some embodiments, the server system 100 generates treatment guidance for display at interface of display device 106. For example, the treatment guidance can provide an indication of a monitoring state, an intervention state and a resuscitate state in relation to the computed brain value index. In some embodiments, the display device 106 provides feedback data to refine or update the processing by the server system 100.

In some embodiments, the server system 100 implements machine learning to generate recommended treatments as part of the treatment guidance based on historical data for the patient or other patients. In some embodiments, the server system 100 may generate recommendations as part of the treatment guidelines based on historical data for the patient or other patients in similar conditions. For example, there may have been a recent successful treatment of a patient with a particular brain state using a specific treatment process that can be recommended to another patient with a similar brain state detected using the real-time brain value index. The server system 100 may continue the real-time brain monitoring using the sensors 102 during treatment to assess the patient response to treatment. This assessment may be used to refine or generate treatment recommendations for the patient or other patients with similar brain states. For example, for a range of BVI values between 1 to 100: 86 to 100 can be conscious. 59 to 81 can be reassessment; and Persistent below 49 can be immediate attention.

The display device 106 may be remote from the location of the patient to enable remote monitoring of the real-time brain state of the patient, such as in the community or geographically remote and underserviced regions. The display device 106 may also be local to the patient or there may be both a remote display device 106 and local display device 106. For example, the server system 100 may generate an alert to call for a secondary opinion to review and monitor the patient by an additional remote display device 106. As another example, server system 100 may use a remote display device 106 that automatically generates and displays alerts in response to detecting specific real-time brain states, such as building anxiety, a seizure, or building epileptic spasms and hypsarrhythmia events. The server system 100 may transmit alert notifications for the generated alerts.

Figure 2:
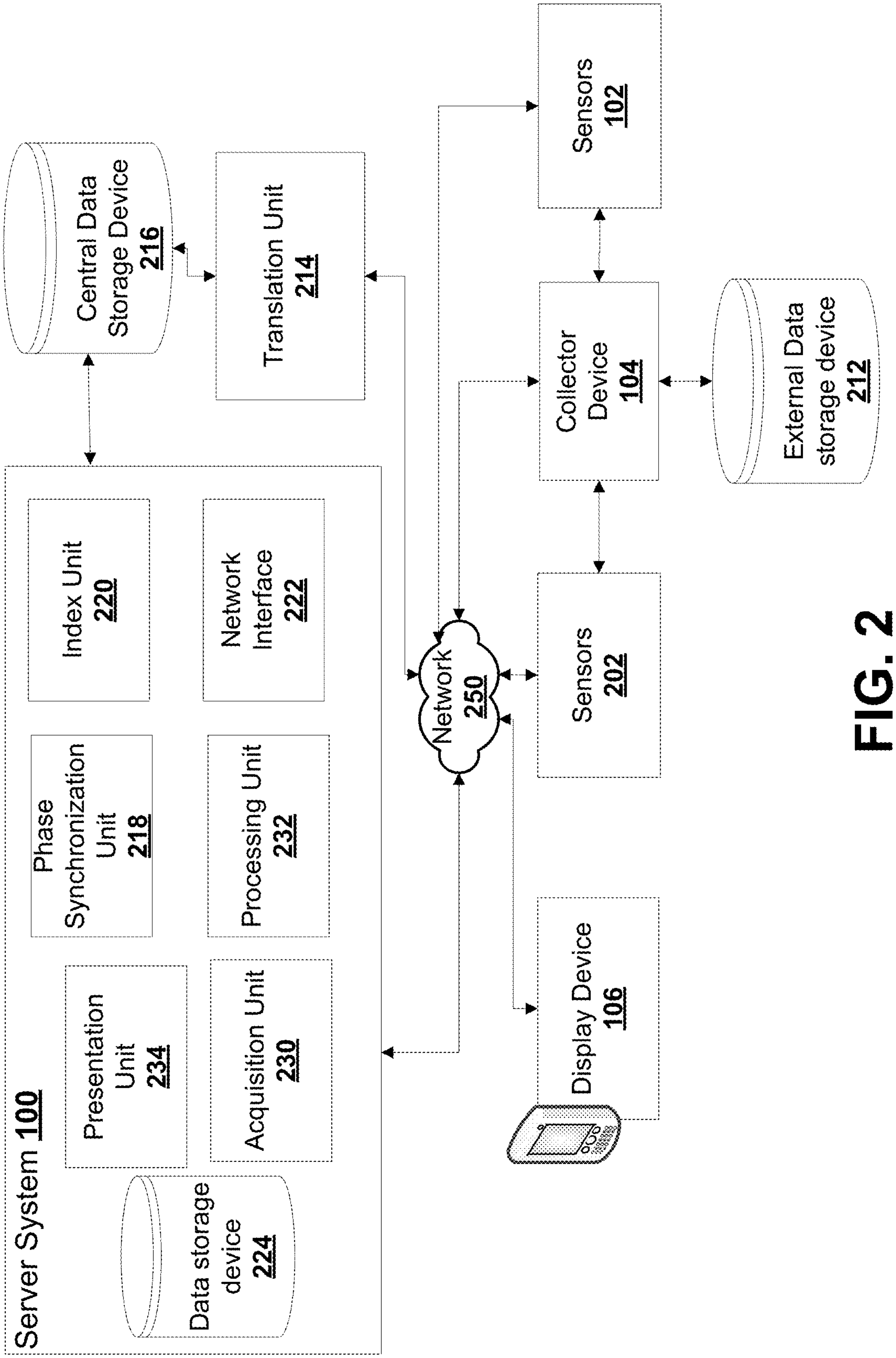
FIG. 2 is a diagram of a system for real-time brain monitoring according to some embodiments.

FIG. 2 shows another example system for real-time brain monitoring. Server system 100 may include a network interface 222 to receive sensor data (e.g. brainwave data) from sensors 102 over network 250. As an illustrative example, server system 100 may couple to multiple sets of sensors 102 for real-time brain monitoring of multiple patients.

Acquisition unit 230 receives raw sensor data from sensors 102. In some embodiments, acquisition unit 230 receives raw sensor data (including brainwave data, EEG data) data from sensors 102 in real-time or near real-time. Acquisition unit 230 saves acquired sensor data into the data file. The sensor data can be time coded and linked to a patient identifier. In simulation mode, acquisition unit 230 is configured to play back acquired EEG data from data file as a visual representation of the EEG data on display device 106. The acquisition unit 230 is configured to play back sensor data acquired from different sensors 102 from tab delimited data files.

Figure 26:
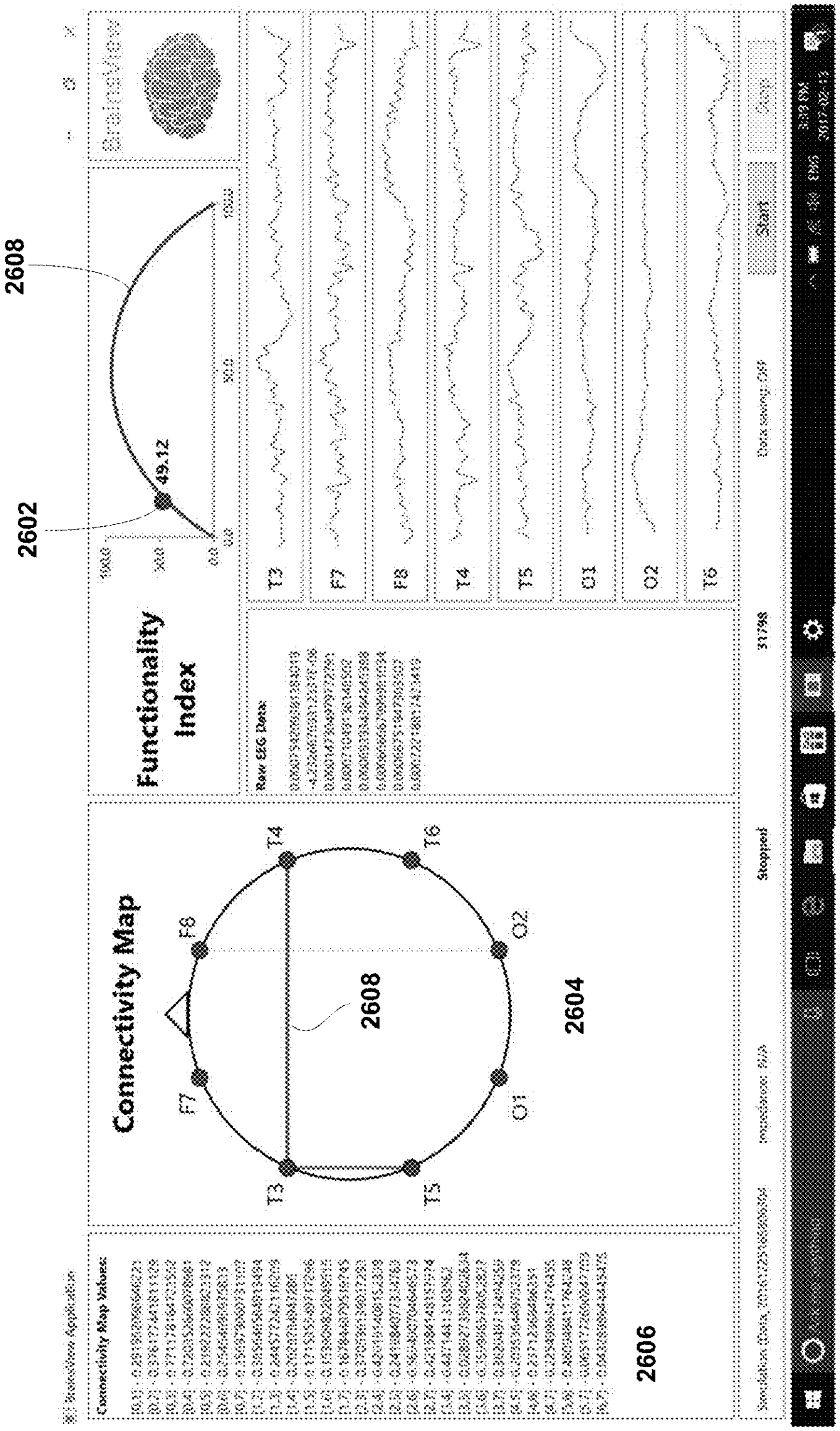
FIG. 26 is an example interface with visual representations as described herein.

Processing unit 232 interacts with phase synchronization unit 218 and index unit 220 to transform raw sensor data to generate and update connectivity matrix data (and connectivity map) and brain value index data. For example, the screenshot of interface 2600 shown in FIG. 26 can relate to a patient with concussion and The Connectivity Map Values 2606 (extreme left hand side panel), show the phase synchrony value for each of the 28 channel pairs as lines with different point thickness. The top one (0,1) shows a value of 0.29, for example. This value represents the connectivity between channel 0 (T3) and channel 1 (F7). As this value is below the example 0.45 threshold, it does not appear on the Connectivity Map 2604 to the right of the values. In contrast, the pairing of 0 and 3 (T4) [third pairing from the top] shows a value of 0.77 and it is shown on the connectivity map as a dark grey line 2608 of 2 point thickness. The Functionality Index is then calculated as previously described, with each channel pair evaluated as being below (assigned "0") or above (assigned "1") the threshold. At this instant 22 of the 28 pairs have a value below the 0.45 threshold and 6 pairs have a value above. These values are updated every second and displayed as EEG waveforms, integer values, Connectivity Map 2604 and Functionality Index graphs (with BVI marker 2602). The functional networks within the brain thus show a low entropy value which is represented by the 49 on the left side of the inverted "U" curve 2608, corresponding with fewer connections.

Presentation unit 234 generates visual representations of the brain value index, sensor data, and connectivity matrix or map on interface of display device 106. Presentation unit 234 processes control commands to update the visual representations and control sensors 102 for capturing brainwave data. For example, presentation unit 234 interacts with display device 106 or sensors 102 to implement device control commands (e.g. start/stop) and determine device statuses. Presentation unit 234 generates visual representations for raw EEG data visualization, connectivity map visualization, and brain value index visualization on interface of display device 106.

Each set of sensor data from sensors 102 may be tagged with a patient identifier to distinguish between sensor data captured from different patients. The sensor data from sensors 102 may be tagged with a time identifier (e.g. time codes) to distinguish between sessions of sensor data from the same patient. In some example embodiments, sensors 102 may provide data directly to server system 100. In some example embodiments, sensors 102 may provide data indirectly to server system 100 via collector device 104. Collector device 104 may couple to one or more sets of sensors 102 for pre-processing of the raw sensor data and provide the pre-processed sensor data or brainwave data to the server system 100. Collector device 104 may couple to a local, external data storage device 212 to store the pre-processed sensor data or brainwave data. Display device 106 may couple to sensors 102, collector device 104 and server system 100 to display visual representations of the raw sensor data, pre-processed sensor data, or brain value index data for the real-time brain monitoring and treatment guidance as part of a graphical user interface of display device 106, for example.

Server system 100 may also couple to central data storage device 216 to provide data for the real-time brain monitoring and receive other aggregated brainwave data (from e.g. cloud server) for machine learning and refinement of the process for real-time brain monitoring. For example, central data storage device 216 may provide a data repository of historical brainwave data collected from the same patient or other patients which may be used as part of the process for real-time brain monitoring. The central data storage device 216 may also store raw sensor data (from sensors 102, 202) and pre-processed sensor data (from collector device 104) to provide a central repository of all data for system 100.

A translation unit 214 may implement translation, re-formatting or processing of raw sensor data (from sensors 102, 202) and pre-processed sensor data (from collector device 104) for storage. The central data storage device 216 may serve one health care facility or multiple health care facilities and may receive data from multiple server systems 100, sensors 102 and collector devices 104. The central data storage device 216 may provide a big data platform for machine learning and correlation detection for treatment guidance. The central data storage device 216 may provide data storage for review of individual patient trajectories. In some example embodiments, the central data storage device 216 may provide data storage for multiple patients. The central data storage device 216 may implement big data processing using k-means clustering and related classification techniques and state space representation.

Server system 100 may also include various functional hardware components for real-time brain monitoring. For example, server system 100 may include a phase synchronization unit 218 configured to calculate a connectivity matrix and an index unit 220 configured to compute the real-time, brain state index and treatment guidance as described herein. The server system 100 may also include local memory or data storage device 224. The network interface 222 may transmit control commands to display device 106 to generate and update its interface. The network interface 22 may also transmit control commands to actuate treatment related machines to trigger treatment or intervention for patient based on the computed brain state index.

Figure 3:
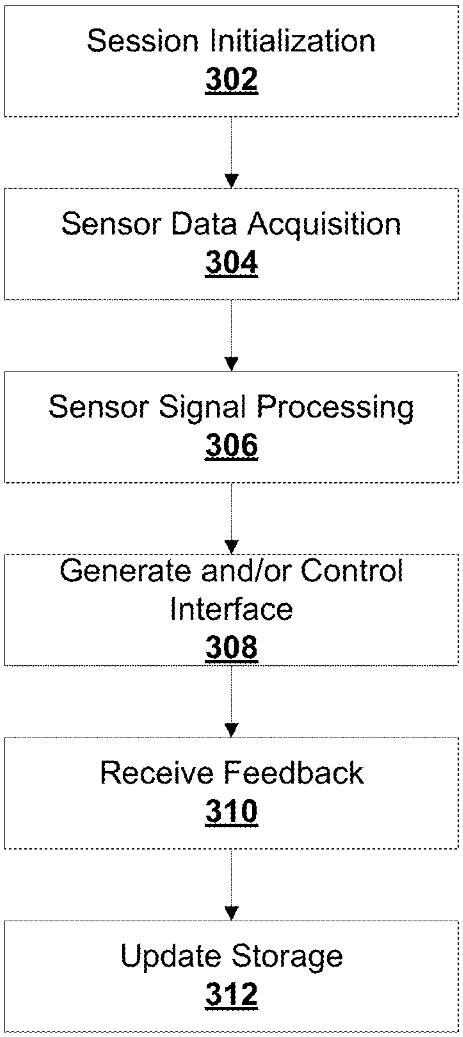
FIG. 3 is a flow chart diagram of a process for real-time brain monitoring according to some embodiments.

FIG. 3 shows a flow chart of a process for real-time brain monitoring.

At 302, the server system 100 may trigger a real-time brain monitoring session initialization process. The initialization process may involve calibration of sensors 102, 202 and collector device 104. For the initialization process, the server system 100 may calculate all variables that do not change throughout the session. Specifically, this session initialization step is performed to optimize real-time signal processing by pre-computing otherwise redundant, ongoing computations. This step also sets up all local memory and resource allocation for real-time signal processing.

At 304, the server system 100 may trigger a sensor acquisition process (e.g. EEG or brainwave data acquisition) to acquire data from sensors 102 or collector device 104. The sensor acquisition process may be implemented by a combination of one or more of sensors 102 collector device 104 and server system 100. As an illustrative example embodiment, sensors 102 may include a wearable device or headset with eight to twelve dry electrodes to acquire raw sensor data from a patient along with one or more electrodes to acquire reference data. For an example prototype design, in addition to ease of electrode application, the sensor placement captures data from brain regions that provide important information on normal function and pathology. At minimum, the 8 electrodes capture data from the frontal lobes (F7 and F8); anterior temporal (T3 and T4) which include memory regions, posterior temporal (T5 and T6) which includes part of the parietal lobe that integrates information and the occipital region (O1 and O2) that contains the visual cortex. This is an example montage. The sensors 102 may include electrodes to capture EEG data and the sensor acquisition process may involve EEG analog signal acquisition from the headset. Further, the sensor acquisition process may involve EEG analog signal pre-amplification in headset and EEG analog to digital signal conversion. The sensor acquisition process may involve transfer of EEG digital signal to collector device 104 and server system 100 for processing. For example, the sensors 102, 202 may be wireless, non-contact EEG and EKG electrodes.

In some embodiments, sensors 102 include electrocardiogram (EKG) sensors to capture EKG data. Acquisition of EEG and EKG data can be followed by calculating BVI values and heart rate or blood pressure using the signal data of each signal respectively. The relationship between the two values are represented in state space, where a graph of optimal physiological functioning is seen in FIG. 10. Using 2 physiological indicators, the relationship between the Brain Value Index (y axis) and the heart rate entropy (x axis). In the non-anxiety or non-epileptic spasms and hypsarrhythmia state, the Functionality Index and heart rate values would expected to be variable representing the baseline state. A patient with anxiety or epileptic spasms and hypsarrhythmia would experience a change in the values and a decrease in the variability of 1 or both values.

The state space reconstruction in the above graphs depict the relationship between the FI—Functionality Index (y axis) and heart rate (x axis) for an equivalent 65 second time period for baseline functioning (top panel) and during the panic event (bottom panel). The variance of the heart rate is statistically significantly different between the baseline state (15.5) and the panic state (2.5).

Figure 8:
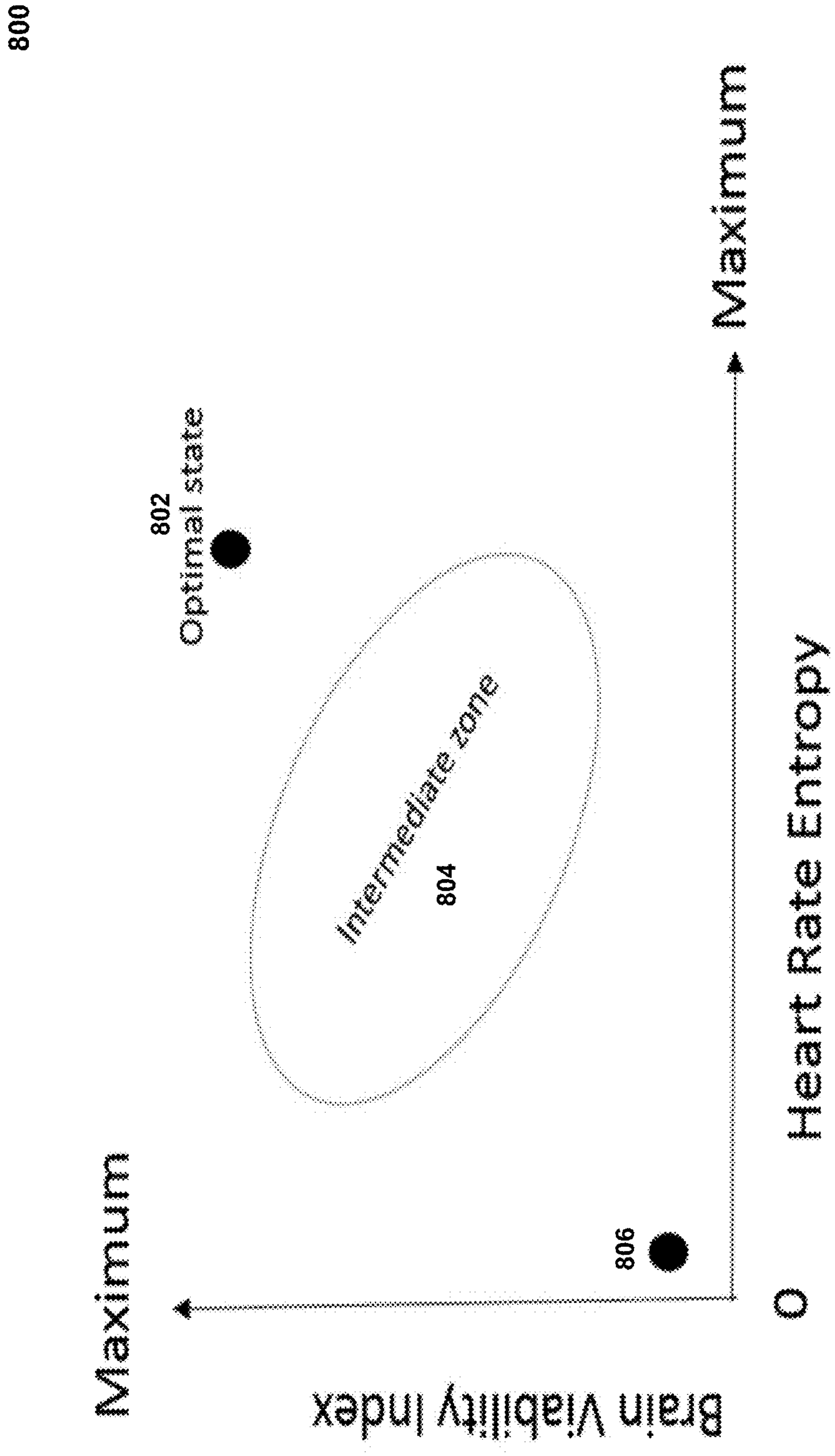
FIG. 8 is a graph of Brain Value Index and Heart Rate Entropy.

Referring to FIG. 8, there is shown a graph for BVI values and heart rate entropy. In some embodiments, sensors 102 include electrocardiogram (EKG) sensors to capture EKG data. Acquisition of EEG and EKG data can be followed by calculating BVI values and heart rate entropy using the signal data of each signal respectively. The relationship between the two values is represented in state space, where a graph of optimal physiological functioning is seen in FIG. 8. Using 2 physiological indicators, the relationship between the Brain Value Index (y axis) and the heart rate entropy (x axis). In a normally functioning, fully conscious adult, the Brain Value Index and heart rate entropy values can be maximal and be represented in the upper right hand corner labeled "Optimal state" 802. A patient with either cardiac or neurological pathology or adverse events would experience a change in the values and a decrease in 1 or both values. These values would be seen in the "Intermediate zone" 804 and would trigger the clinician to further evaluate the patient and treat if required. Values in the lower left hand corner near zero (marker 806) would indicate a patient approaching death.

Figure 27:
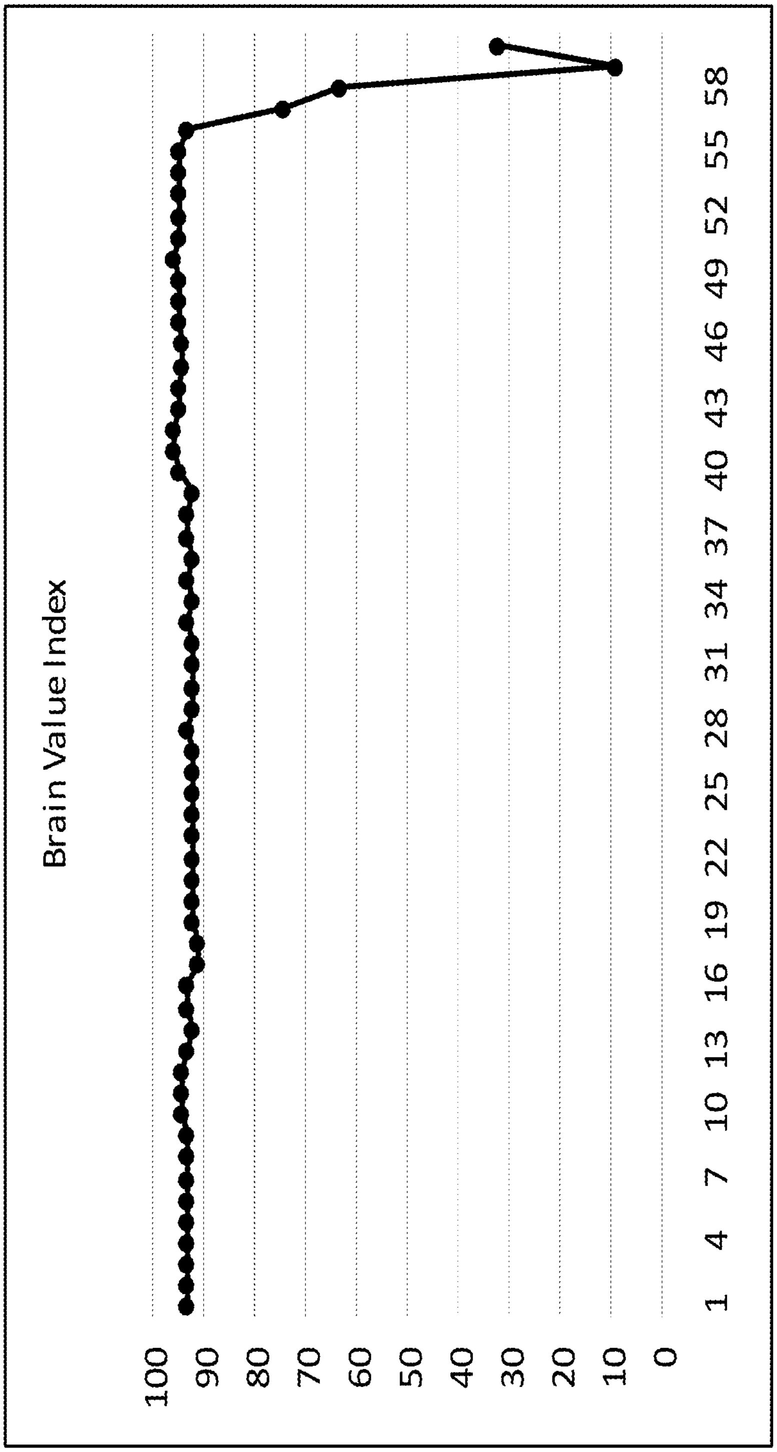
FIG. 27 is an example graph relating to a patient as described herein.

A patient case study is provided as a further example with reference to the graph 2700 shown in FIG. 27 for Respiratory arrest, SUDEP and State Space. For the example a 20 year old girl who can be video monitored for seizures, with intracortical electrodes has a change in brain function with EEG slowing and severe attenuation of waveforms, prior to a respiratory arrest. This event was deemed to be an interrupted SUDEP (Sudden Unexplained Death in EpilePsy). She was successfully resuscitated. For this patient, her Functionality Index (Brain Value Index) can evaluated in conjunction with her heart rate pre and post arrest. The graph 2700 shows the time series of the Brain Value Indices for almost 60 seconds of recording prior to the respiratory arrest (EEG recording was interrupted during resuscitation. The patient was awake and talking during this time period until her brain waves attenuated and she stopped breathing. The video had showed that the respiratory arrest was recognized by the bedside nurse and resuscitation activated 30 seconds after the arrest occurred.

Figure 28:
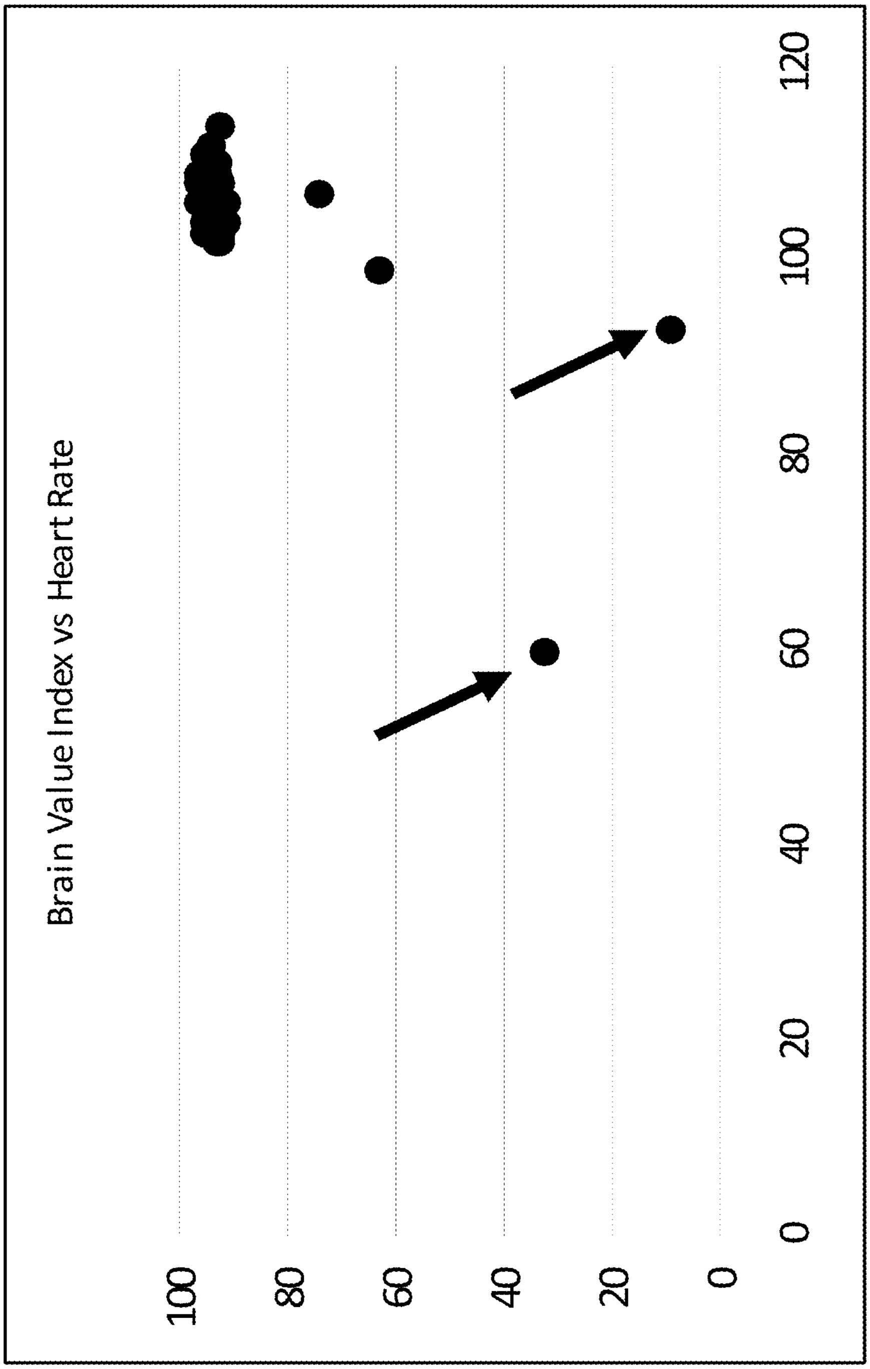
FIG. 28 is an example graph comparing brain value index values to heart rate data as described herein.
Figure 29:
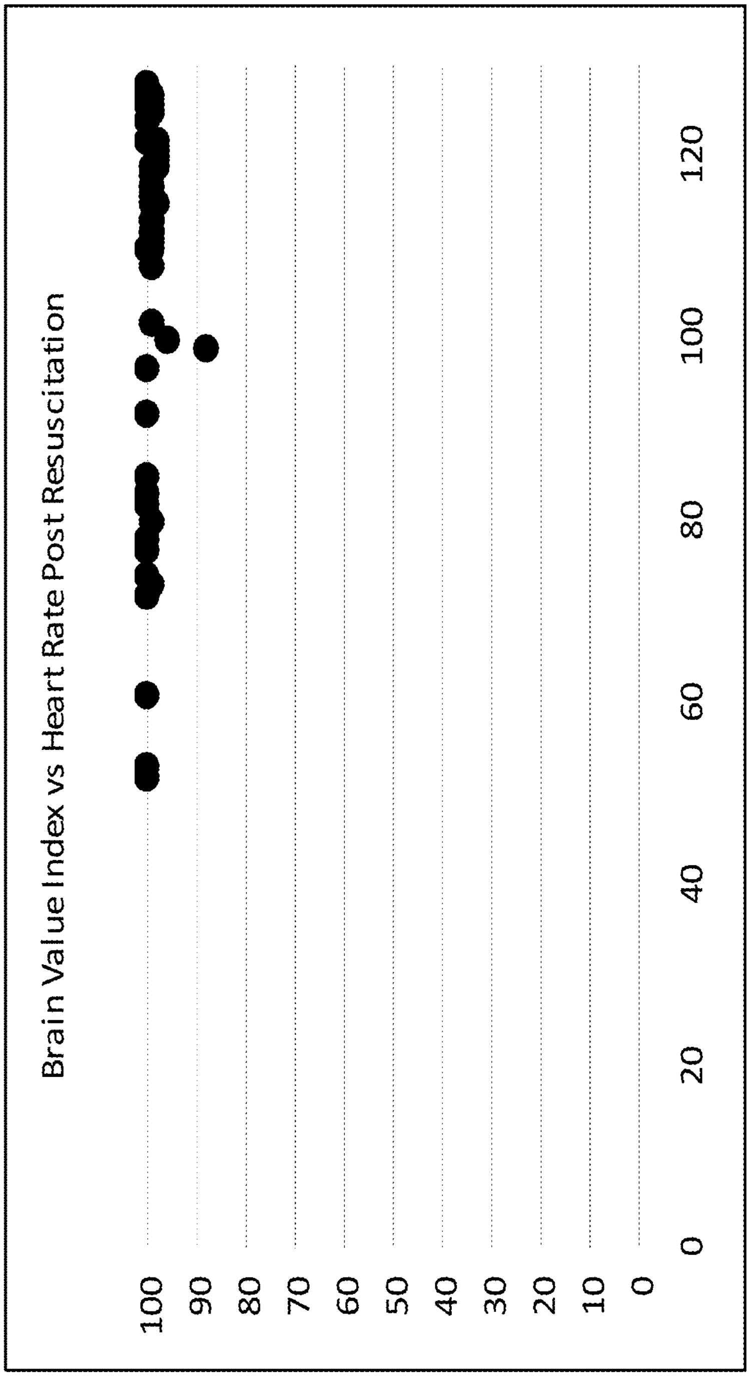
FIG. 29 is an example graph comparing brain value index values to heart rate data as described herein.

FIG. 28 shows a graph 2880 of state space reconstruction that depicts the relationship between the Brain Value index (y axis) and heart rate (x axis) for the same 59 second time period as in the graph 2700 of FIG. 27. The cluster of points in the upper right hand corner of the graph, reflect the patient's awake and conscious state. The arrows highlight the change with a decrease in Brain Value Index and heart rate as the patient loses consciousness and stops breathing. The graph of FIG. 29 is post resuscitation when the patient has regained consciousness and is alert and talking.

Referring back to FIG. 3, at 306, the server system 100 may implement real-time signal processing. In example embodiments, the real-time sensor processing may be implemented by a combination of one or more of sensors 102, 202, collector device 104 and server system 100. Real-time processing may be achieved by implementing data analysis processes in a high-performance programming language such as C, C++, or Java. Other techniques to improve real-time processing speeds include the session initialization step 302.

As noted, collector device 104 may pre-process the raw brainwave signal data for noise filtering, artifact reduction, reduction of volume conduction and reference electrode removal, for example. In other embodiments, sensors 102 may integrate with hardware chip on headsets to implement pre-processing on acquisition of the raw signal data. In further embodiments, the server system 100 may pre-process the raw sensor data instead of or in addition to collector device 104. Please provide any further details on the pre-processing for the brainwave signals.

Server system 100 may process the brainwave signal data to generate a connectivity matrix. Server system 100 may define a time period of a sliding window. As an illustrative example, the server system 100 may define a 1 second sliding window. The server system 100 (e.g. phase synchronization unit 218) may implement a Hilbert transform to calculate the instantaneous angle of a channel. This may be followed by a phase synchrony calculation (R) for each instantaneous angle channel. The server system 100 computes a connectivity matrix (S) (entries are the R values for each pair combination) used to generate the brain state index. As an illustrative example, server system 100 may calculate a Boolean connectivity matrix (B) where the entries are, 0 if the corresponding R index is lower than an R threshold, and 1 if higher. The server system 100 may calculate a threshold from the average of R indices of normal adults with eyes open. Connected channels may be defined as entries of B=1. It can be helpful to include a few examples of the connectivity matrix.

The server system 100 (e.g. index unit 220) computes a Brain Value Index calculation (BVI) or Functionality Index or "normalized entropy" using a total number of possible connections. Phase synchronization is calculated for each pair of channels and a "connectivity" matrix S is obtained, whose entries are the average values of the synchrony index for each pair combination. From this one, a Boolean connectivity matrix B is calculated, with 0 entry if the corresponding synchrony index is lower than a threshold, and 1 if higher. We define two channels "connected" if the corresponding entry in matrix B is 1. Then we use the combinations of connected channels as a 'complexity' measure. The total number of possible pairs of channels given a specific channel montage is $N=Nc!/2!(Nc-2)!$ where Nc is the total number of channels in the recording system, normally 144-146 in case of MEG sensors, between 19 and 28 in case of scalp EEG and 8 channels in our prototype. The channel numbers are specified, below, in each case. For instance, in our MEG recordings we have Nc=144, thus N=10296 possible pairs of connected sensors are obtained. For each subject we calculate p (the number of connected pairs of channels) in the different behavioural stages, using the threshold of the synchrony index of 0.45 based on the average phase synchronization of normal adults in the alert state with eyes open, and estimate the number of possible combinations of those p pairs, C, using the binomial coefficient again: $C=N!/p!(N-p)!$ All these calculations represent the relatively simple combinatorial problem we are trying to solve: given a maximum total of N pairs of connected signals, in how many ways our experimental observation of p connected pairs (that is, the number of 1's in matrix B) can be arranged. The entropy and Lempel-Ziv complexity associated with those p values are then computed. In the final step, each entropy value is divided by the maximal entropy value and then multiplied by 100. In the example 8 channel prototype there are 14 possible values of the Brain Value Index (rounded to whole numbers): 22, 37, 49, 59, 67, 74, 81, 84, 90, 94, 96, 98, 99, 100.

At 308, the server system 100 (e.g. index unit 220) computes output data to control the display device 106 to update the interface with interface elements to provide a visual representation of the output data. The server system 100 continuously transmits the BVI for real-time monitoring using a controlled graphical display.

At 310, the server system 100 may receive feedback from display device 106 or other computing device to refine the processing to create individual thresholds or population based thresholds.

At 312, the server system 100 uploads the data to one or more storage platforms (e.g. central data storage device 216, local data storage device 224, external data storage device 212).

Figure 4:
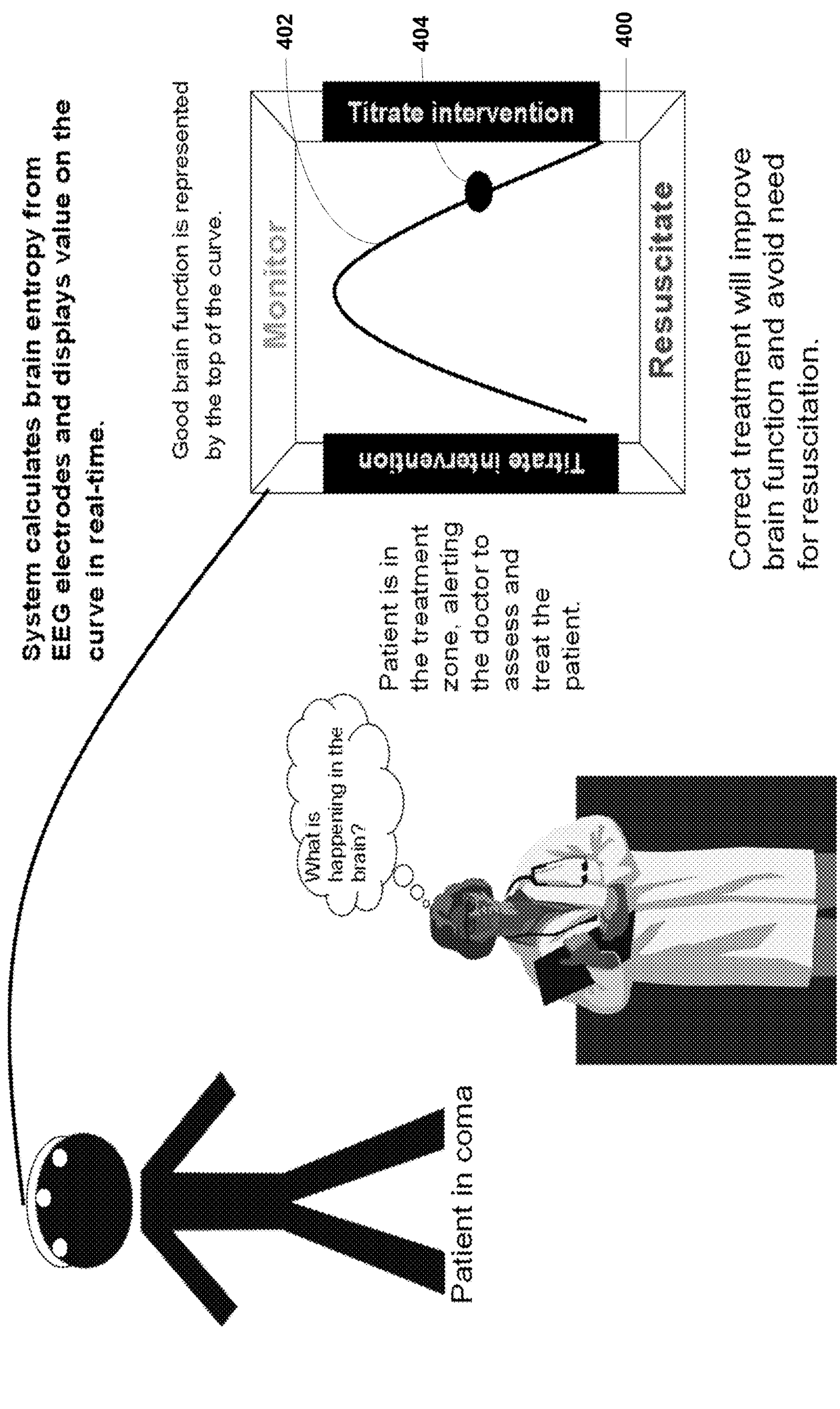
FIG. 4 is an example interface with a visual representation for real-time brain monitoring according to some embodiments.
Figure 5A:
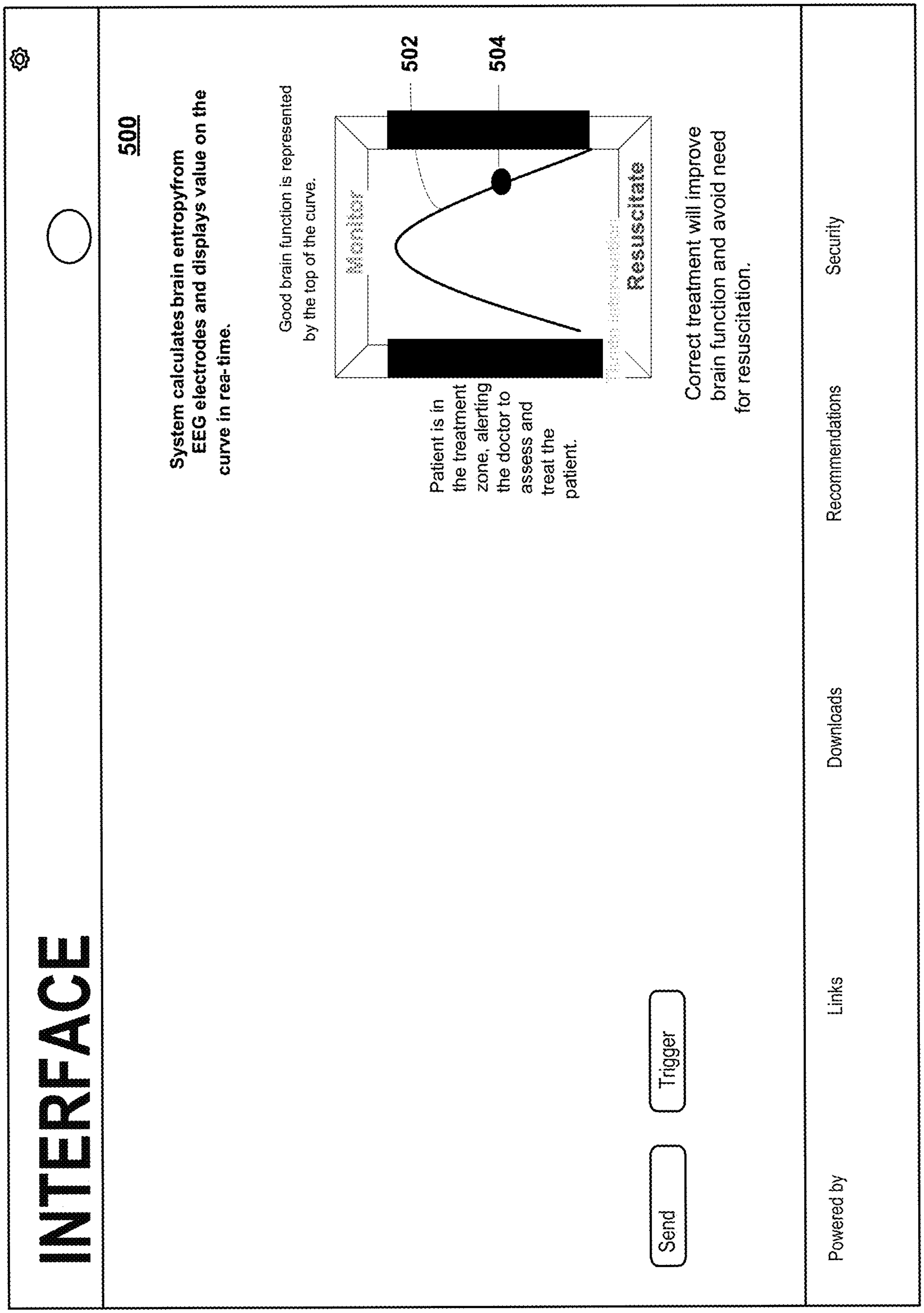
FIGS. 5A and 5B show example interfaces with a visual representation for real-time brain monitoring according to some embodiments.
Figure 5B:
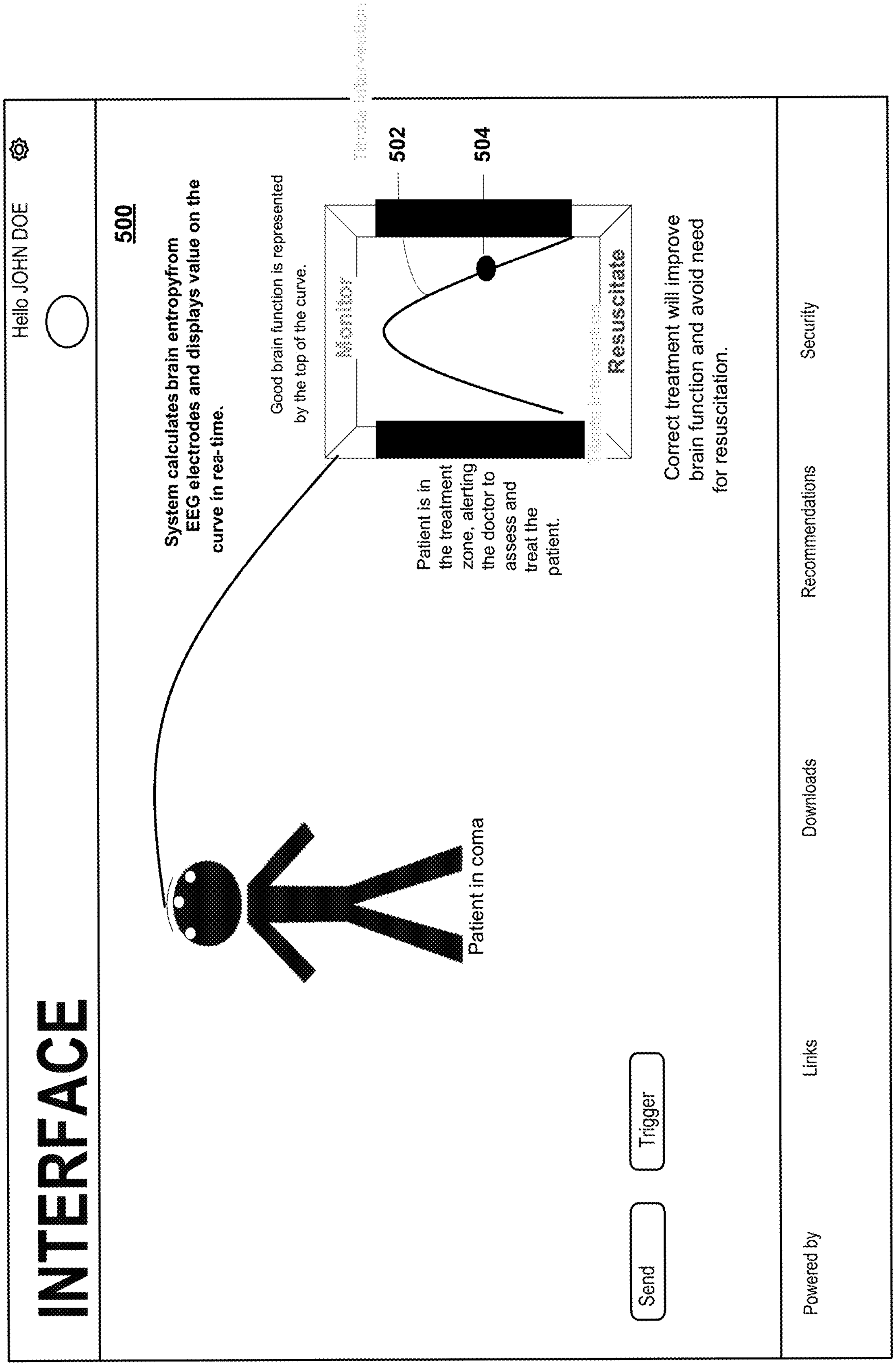

FIGS. 4, 5A and 5B show example interfaces 400, 500 with interface elements to provide a visual representation of real-time brain state monitoring according to some embodiments. As shown in the graph curve, a marker 402, 502 reflective of the real-time brain value index (brain state) may move along the curve in real-time as a visual representation of the processed brainwave signals. For different brain states, the server system 100 may define with preset alarm threshold values or ranges for the processed brainwave signals for the patient. The brain states may correspond to different treatment guides, such as monitor (Brain Value Index 86 to 100), resuscitate (Brain Value Index<59, treatment, and intervention. The range for the 2 latter is 59 to 81 and is pathology specific, i.e. a Brain Value Index of 59 in a patient with epilepsy could trigger review of anticonvulsant medication. In this example, the peak of the curve and region proximate to the peak of the curve may correspond to a brain state for monitoring the patient. In some embodiments, the level of anxiety may correspond to different treatment guides, such as deep breathing or relaxation techniques, (Functionality Index 75-86), or medication treatment (Functionality Index<75). In some embodiments, the number of epileptic spasms and hypsarrhythmia patterns, may correspond to different treatment guides, such as valproic acid (Functionality Index 75-86), or alternative medication treatment, vigabatrin (Functionality Index<75). If the real-time processed brainwave signal changes this may trigger the marker 402, 502 to move along the curve and trigger an alert or intervention such as treatment, resuscitate 404, 504 or prepare for organ donation.

Control indicia 406 on interface 400 (or a separate control device) may trigger treatment to patient such as by triggering stimulation to the brain of the patient. The interface 400 may overlay historical data about the patient or another patient with a similar condition as additional visual representations. Transmission indicia 408 on interface 400 (or a separate device) may trigger transmission of feedback data regarding the patient which may be used to refine the processing rules for machine learning.

FIG. 4 provides an illustrative example, where the inverted U-shape curve 410 with a sliding marker 402 provides a visual representation which represents the normalized entropy (Functionality Index, Brain Value Index) value of 0 to 100 (y-axis) versus the number of possible channel pair combinations (x-axis). With the 8 channels of our prototype device, the x axis will be 28 possible channel pairs. The normalized entropy calculation has been described and the value reflects the amount of information processing by the cortical networks of the brain, where 100 is the maximum information processed by an conscious, normally functioning adult brain. This curve may be calculated on a session-by-session basis (at the session initialization 302, dependent on the number of electrodes) and may be constant throughout that session. The marker 402 represents the real-time normalized entropy and real-time number connected pairs of channels as the real-time brain state index. As an example, the sliding marker 402 can be in 1 of 3 zones: (1) top of the curve—good, direct staff to monitor maintain current treatment, (2) mid slope—review patient and re-evaluate treatment, (3) bottom of curve—urgent intervention or if patient is being monitored as an organ donor, activate the organ retrieval protocol.

The following provides further illustrative example processes for electrophysiological recordings and real-time brain state monitoring. For an example experiment, recordings may be analysed from ten (10) patients. There may be 3 types of recordings: three patients with magnetoencephalographic (MEG); one patient with intracerebral electrode recordings; and six (6) with both intracerebral and scalp electroencephalographic (EEG) recordings. The MEG recordings may be obtained by sensors 102 on one patient with primary generalized epilepsy and absence seizures, in one patient with symptomatic generalized epilepsy and tonic motor seizures, and in one patient with frontal lobe epilepsy and tonic motor seizures. The intracranial EEG recordings may be obtained from sensors 102 patients with medically refractory temporal lobe epilepsy as part of their routine clinical pre-surgical investigations. MEG recording sensors 102 can cover the whole cerebral cortex, whereas intracranial EEG electrodes may be positioned bilaterally in the amygdala and hippocampal structures of the temporal lobes. The details of the acquisition varied from patient to patient and may be taken into consideration for the data analysis. The acquisition rate or sampling frequency may vary from 200 to 625 Hz. The sampling frequency is addressed in the algorithm used to calculate the phase synchrony. The prototype device has a default setting of 250 Hz acquisition rate. The duration of the recordings may vary from 2 minutes to 55 minutes. The sleep data may be 2-4 minutes in length. This is an example experiment for illustration only.

The pre-processed data may be from sensors 102 on the scalp EEGs which may be processed using a Laplacian to avoid the potential effects of the reference electrode on synchronization, using the current source density (CSD) algorithm. The reference electrode may be placed on the scalp or on one or both ears (linked ears) may be used. The prototype device employs the right ear as the standard reference electrode. Analysis may involve computing the phase synchrony index (e.g. brain value index) by estimating phase differences between two signals from the instantaneous phases extracted using the analytic signal concept via the Hilbert transform. Several central frequencies, ranging from 3 to 30 Hz may be chosen with a bandpass of 2 Hz on either side. In the prototype device the default setting is 3 Hz. The 3 Hz is in the delta bandwidth and with the ±2 Hz range, encompasses 1 Hz at the lower end, which is the only frequency generated by the cortex to 5 Hz at the upper end which is in the theta range. The phase synchrony index (R) may be calculated using a 1-second running window, obtained from the phase differences using the mean phase coherence statistic which is a measure of phase locking and is defined as $R=\langle e^{(i\Delta\theta)}\rangle$ where $\Delta\theta$ is the phase difference between two signals.

Phase synchronization is calculated for each pair of channels and a connectivity matrix S is obtained, whose entries are the average values of the synchrony index for each pair combination. A Boolean connectivity matrix B is calculated, with 0 entry if the corresponding synchrony index is lower than a threshold, and 1 if higher. The threshold has been previously defined as 0.45 based on the mean phase synchronization value at 3 Hz of normal control subjects in the awake state with eyes open. Two channels may be "connected" if the corresponding entry in matrix B is 1. The combinations of connected channels may provide a 'complexity' measure. The total number of possible connections given a specific channel montage is $N=Nc!/P!(Nc-P)!$ where Nc is the total number of channels in an example recording system and p is the number of connected channels in an example recording system. This may be 144-146 in case of MEG sensors 102, and between 19 and 28 in case of scalp EEG sensors 102. The channel numbers are specified, below, in each case. For instance, in MEG recordings we have Nc=144, thus N=10296 possible pairs of connected sensors 102 are obtained. For each subject we calculate p (the number of connected pairs of channels) in the different behavioural stages, using the threshold of the synchrony index (which varies for each subject, but whose average is 0.45) method aforementioned. The server system 100 estimates the number of possible combinations of those p pairs, C, using the binomial coefficient again: $C=N!/p!(N-p)!$ All these calculations represent the combinatorial problem we are trying to solve: given a maximum total of N pairs of connected signals, in how many ways our experimental observation of p connected pairs (that is, the number of 1's in matrix B) can be arranged. We then compute the entropy and the Lempel-Ziv complexity associated with those p values.

It must be noted that, while the words synchrony and connectivity may be used synonymously, in reality phase synchrony analysis reveals a correlation between the phases of the oscillations between two signals. Connectivity depends on several other factors, such as for example:

Length of epoch. The longer the time epoch is that is being analyzed, generally the lower the phase synchrony value. Two electrodes may have a very high phase synchrony index (e.g. >0.9) for 1 to 2 seconds as in the case of the patient with absence epilepsy, during the seizure event. Connectivity in the same electrode pair in the same patient may show a phase synchrony value of 0.6 over 10 seconds if non seizure events are included. Given that neuronal and network connections in the brain occur at the millisecond time scale, high phase synchrony values for 10 seconds would be considered pathological and seen in prolonged seizure events.

Channel connectivity versus whole brain connectivity. Phase synchrony is always calculated between 2 electrodes for the specified time epoch. A channel pair (e.g. T3 and T4) may have a high phase synchrony value (>0.9). If hypothetically, this is the only channel pair out of the possible pairs from the 8 electrodes [8!/(2!X6!)=28] that shows any connectivity, then both the channel pair connectivity and the whole brain connectivity are the same.

Frequency of interest. The prototype analyzes the 3 Hz bandwidth, ±2 Hz. If the same algorithm used to calculate phase synchrony at 3 Hz is used to calculate that at 15 Hz, without altering the algorithm, the resultant value will be falsely lowered.

In some example embodiments, phase relations may represent, at least, some aspect of a functional connectivity. Hence, in order to evaluate interactions ("connections"), server system 100 may take each sensor 102 as one "unit", and define a pair of sensors 102 (signals) "connected" if the phase synchrony index is larger than a threshold. The threshold is determined by server system 100 for each individual, and is the average synchrony index in the 'awake eyes-open' condition, when the individual is alert and processing the sensorium in a regular fashion. An example for a control population average can be 0.45 for the threshold. This enables server 100 to filter the complex data to generate a clear visual representation on the interface.

The data may include MEG, scalp EEG, intracerebral recordings, or other types of recordings. While there may be reference to signal level processing, the MEG and scalp EEG sensors 102 record cortical activity and thus throughout the text the terms brainwave signals or brain areas/networks may be synonymous. Server system 100 may consider the global states in addition to the specific pattern of connectivity among brain sources.

As an illustration, server system 100 may estimate the number of possible pairwise connections between the recorded brain signals from magnetoencephalography (MEG), intracranial electrodes and scalp electroencephalographic (EEG) recordings. In experiments we were limited to pairwise combinations of the signals because of the manner in which synchrony is computed, between two signals, as we use phase synchronization as the means to determine "connectivity" between two signals. The results obtained with recordings under conscious states are compared with those taken during unconscious states, which included sleep (all the stages) and seizures.

There may be a similar trend in the case of sleep. In some examples, during wakefulness the entropy is closer to the maximum of the curve, whereas the deeper the sleep stage, the more distant to the maximum the values are. The entropy during REM stages is very close, in most cases, to the normal, alert state. It is worth noting too that in recordings taken when the subjects had their eyes closed, the entropy may be much lower than during the eyes open condition, and sometimes it is as low as the SWS 3-4 (the deepest slow-wave sleep stage).

The server system 100 may consider features of brain organization that allow for sufficient sensory stimuli processing to support the conscious, awake state. The greater number of possible configurations of interactions between brain networks is associated with alert states, and represented high entropy. In contrast, lower entropy associated with fewer combinations of connections, is characteristic of either unconscious states or fewer input states (e.g. eyes closed, anxiety, seizures, epileptic spasms and hypsarrhythmia, etc.). This observation reflects a general organising principle. The emergent property of this collective level of description is that consciousness is a manifestation of the second principle of thermodynamics. The second principle of thermodynamics states that in isolated systems, entropy never decreases; that is, the system will approach equilibrium with maximum entropy. However, in systems that exchange matter/energy, like the brain in its activity, the S may decrease. Nevertheless considering the whole system, the non-isolated plus the environment, the S still will never decrease. The brain is an open system and thus what we observe is that, while it tends to reach equilibrium with max S, it remains close to it (in fully alert states) but does not achieve complete equilibrium because of the exchanges of energy/matter with the surroundings (e.g. heat loss from metabolism). Also, in statistical thermodynamics, entropy is a measure of the number of microscopic configurations that a thermodynamic system can have when in a state as specified by certain macroscopic variables. When evaluating entropy in the brain, entropy can be seen as the information content in the functional network. The state of alertness in the human brain can be seen as the condition in which there is maximal information within the functioning networks that give rise to the conscious state. Maximal information is thus maximal entropy. In our brain monitoring system, this maximal entropy value is reflected in the Functionality Index or Brain Value Index of 100 at the top of the curve. The concept of information being equivalent to entropy is in the Shannon definition of entropy which is equivalent to the Boltzmann/Gibbs definition in thermodynamics and there are similarities in the equations that define both information and entropy.

With the advent of Big Data and the related torrent of empirical observations emphasizing the exhaustive scrutiny of elementary biological processes, the search for organising principles that result in the emergence of biological phenomena seems more crucial than ever lest we drown in the flood of data. The server system 100 processing may capture the bounds in the global organization of a biological system to become adaptable (i.e., respond) to an environment, or, in neuroscientific terms, features of optimal brain organization (in terms of connections) that allows brains to adequately process sensory stimuli. The server system 100 may focus on the global states, and in some instances, additionally on specific patterns of connectivity between brain areas. The term 'connectivity', may refer to a correlation between phases of oscillation.

The server system 100 may consider that the number of pairwise channel combinations—that is, its interactions/connections between brain networks—occurs near the maximum of possible configurations in periods with normal alertness. This may indicate that the greater number of configurations of interactions represents the most probable distribution of energy/information resulting in conscious awareness. In the final analysis, information exchange implies energy exchange, hence we interpret Information exchange as energy redistribution.

Aspects of awareness emerge when certain levels of complexity are reached, it is then possible that the organization (complexity) needed for consciousness to arise needs the maximum number of configurations that allow for more variety of interactions between cell ensembles because this structure leads to optimal segregation and integration of information, two fundamental aspects of brain information processing.

Microstates that yield the same macrostate form an ensemble. Hence, the macrostate with higher entropy as defined, is composed of many microstates (the possible combinations of connections between diverse networks), and can be thought of as an ensemble characterised by the largest number of configurations. In neurophysiological terms, each microstate represents a different connectivity pattern and thus is associated with, in principle, different behaviours or cognitive processes. The macrostate that we find associated with wakeful normal states (e.g. eyes open) is the most probable because it has the largest entropy (largest number of combinations of connections). Hence optimal information processing seems to be the result of the most probable distribution of energy (information) among brain networks. At the same time, the ensemble of microstates associated with normal sensory processing features the most varied configurations and therefore offers the variability needed to optimally process sensory inputs. For the metastability of brain states, the states should not be too stable for efficient information processing, hence the larger the number of possible interactions, the more variability is possible. Equally, the results are consistent with the global workspace theory in that the most widespread distribution of information, the more optimal its processing. Finally, these observations relate as well to the information integrated theory, in that consciousness increases in proportion to the system's repertoire of states, thus the more combinations possible, the more states, and here we can define states as configuration of interactions.

Additionally, the results support computational and theoretical studies showing that patterns of organised activity arise from the maximization of fluctuations in synchrony and by just varying the probability of connections in neural networks, and in general highlight all proposals of the fundamental importance of fluctuations in nerve activity as the source of healthy brain dynamics. FIG. 11A shows an example interface with a visual representation providing an interface 1100 of brain connectivity (left) for different example EEG channels, a graph 1102 with a marker 1104 for the real-time brain value index (right top) or normalized entropy, and interface elements 1116 for raw EEG signals per channel (right bottom). A list of calculated brain value index values 1108 is visually represented. Stronger connections between channel pairs can be represented visually by thicker lines. The interface 1100 indicates a connectivity matrix with phase locking between channel pairs that have R index greater than 0.45. The lines are shown thicker (weighted via rules) that have higher R. Interface elements 908 show multiple raw EEG signals from different channels. This example includes 8 EEG channels: T3, F7, F8, T4, T5, O1, O2, T6. The brain index value marker 1104 ranges between 0 and 100 in this example and indicates the network entropy and how connected the brain is. Various example interfaces for graphical display will be described. The output from the EEG sensors and processing is displayed graphically for the user.

Figure 6A:
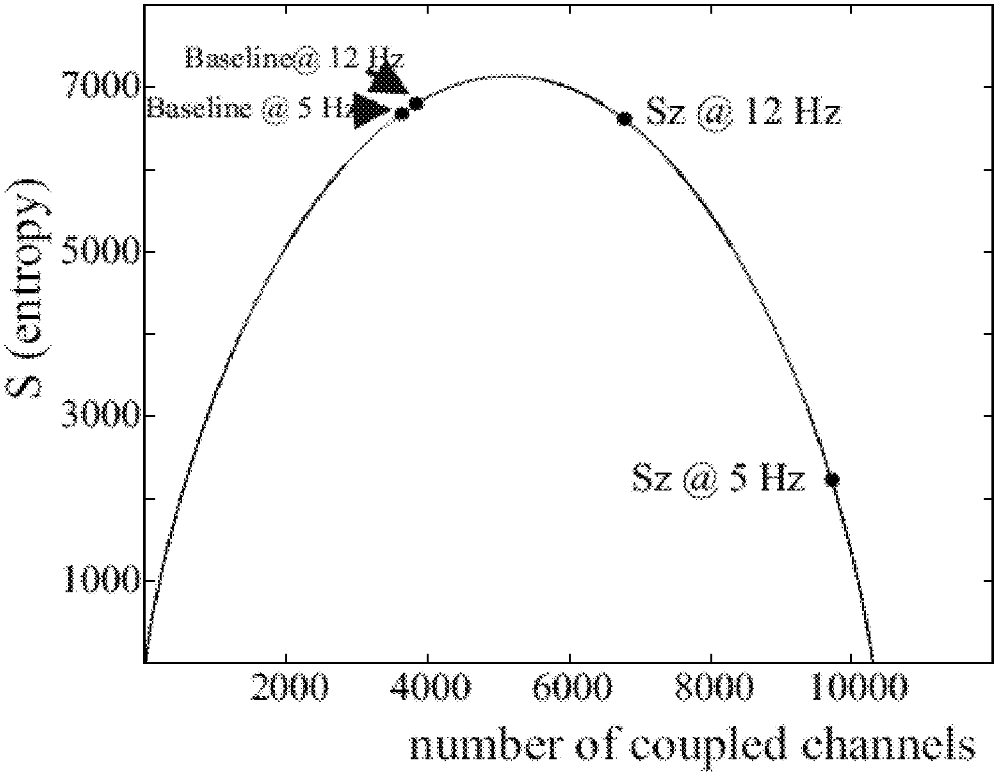
FIGS. 6A and 6B show example graphs where entropy decreases from baseline (near the top of the curve) to lower right during a seizure.
Figure 6B:
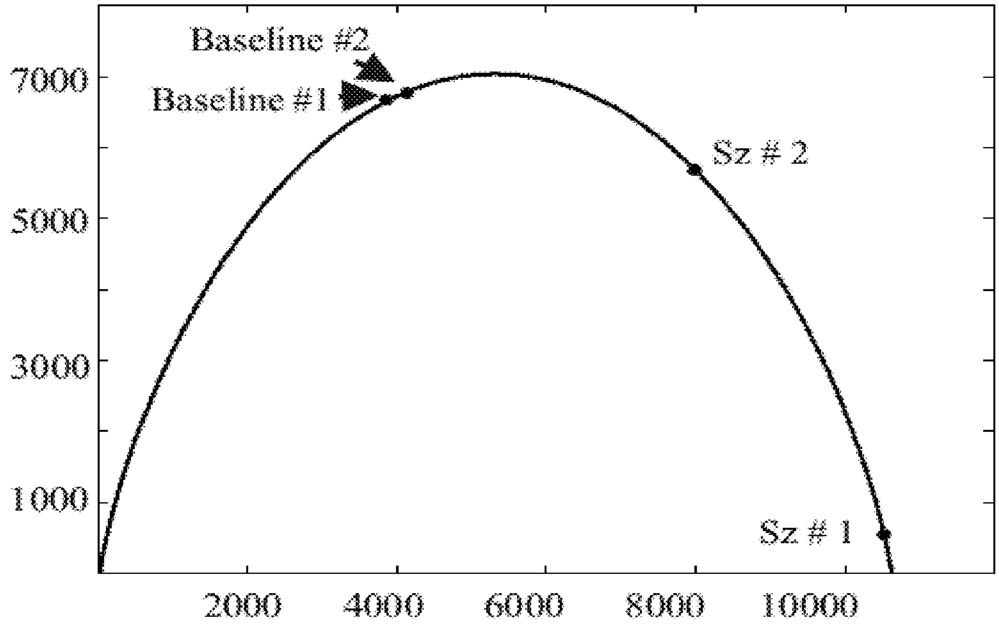

FIGS. 6A and 6B show example graphs from an experiment employing a magnetoencephalography (MEG) to measure the magnetic signal of brain electrical activity from a patient with epilepsy. The MEG uses 144 sensors (channels) to detect the magnetic output associated with brain electrical activity. The graph shows the relationship between the over 10,000 possible sensor pairs on the x axis and the resultant calculated entropy on the y axis from 0 to 7000. The resultant inverted "u"-shaped curve models the brain's information processing capacity where normal brain function exists near the top of the curve with maximal entropy in half of the number of possible sensor connections. Lower entropy values are associated with fewer connections (left hand side of the curve, where less information is processed because fewer connections are involved. This side of the curve represents more "disconnected" brain states such as sleep or brain injury, where fewer connections are available to process information. When lower entropy values are associated with a greater number of connections this indicates that less information is processed as too many connections are involved and there is less flexibility for more input. This is seen in conditions such as generalized epilepsy. In this patient entropy decreases from baseline (near the top of the curve) to lower right during a seizure (Sz). The right hand side of the curve indicates that there are more connected networks, yet less information processing as is typical of a patient during a seizure event. The patient's baseline recording is evaluated at two frequencies, 12 Hz (alpha range) and 5 Hz (theta range). The resultant entropy values are both represented on the left hand side of the curve (less connected). The entropy of the seizure event (Sz) is evaluated at the same 2 frequencies (12 and 5 Hz) and both values plotted on the curve. In this case, as the seizure event involves increased connectivity among channels, the two values exist on the left hand side of the curve. The inverted curve indicates the balance between the number of connections between channels and entropy.

Figure 7A:
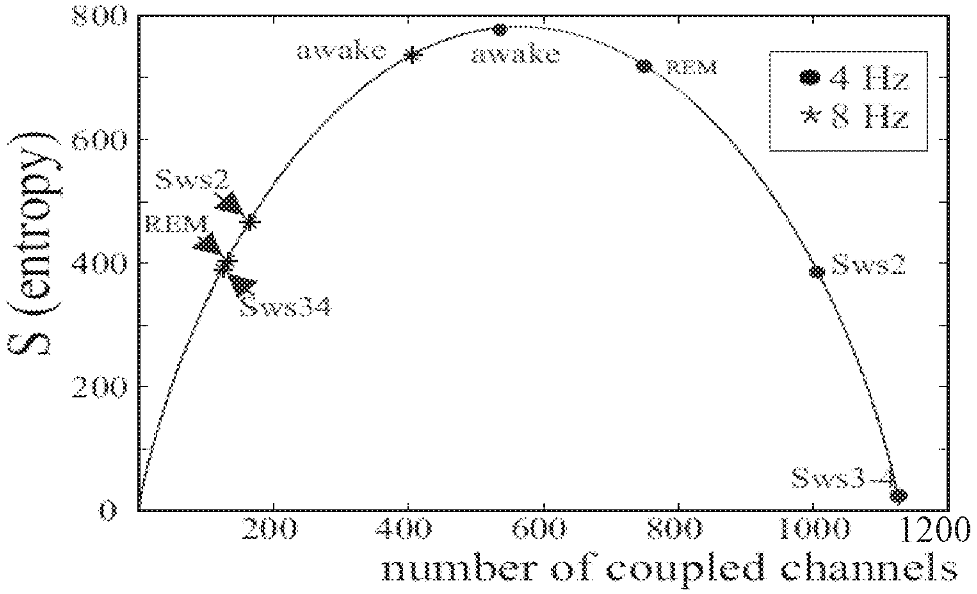
FIGS. 7A and 7B show an example graph for a person without epilepsy.
Figure 7B:
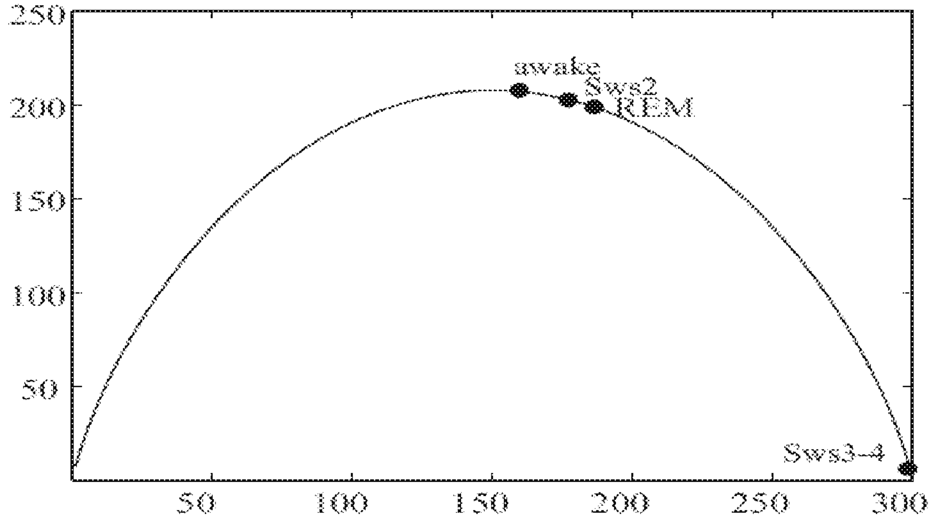

FIGS. 7A and 7B show an example graph for a person without epilepsy. This subject's brain activity was recorded on 2 separate occasions during both awake and sleep states. The recording was analyzed at the 4 Hz (delta range) and 8 Hz (alpha range) frequencies. The awake, eyes open state has the highest entropy (at the top of the curve) in both FIGS. 7A and 7B. In the awake state there will be maximal processing of information by the brain. Stages of sleep [Slow wave sleep (SWS) stages 3-4 being the deepest) show lower entropy on both sides of the curve in FIG. 7A. The unconscious and natural sleep state shows brain activity that does not process external stimuli nor produces any motor activity. Thus less information is in the network and the entropy value will be lower. Some stages of sleep will have lower entropy and have more connected networks (right hand side of the curve), while at other times the sleep stages will have lower entropy values, and have fewer connected networks (left hand side of the curve). The dreaming state known as Rapid Eye Movement (REM) displays close to awake state entropy values. Raw EEG waveforms and frequencies in REM (not shown) will be similar to those in the awake state, but for no motor activity. Thus the entropy value will be close to the awake state.

FIG. 8 shows an example graph showing brain value index on the y-axis and heart rate entropy on the x-axis.

Figure 9:
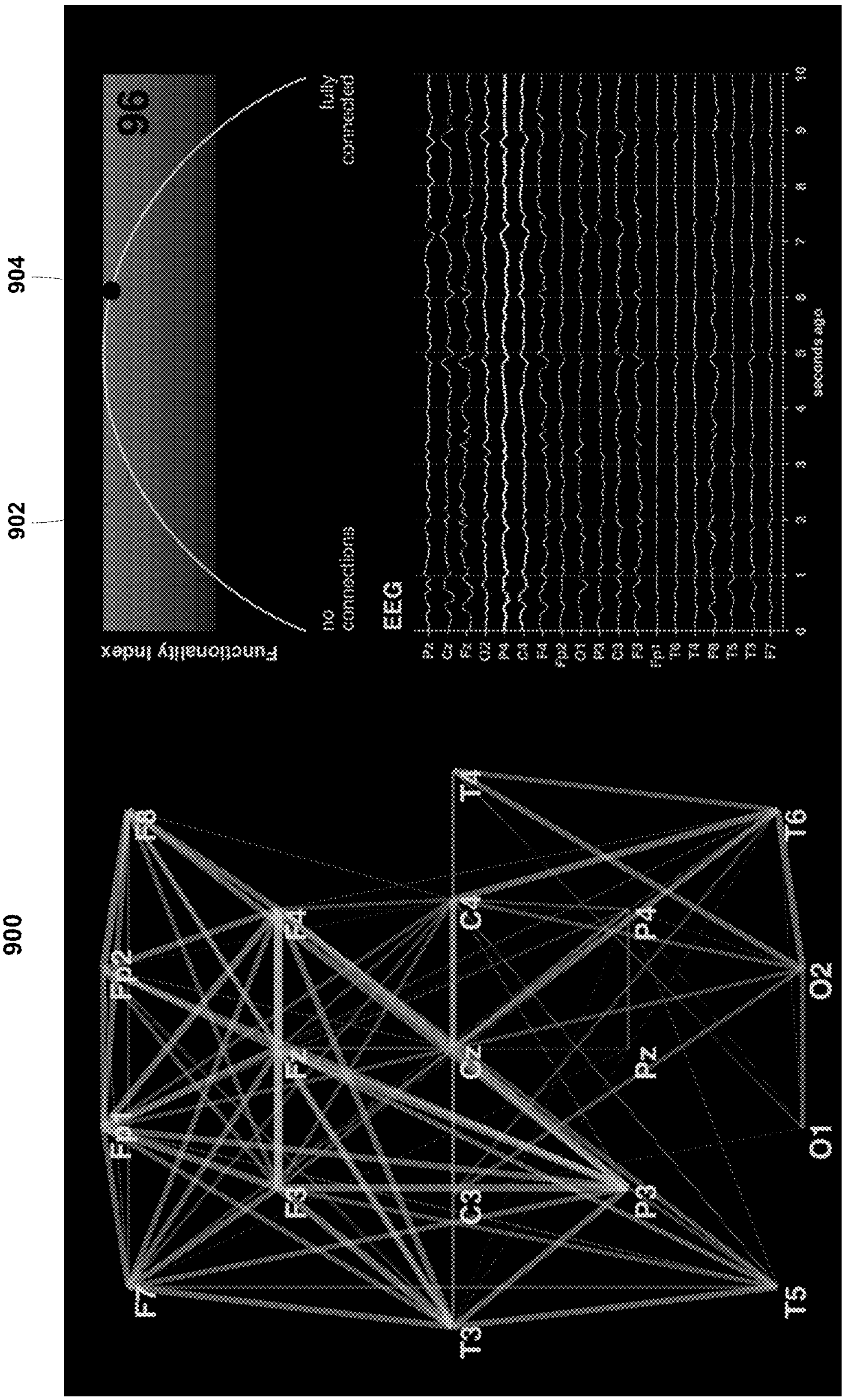
FIG. 9 is an example interface with a visual representation providing a graph for a connectivity map (left), functionality index (right top) or normalized entropy, and raw EEG signals per channel (right bottom) according to some embodiments.

FIG. 9 shows an example interface with a visual representation providing a graph 800 of brain connectivity (left) for different example EEG with 19 channels, a graph 804 with a marker 806 for the real-time brain value index (right top) or normalized entropy, and interface elements 802 for raw EEG signals per channel (right bottom). The interface can also include an indicator value 808 for brain value index. The interface displays relevant electrophysiological signals in real time broken down in panels for one snapshot in time. The left panel shows a graph 800 for the strength of brain connectivity, where stronger connections between channel pairs are represented visually by thicker lines. Transparency is added to increase visibility of partially overlapping EEG channel connections. The right top panel shows a marker 806 the functionality index (or normalized entropy, or BVI) versus the number of active connections and the value 808 of the functionality in the top right corner, displayed as text. The right bottom panel shows streaming from sensors 102 of the raw EEG signals for each channel, over time.

FIG. 9 shows an example interface with a visual representation providing a graph 900 of brain connectivity (left) for different example EEG channels, a graph 902 with a marker 904 for the real-time brain value index (right top) or normalized entropy, and interface elements 908 for raw EEG signals per channel (right bottom). A list of calculated brain value index values 906 is visually represented. In this example R is the brain value index with values between 0 and 1 for each possible channel pairwise. Stronger connections between channel pairs are represented visually by thicker lines. The graph 900 indicates a connectivity matrix with phase locking between channel pairs that have R index greater than 0.45. The lines are shown thicker (weighted via rules) that have higher R. Interface elements 908 show multiple raw EEG signals from different channels. This example includes 8 EEG channels: T3, F7, F8, T4, T5, O1, O2, T6. The brain index value marker 904 ranges between 0 and 100 in this example and indicates the network entropy and how connected the brain is.

Various example interfaces for graphical display will be described. The output from the EEG sensors and processing is displayed graphically for the user and an example with no data is provided in the printscreen image show in FIG. 11A.

The interface is the display seen by the user before recording starts. In panel of the connectivity map 1106 the 8 electrodes are shown as per the device configuration starting with T3 (left anterior temporal electrode) at the top and ending with T6 (right posterior temporal electrode at the bottom). The electrodes are identified by number, as in FIG. 10 and separate the anterior portion of the scalp: T3=0, F7=1, F8=3, T4=3; from the posterior: T5=4, 01=5, 02=6 and T6=7. The numeric output of the Connectivity Map Values will be shown in a column as an integer between 0 and 1 for each electrode or channel pairing, starting with (0,1) and listing all 28 non-repeating channel pairs, ending with (6,7). The waveforms will be seen in a panel as they acquired and correspond with the individual electrodes just described: T3=1, and so on. The window allows for 10 seconds of waveforms and is refreshed every second, for example. The waveforms appear from right to left. The adjacent left panel entitled "Raw EEG Data" will show the voltage in microvolts as an integer value for each of the electrodes. This panel can be hidden in response to a command, for example. Panel 1108 shows the output from the next step after acquisition. Phase synchrony, which quantifies the connectivity between all possible pairs of electrodes (e.g. 0 and 1; 1 and 2, . . . 6 and 7) is an integer value between 0 and 1 in some examples. In addition to a numeric output which can be hidden, connectivity is depicted as solid lines between electrodes that have a phase synchrony index at least >0.45. Further the lines are weighted as shown in the table.

| Connectivity range | Colour and thickness |
|---|---|
| 0.45 to <0.6 | Light grey, 1 point |
| 0.6 to <0.8 | Medium grey, 1.5 point |
| 0.8 to <0.9 | Dark grey, 2 point |
| 0.9 to 1.0 | Black, 3 point |

Server 100 generates a visual element for the connectivity values for display as a connecting line between channel pairs in the connectivity map. Panel includes a curve 1102 that shows output from the step in analytics with the Functionality or Brain Value Index shown as a number between 0 and 100 and a round cursor or BVI marker 1104 that moves to the right or the left side of the curve. Decrease in the Brain Value Index on the right side of the curve is associated with greater connectivity between electrodes, while a decrease in the Brain Value Index down the left side of the curve is associated with less connectivity between electrodes.

At the bottom of the screenshot a portion is shown one of the features of the device whereby the type of recording is identified. If the recording is currently being acquired, the identifier is the date and time of the recording. If previously obtained recordings are being reviewed, they are identified as "Simulation" followed by the date and time of the actual recording. A command feature at the bottom of the panel is the "Start" and "Stop" recording functions.

Figure 11B:
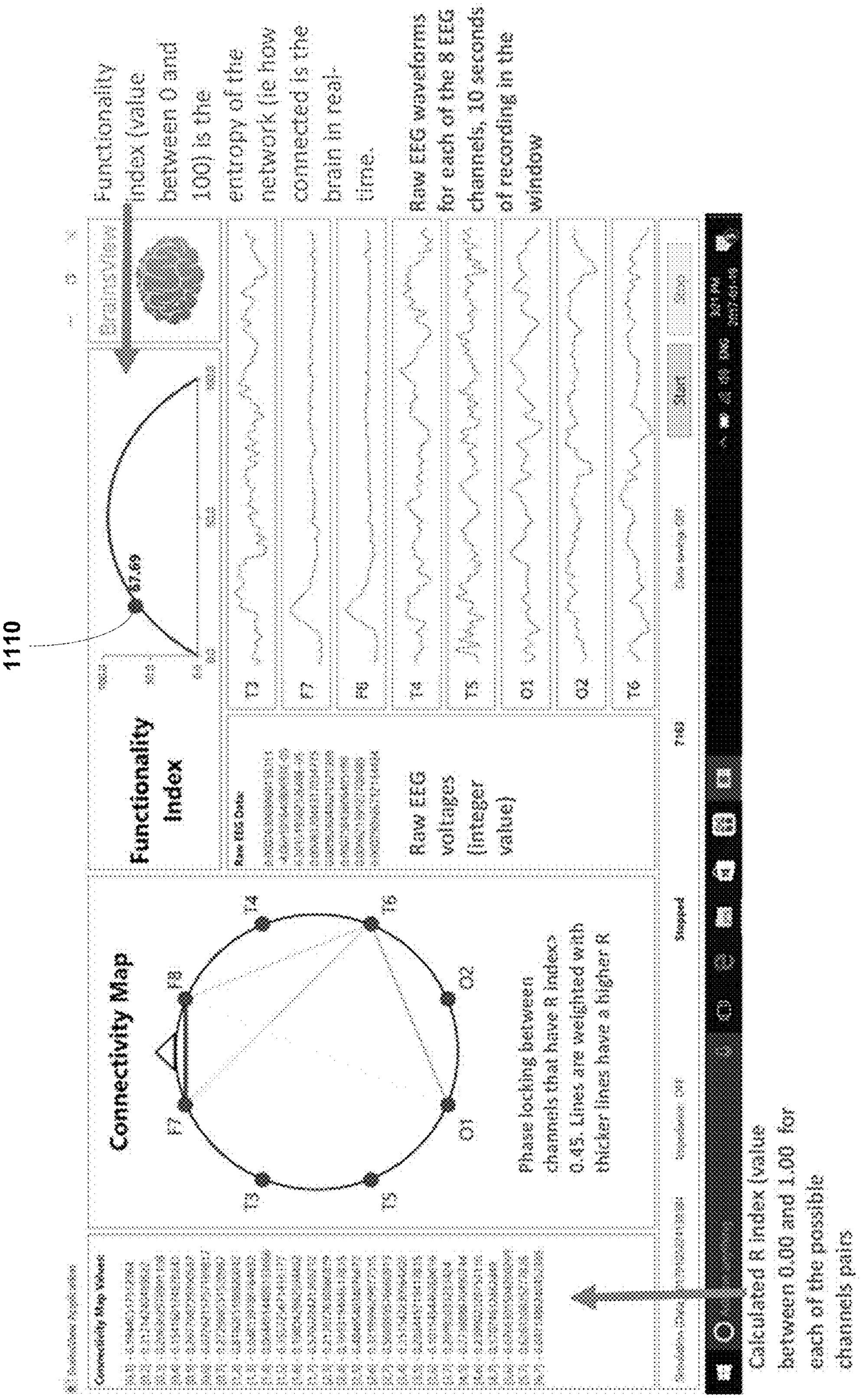
FIG. 11B is an example interface with visual representations as described herein.

Another example interface is shown in FIG. 11B with a BVI marker 1110 with a value of 67.69 showing a change in entropy of a monitored patient. This interface shows a visual elements for connectivity map values, a connectivity map, BVI, and EEG signals. The interface includes a listing of connectivity map values [m, n] with m and n being a channel pair. The EEG signal data for each channel m and n is depicted by visual elements in interface. Server 100 transforms the EEG signal data to generate the connectivity map values. Server 100 processes the connectivity map values to generate the connecting lines for the connectivity map of the interface. The values are filtered using the threshold and ranges to depict different types of connectivity lines. That is, each range of values has a corresponding type of connectivity line to provide a clear visualization of the brain state connectivity. The server 100 can calculate the connectivity using the phase synchrony between EEG data signals for channel pairs. The server 100 computes the BVI marker 1110 using the connectivity map values to provide a clear visualization of the brain state in (near) real-time. The interface provides improved visual elements to facilitate presentation of complex brain signal data.

Figure 12:
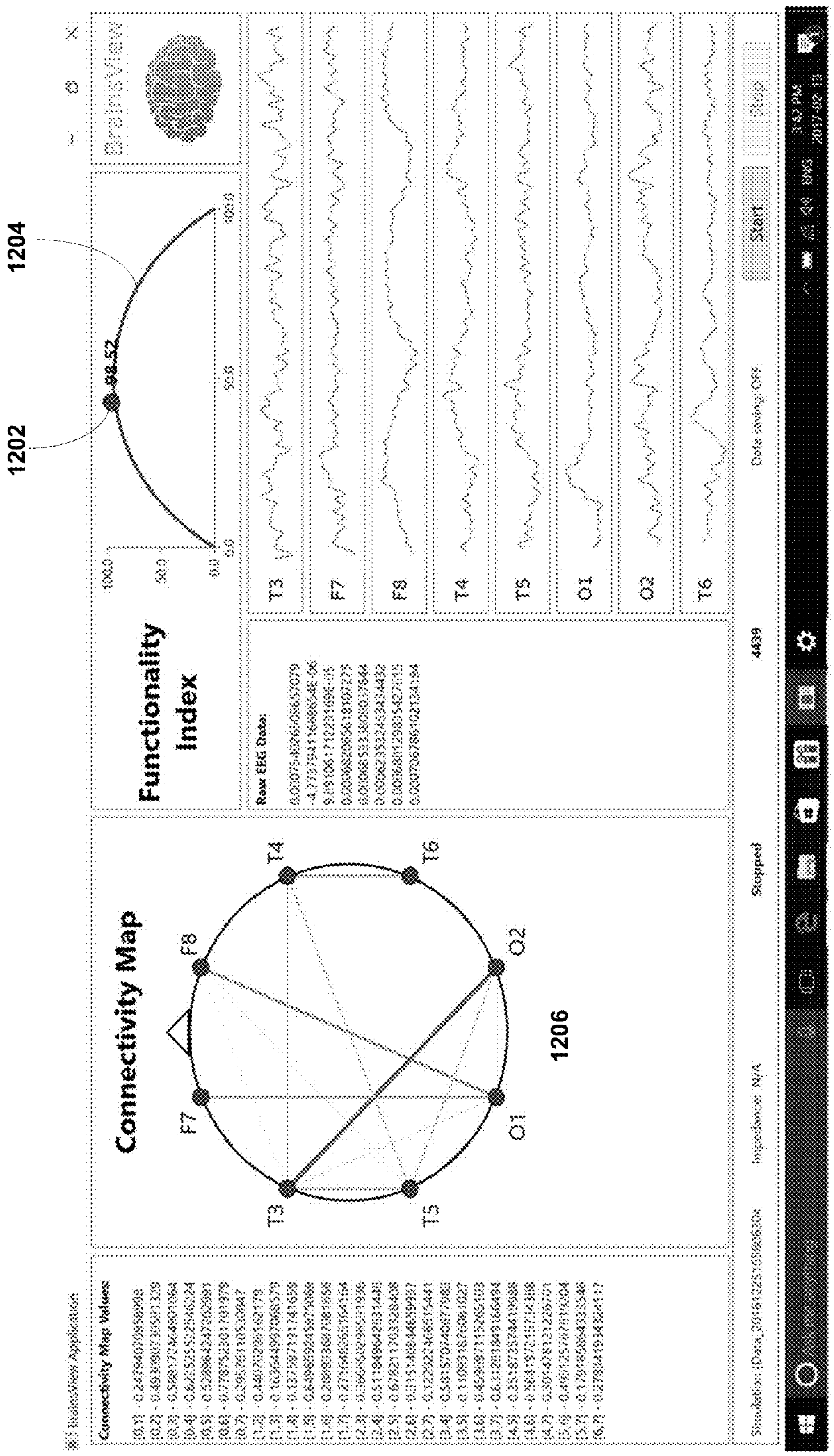
FIG. 12 is an example interface with visual representations as described herein.
Figure 13:
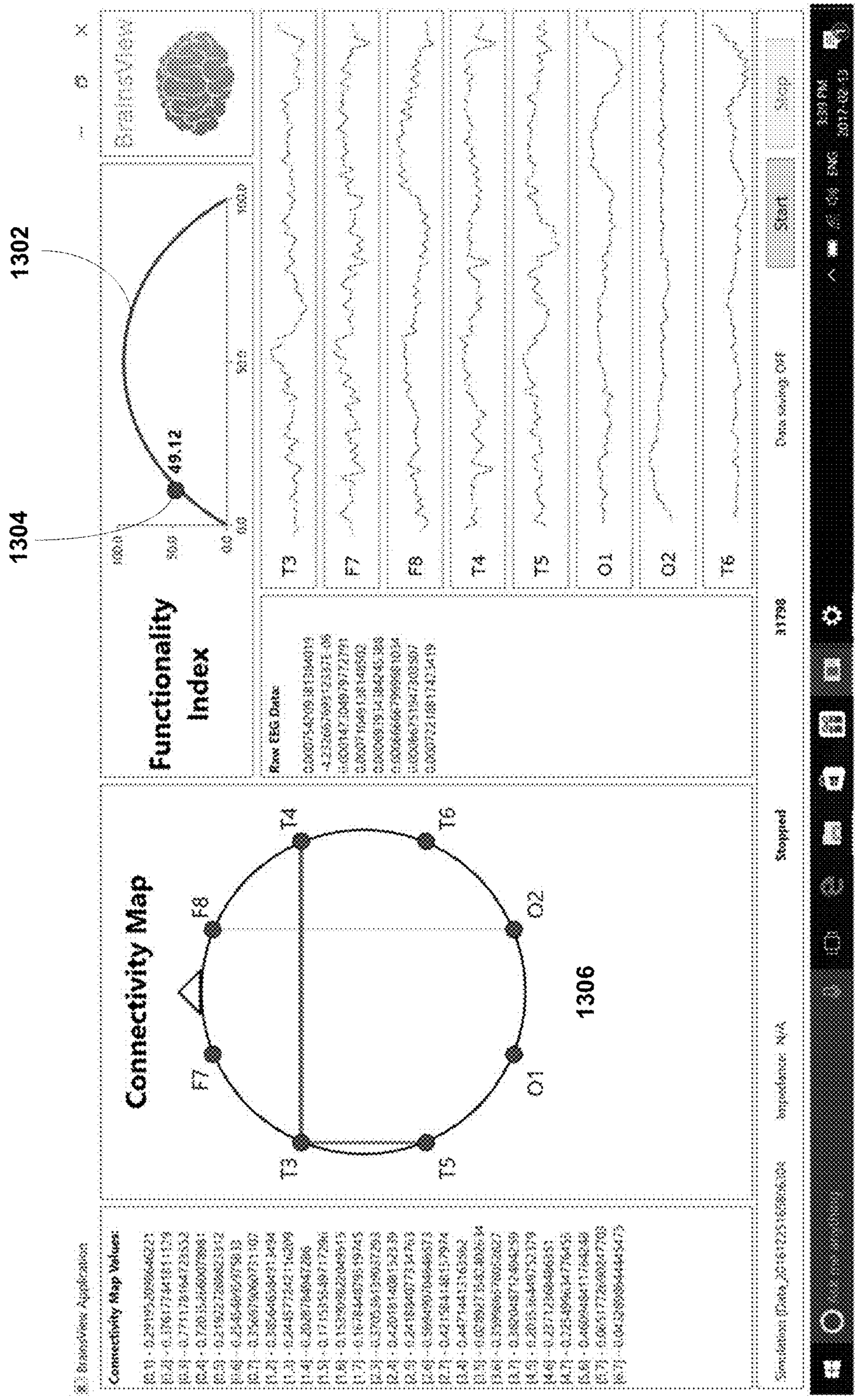
FIG. 13 is an example interface with visual representations as described herein.

FIGS. 12 and 13 show example interfaces for a normal brain function versus concussion. This example compares the brain function of a 54 year old female who had sustained a concussion 3 months prior and that of a gender and age matched control with no history of head injury or neurological impairment.

FIG. 12 shows an interface or screenshot that depicts one time epoch in the 133 seconds of recording of a 54 year old woman, which is representative of her normal brain function. The EEG wave forms (bottom right hand corner) are normal for age. The Functionality Index (depicted by a BVI marker 1202 in top right hand corner) is 98.52 and just left of centre on the curve 1204. The Connectivity Map 1206 shows intrahemispheric (within the hemisphere) and interhemispheric (between the hemispheres) connectivity to different degrees, between pairs of electrodes. For example, T3 and 02, phase synchrony index>0.9; T3 and T4, phase synchrony index 0.47 to 0.6.

In contrast, FIG. 13 shows an interface or screenshot that depicts the functioning of the 54 year old woman who had sustained a concussion 3 months prior. It is representative of the overall 133 seconds of recording. The patient still complained of "fogginess" and difficulty concentrating. She had only just returned to part time work as an administrative assistant. The EEG wave forms are within normal limits for her age, with low amplitude waves in occipital channels. The Functionality Index is 49.12 and depicted by a marker 1302 on the left hand side of the curve, indicating less connectivity. The Connectivity Map 1306 shows only 1 intrahemispheric connection between T3 and T4 (phase synchrony index>0.9) and only 2 intrahemispheric connections between T3 and T5 (phase synchrony index 0.6 to 0.8) and F8 to 02 (phase synchrony index>0.47 to 0.6).

Figure 14:
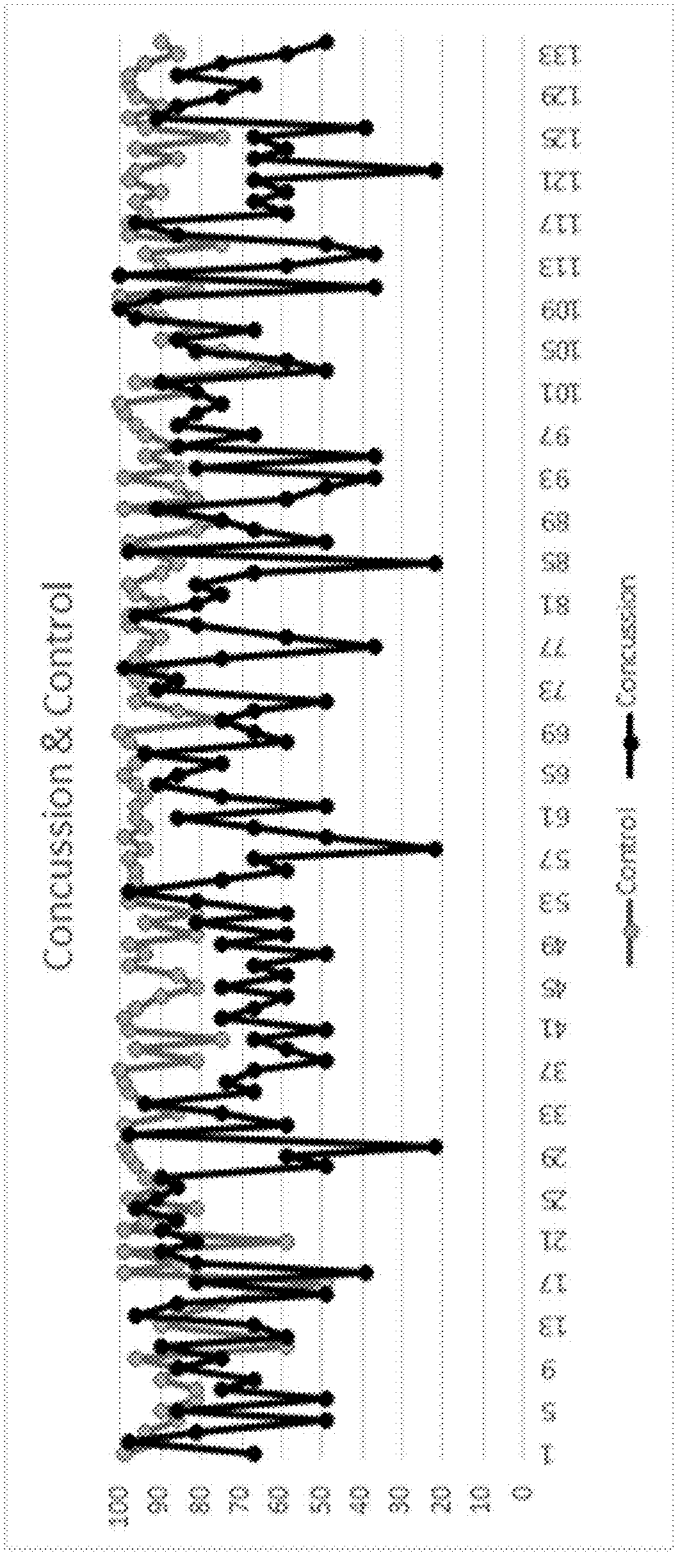
FIG. 14 is an example graph relating to a patient with a concussion as described herein.

Functionality Index time series. FIG. 14 is a graph that depicts the comparison of BVI or Functionality Indices over the time length of each 133 second recording. The patient with concussion has predominantly lower Functionality Index values. The difference in mean Functionality Indices between the control subject (90) and concussion patient (70) is statistically significant with t-test $p<0.001$.

Figure 15:
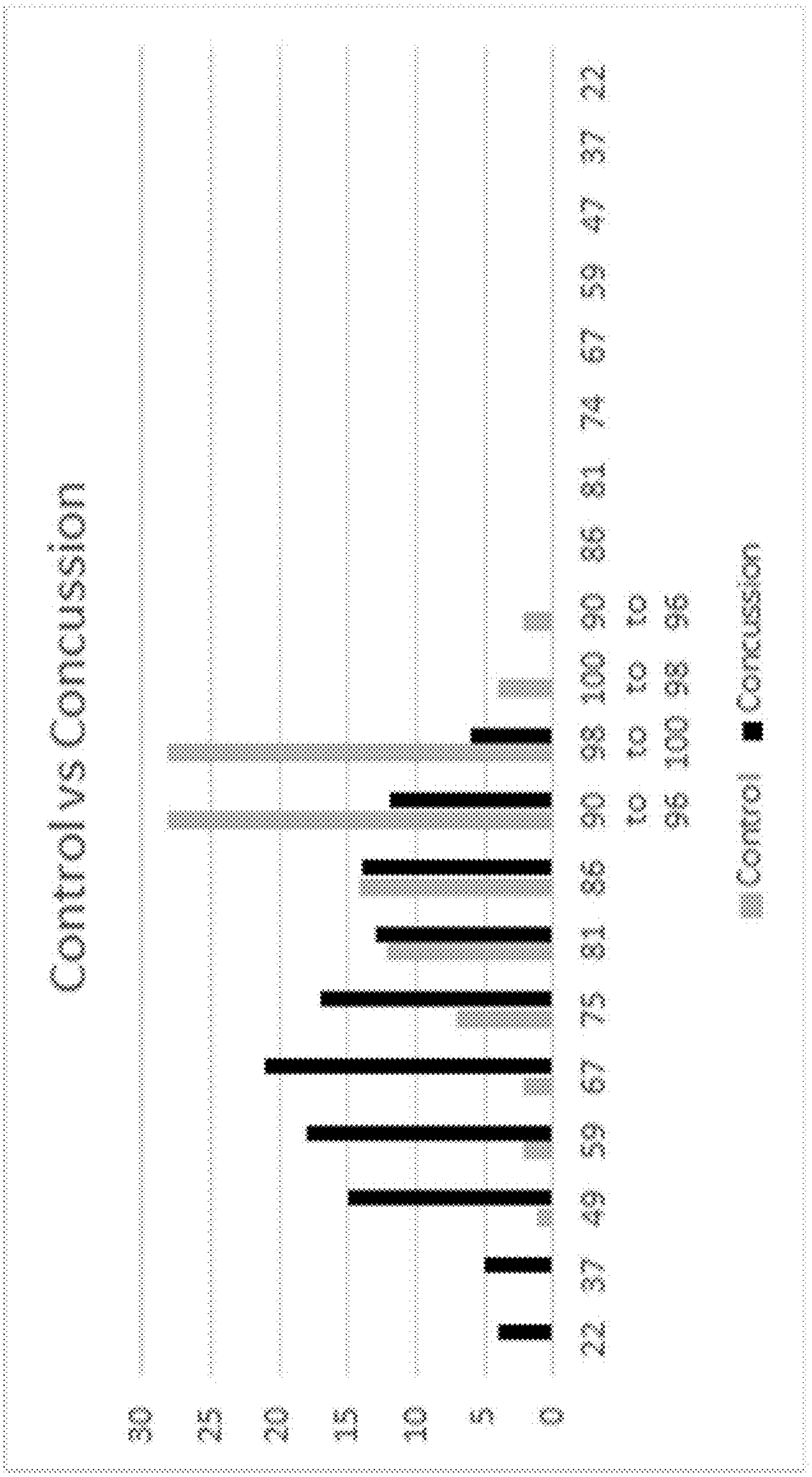
FIG. 15 is an example graph relating to a patient with a concussion as described herein.

Functionality Index frequencies. FIG. 15 is a graph that shows another method of comparison of the patient with concussion and the age and gender matched control with respect to Functionality Index values. The patient with concussion has lower Functionality Index values and they are on the left hand side of the curve which corresponds to a "disconnected" brain.

Figure 16:
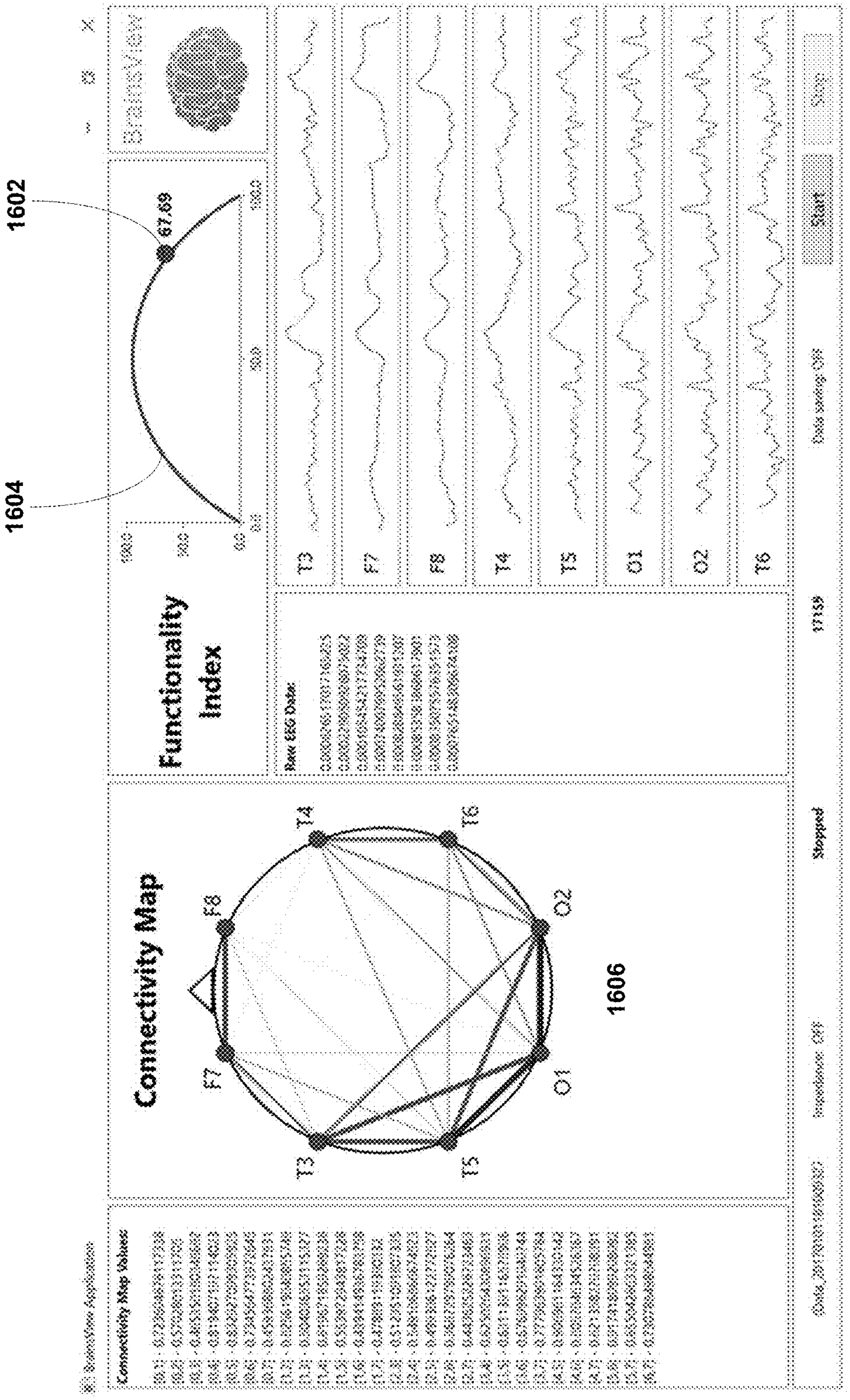
FIG. 16 is an example interface with visual representations as described herein.

FIG. 16 is an example of an interface or graphical display of data relating to a patient with absence epilepsy. This example is that of a 29 year old male with a history of absence epilepsy who is currently not taking his medication. He denies seizures, while independent observers report multiple 1 to 2 second staring events. He consented to monitoring and 94 seconds of EEG and indices were recorded.

The interface of the graphical display shows 1 time point in the patient's recording. Prior to brief, 2 to 3 second events of spike and slow waves consistent with a brain predisposed to epilepsy there is a drop in the Functionality Index (67.69) in the above screenshot. Further, the connectivity map shows thickest lines (R index or connectivity map values 0.8 or 0.9 and greater) across hemispheres between right and left frontal channels (F7 and F8) and right and left occipital channels (O1 and O2) and T5, O1. Maximal connectivity is also seen within the left hemisphere involving the anterior and posterior temporal channels (T3 and T5) and the left occipital channel. This coupled with the decrease in the Functionality index to 67.69 on the right side of the curve (more connected) would alert the clinician that there is a change in brain function. Given the underlying history of absence epilepsy, pharmaceutical treatment with antiseizure medication is warranted.

Figure 17:
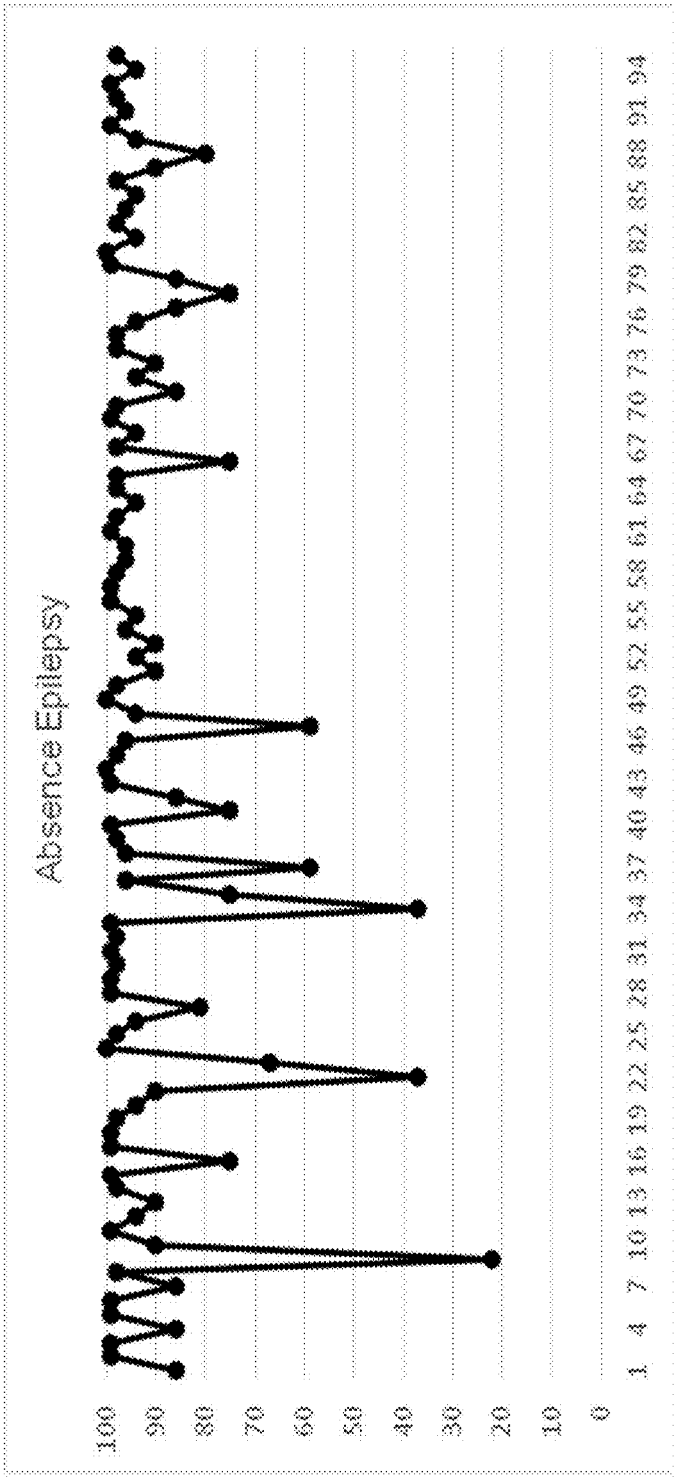
FIG. 17 is an example graph relating to a patient with epilepsy as described herein.

Functionality Index time series. FIG. 17 is a graph showing BVI or functionality index over time. The functionality index changes over the course of the 94 second recording. In the graph below, the x axis represents 94 samples of recording or 94 seconds. The values fluctuate predominantly between 86 and 100 which is expected in the awake, alert state with eyes open. There are decreases in the Functionality Index to 20 and 37 at 9, 22 and 34 seconds. These decreases would again alert the clinician to brain changes and in the case of absence epilepsy the need for treatment with an anticonvulsant medication. This is an example.

Figure 18:
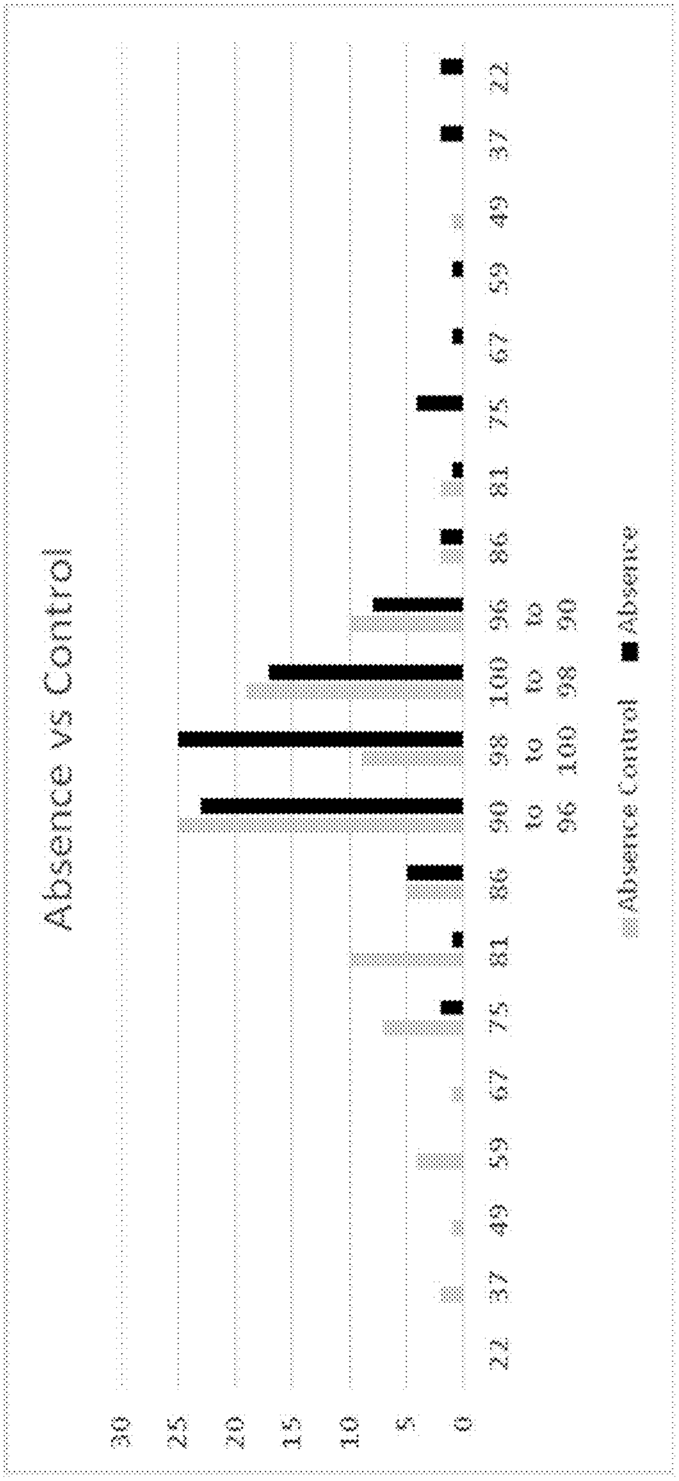
FIG. 18 is an example graph relating to a patient with epilepsy as described herein.

Absence Functionality Index frequencies. FIG. 18 is a graph relating to a patient with epilepsy. The Functionality Index, calculated from the network connectivity of the 8 channels can assume one of 14 possible values on either side of the curve: 22, 37, 49, 59, 67, 75, 81, 86, 90, 94, 96, 98, 99, 100. For the purposes of graphing, values 90 to 96 are grouped together and values 98 to 100 are grouped together.

The graph of FIG. 18 depicts a comparison of the age and gender matched control subject (gray bars) and the patient with absence epilepsy (black bars). The patient with absence shows higher connectivity compared with the control subject as the patient has more indices on the right side of the curve.

Migraine

The next clinical example relates to a 53 year old woman with migraine without aura. She consented to recording during the migraine event characterized as headache with 10/10 pain intensity on the 0 to 10 pain scale, accompanied by fatigue and nausea. The initial recording, 80 seconds in length, was performed 15 minutes post onset of pain. The second recording, 80 seconds in length, was performed 10 minutes after treatment with 1 litre of isotonic fluid. At the time of the second recording, the pain was rated as 4/10 with relief of nausea.

Figure 19:
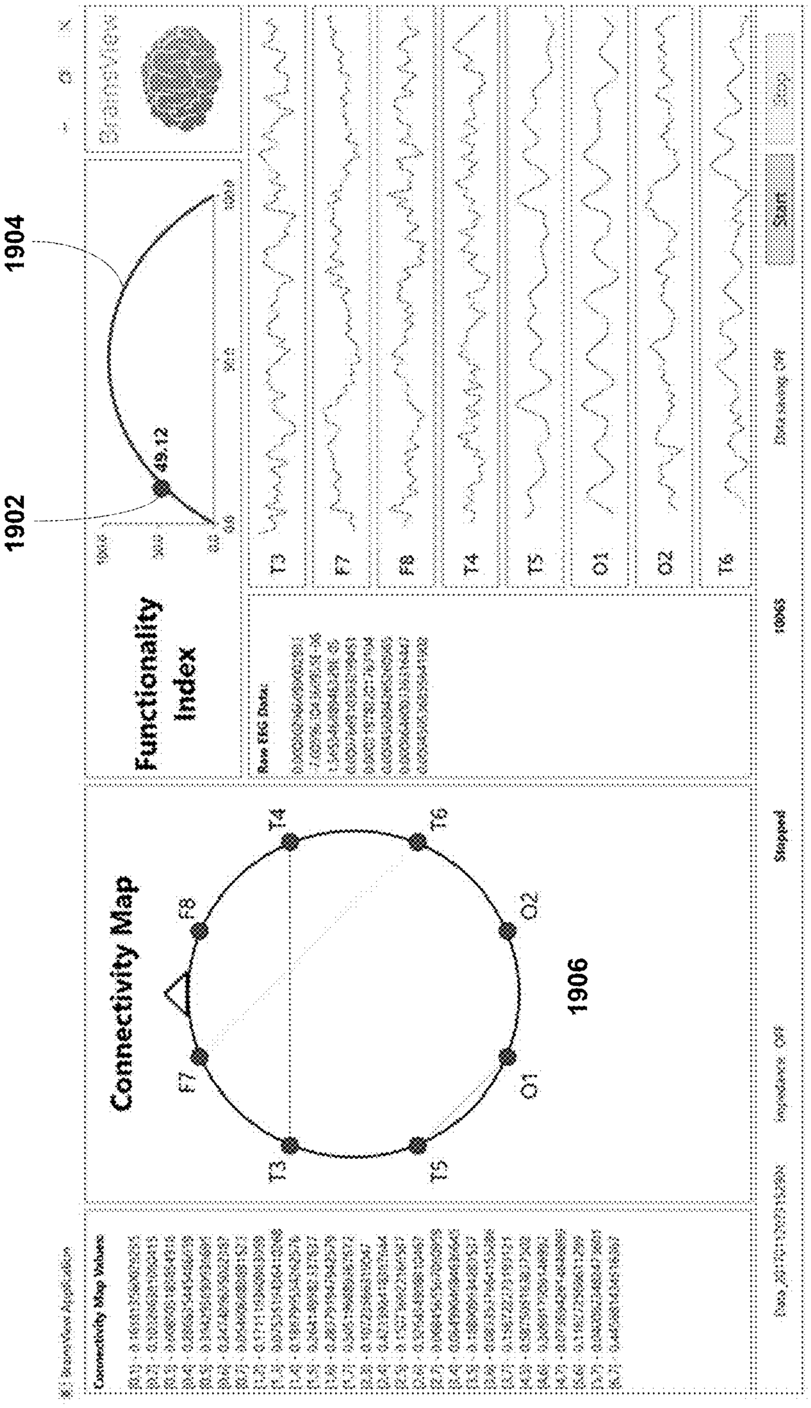
FIG. 19 is an example interface with visual representations as described herein.

FIG. 19 is an example interface with visual representations relating to a patient with a migraine as described herein. The interface or screenshot for migraine monitoring highlights the "disconnection" of the brain during the event. This is seen in the connectivity map where only 2 electrodes show minimal connectivity as depicted by the thin grey line (R Index 0.47 to 0.6) between T3 and T4 and T5 and 01 in the connectivity map 1906. This lack of connectivity is further reflected in the low Functionality Index of 49.12 (BVI marker 1902) on the left side of the curve 1902. This combined with a high pain score would indicate to the clinician the need for migraine treatment and evaluation of the efficacy of the treatment.

Figure 20:
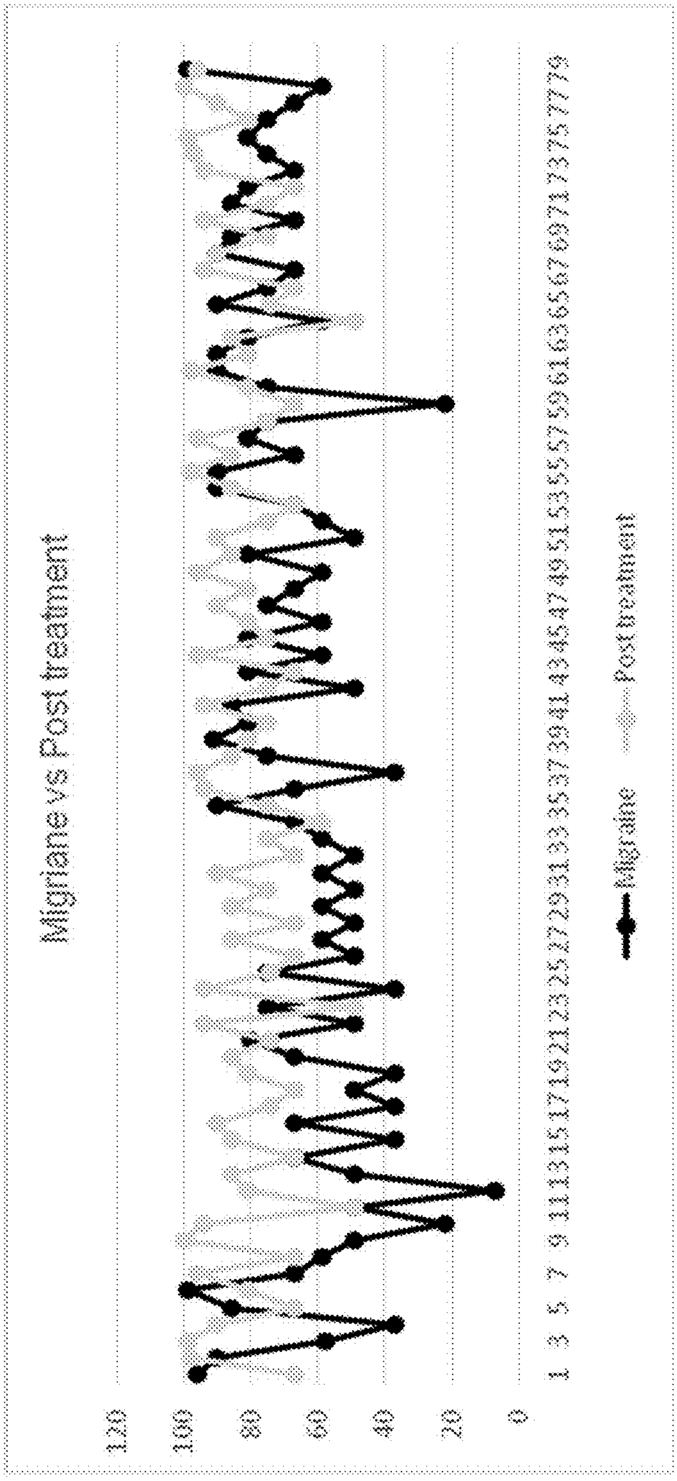
FIG. 20 is an example graph relating to a patient with a migraine as described herein.

Functionality Index time series. FIG. 20 is an example graph relating to a patient with a migraine as described herein. The Functionality Index for each of the recordings is depicted above for the migraine event (black) and migraine post treatment (gray). The difference in means between the migraine event (mean Functionality Index=66) and the post treatment epoch (mean Functionality Index=81) is statistically significant with $p<0.001$.

Figure 21:
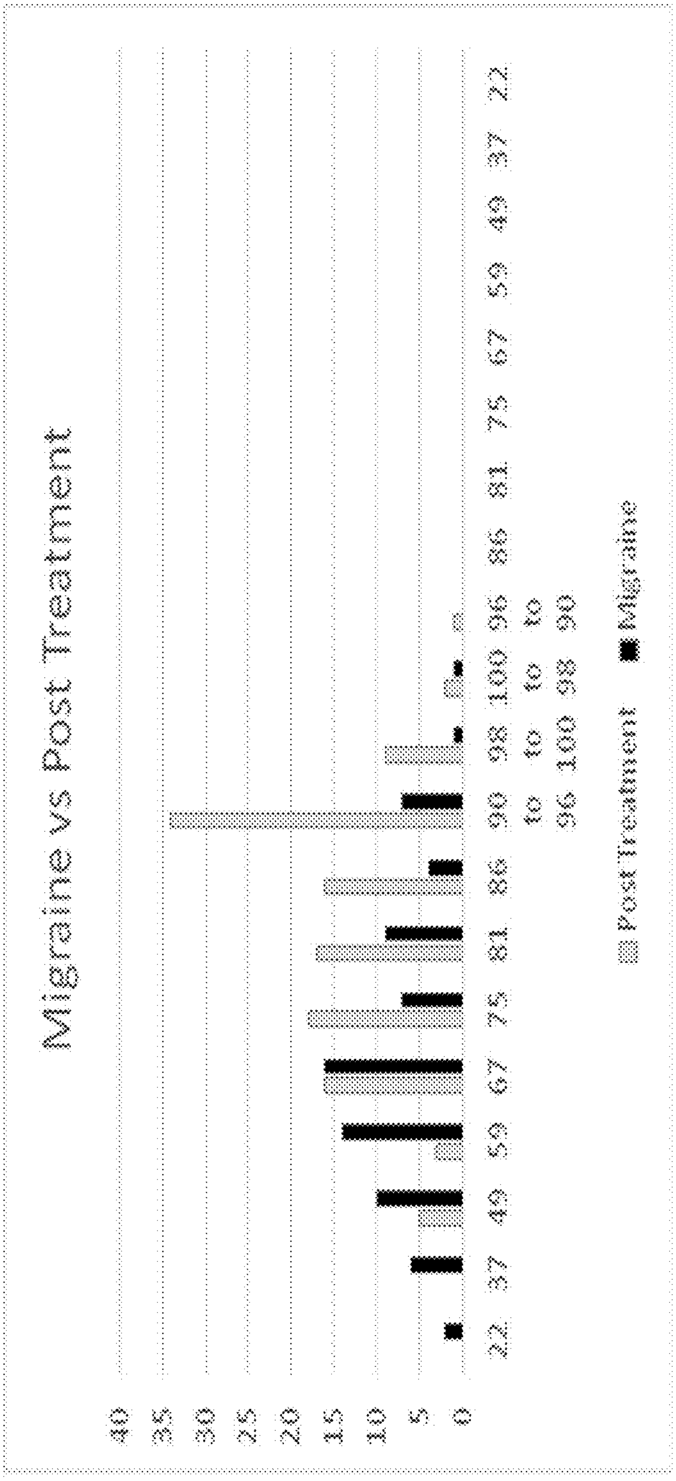
FIG. 21 is an example graph relating to a patient with a migraine as described herein.

Functionality Index frequency bin graph. FIG. 21 is an example graph relating to a patient with a migraine as described herein. The Functionality Index can assume 1 of 14 possible values on either side of the curve, though values 90 to 96 and values 98 to 100 are grouped together. The graph depicts the frequency count (y axis) of the possible values (x axis) for the migraine recording (black bars) and for the post treatment recording (gray bars).

Seizures Due to Recurrent Brain Tumour

A further example relates to a 19 year old, normally developing healthy male with partial complex seizures and was diagnosed with a tumour in his right frontal lobe. Eight months post surgery he developed events that clinically looked like his previous seizures, but EEG performed during a typical event did not show epileptiform activity. The example relates to EEG recordings pre surgery and post surgery to be evaluated using phase synchrony, connectivity map and Functionality Index. Data from the 8 electrodes is extracted. Evaluation of the connectivity maps pre surgery and post surgery reveal similar patterns of connectivity.

Figure 22:
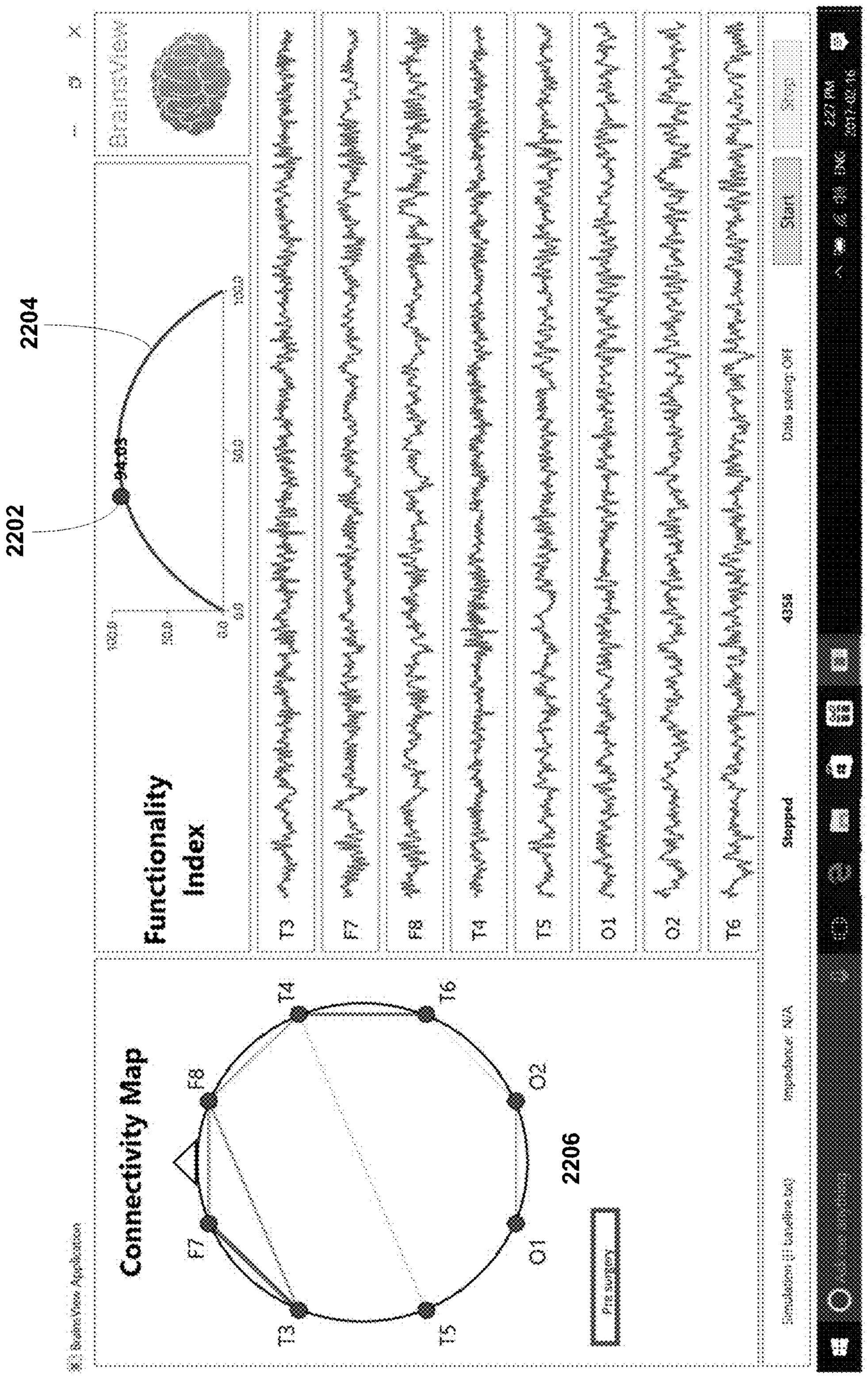
FIG. 22 is an example interface with visual representations as described herein.

Presurgical EEG Evaluation. FIG. 22 is an example interface with visual representations relating to presurgical data as described herein. The interface or screenshot depicts the patient's presurgical raw EEG (bottom right), Functionality Index (BVI marker 2202 on curve 2204) and Connectivity Map 2206. The maximum connectivity (>0.9), based on the thickness of the lines is seen between T3 (left temporal) and F7 (left frontal), T4 (right anterior temporal) and T6 (right posterior temporal) and connectivity of (>0.8 to <0.9) between T3 (left anterior temporal) and F8 (right frontal). There is connectivity between T5 and T4 as well.

Figure 23:
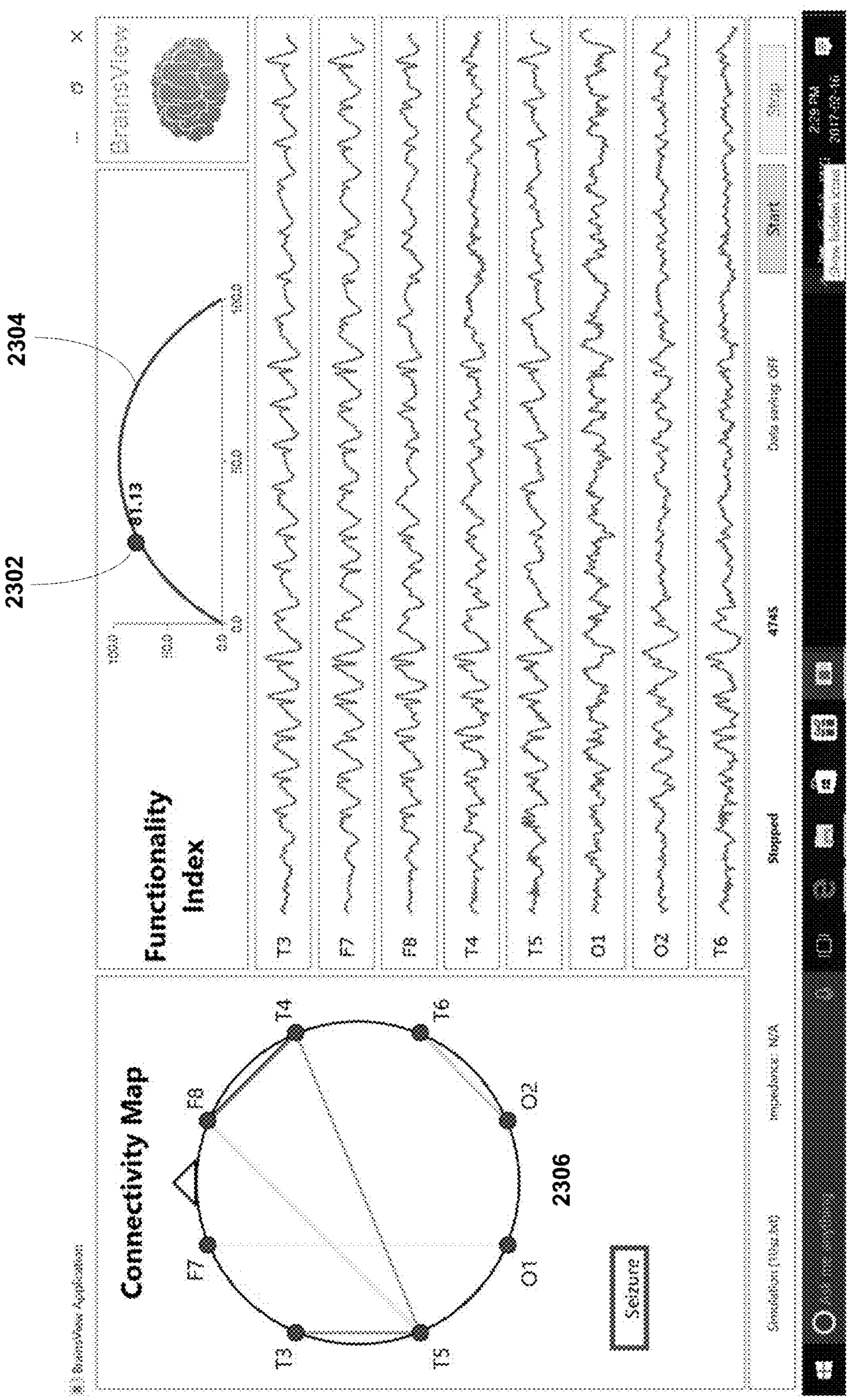
FIG. 23 is an example interface with visual representations as described herein.

Presurgical EEG seizure evaluation. FIG. 23 is an example interface with visual representations relating to presurgical seizure data as described herein. The interface or screenshot shows presurgical seizures with maximum connectivity between F8 (right frontal) and T4 (right anterior temporal). The seizure network includes T5 (left posterior temporal) which is connected to both F8 and T4. T5 and T4 of the connectivity map 2306 are connected at baseline without seizure activity. An MRI revealed a tumour in the right frontal lobe, which was subsequently removed. The patient is conscious during the seizure and aware that he is having the seizure but cannot communicate. His consciousness during the event is reflected in a Functionality Index of 81 (at BVI marker 2402 of curve 2404).

Post Surgical EEG Evaluation

Figure 24:
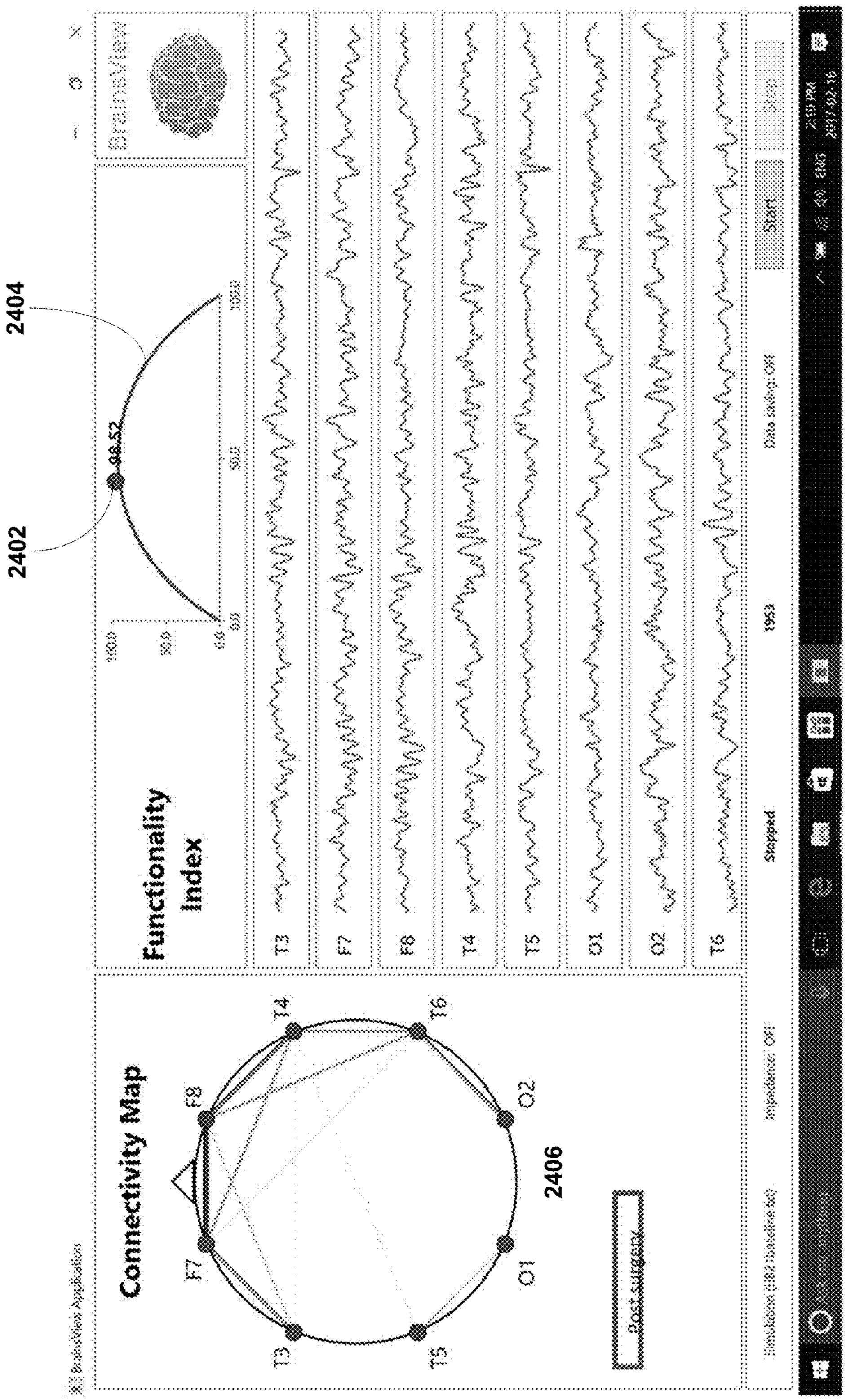
FIG. 24 is an example interface with visual representations as described herein.

FIG. 24 is an example interface with visual representations relating to postsurgical data as described herein. The interface or screenshot depicts the patient's baseline brain function at baseline post surgery. There is no seizure activity during this recording. The baseline network involves left and right frontal channels, left and right temporal and the emergence of the right occipital channel within the network. Subsequent MRI revealed recurrence of the tumour in the surgical site (right frontal lobe). The connectivity map 2404 shows the network connections. The interface shows a Functionality Index of 98 (BVI marker 2402 of curve 2404).

Cardiac arrest and Organ donation. Cardiac arrest has always focused on the changes in heart rhythm. Brain changes occur prior to cardiac arrest. Being able to better monitor cardiac arrest patients who have been resuscitated or those at risk for cardiac death would benefit both the patient and the organ donation programs. Currently the primary pathway by which a patient becomes an organ donor is through brain death. This represents a small percentage of patient deaths. Donation after cardiac death can increase the number of available organs for transplantation.

Patient Data

The following provides examples of patient data that highlight the functionality of the system. A detailed description of the graphical output is first provided. The system includes a graphical display and output from the EEG is displayed graphically for the user and an example interface 1100 with no data is provided in FIG. 11A.

The interface 1100 provides the display seen by the user before recording starts. In panel 1116 8 electrodes are shown as an example device configuration starting with T3 (left anterior temporal electrode) at the top and ending with T6 (right posterior temporal electrode at the bottom. The waveforms will be seen in panel 1 as they acquired. The window allows for 10 seconds of waveforms and is refreshed every second. The waveforms appear from right to left. The adjacent panel 1112 entitled "Raw EEG Data" can show the voltage in microvolts as an integer value for each of the electrodes. This panel 1112 can be hidden in some embodiments. Panel 708 shows the output from the next step after acquisition. Phase synchrony, which quantifies the connectivity between all possible pairs of electrodes (e.g. 0 and 1; 1 and 2, . . . 6 and 7) is an integer value between 0 and 1 in some example embodiments. In addition to a numeric output which can be hidden, connectivity is depicted as solid lines between the 8 electrodes on the head map 706 that have a phase synchrony index at least >0.45 in some embodiments. Further the lines can be weighted as shown in the table below.

| Connectivity range | Colour and thickness |
|---|---|
| 0.45 to <0.6 | Light grey, 1 point |
| 0.6 to <0.8 | Medium grey, 1.5 point |
| 0.8 to <0.9 | Dark grey, 2 point |
| 0.9 to 1.0 | Black, 3 point |

Panel 1114 provides subsequent analytics with the BVI shown as a number between 0 and 100 and a round cursor or indicator 1104 that moves to the right or the left side of the curve 702. Decrease in the BVI on the right side of the curve 1102 is associated with greater connectivity between electrodes, while a decrease in the BVI down the left side of the curve 1102 is associated with less connectivity between electrodes.

At the bottom of the interface 1100, panel 1120 is shown with a feature of the device whereby the type of recording is identified. If the recording is currently being acquired, the identifier is the date and time of the recording. If previously obtained recordings are being reviewed, they are identified as "Simulation" followed by the date and time of the actual recording. The second feature at the bottom of the panel, indicator 1118, is the "Start" and "Stop" recording functions.

Anxiety

An example use case compares a normal brain function to signals captured during a panic attack. This example compares the brain function of a 53 year old female who was experiencing a panic attack with her baseline, non-anxiety recording and that of a gender and age matched control with no history of anxiety disorder. The subject experiencing a self-described panic attack scored 70 on the PROMIS Emotional Distress—Anxiety—Short Form. This corresponds to severe anxiety. The age and gender matched control subject scored 36.3 using the same instrument. This can correspond to none to slight anxiety.

Figure 31:
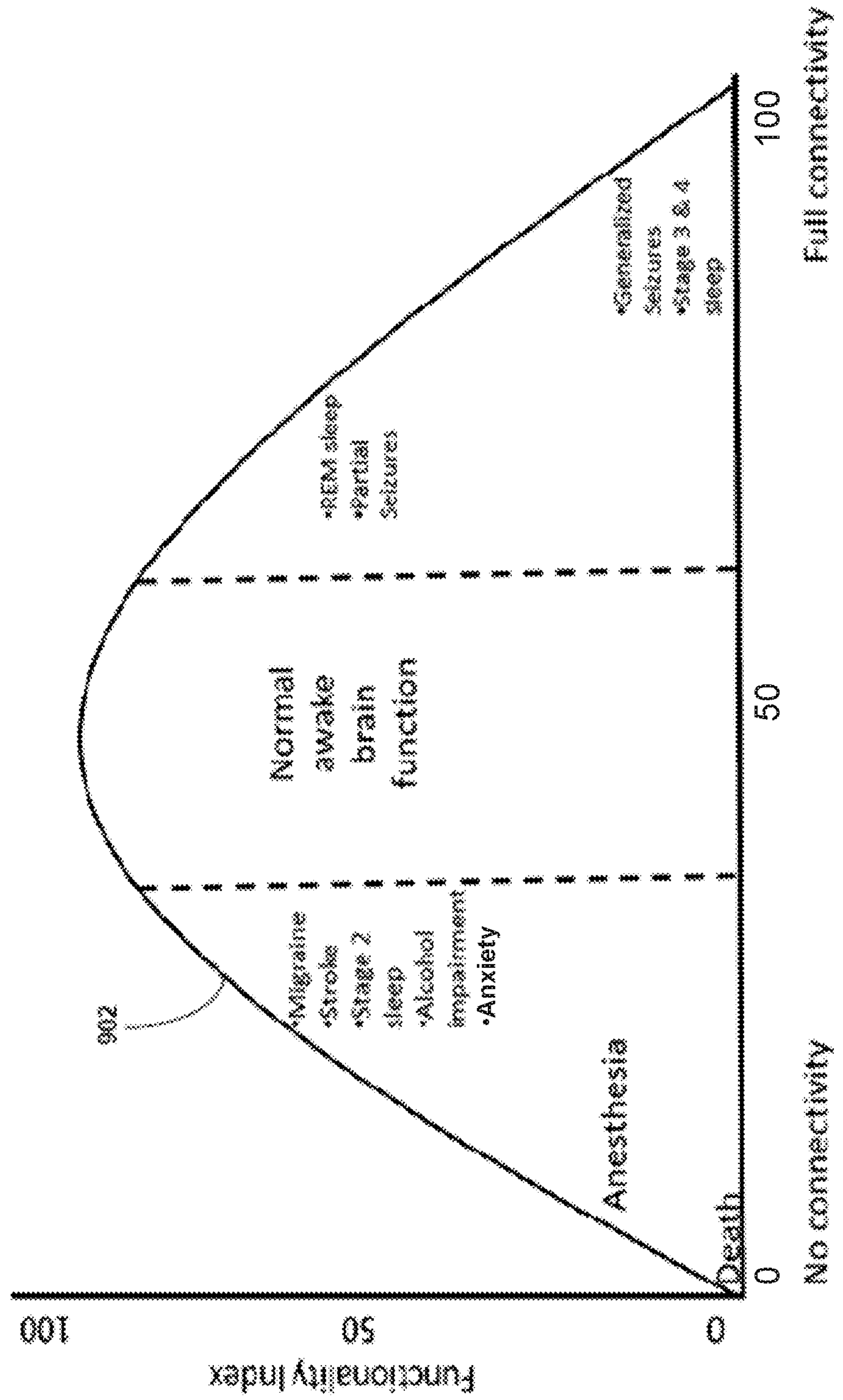
FIG. 31 is an example interface with a visual representation for brain value index values for anxiety as described herein.

FIG. 31 is an example interface with a visual representation for brain value index values for anxiety as described herein. An indicator for the brain value index can move along the curve 902 to different positions depending on the value. Different regions on the curve 902 can represent different brain states or functions, such as a normal awake brain function, migraines, REM sleep, and so on. An anxiety state can be associated with a threshold value or range of values configured for a patient. The values can be determined during a calibration stage, for example. The values can be determined relative to the baseline or "normal" brain state for the patient, as another example. The computed brain value index can be compared with the threshold value or range of values to determine an anxiety state, for example. The threshold value or range of values can be linked to different positions on the curve 902 to indicate the corresponding anxiety state. The indicator can provide a visual representation of the corresponding real-time anxiety state.

Figure 32:
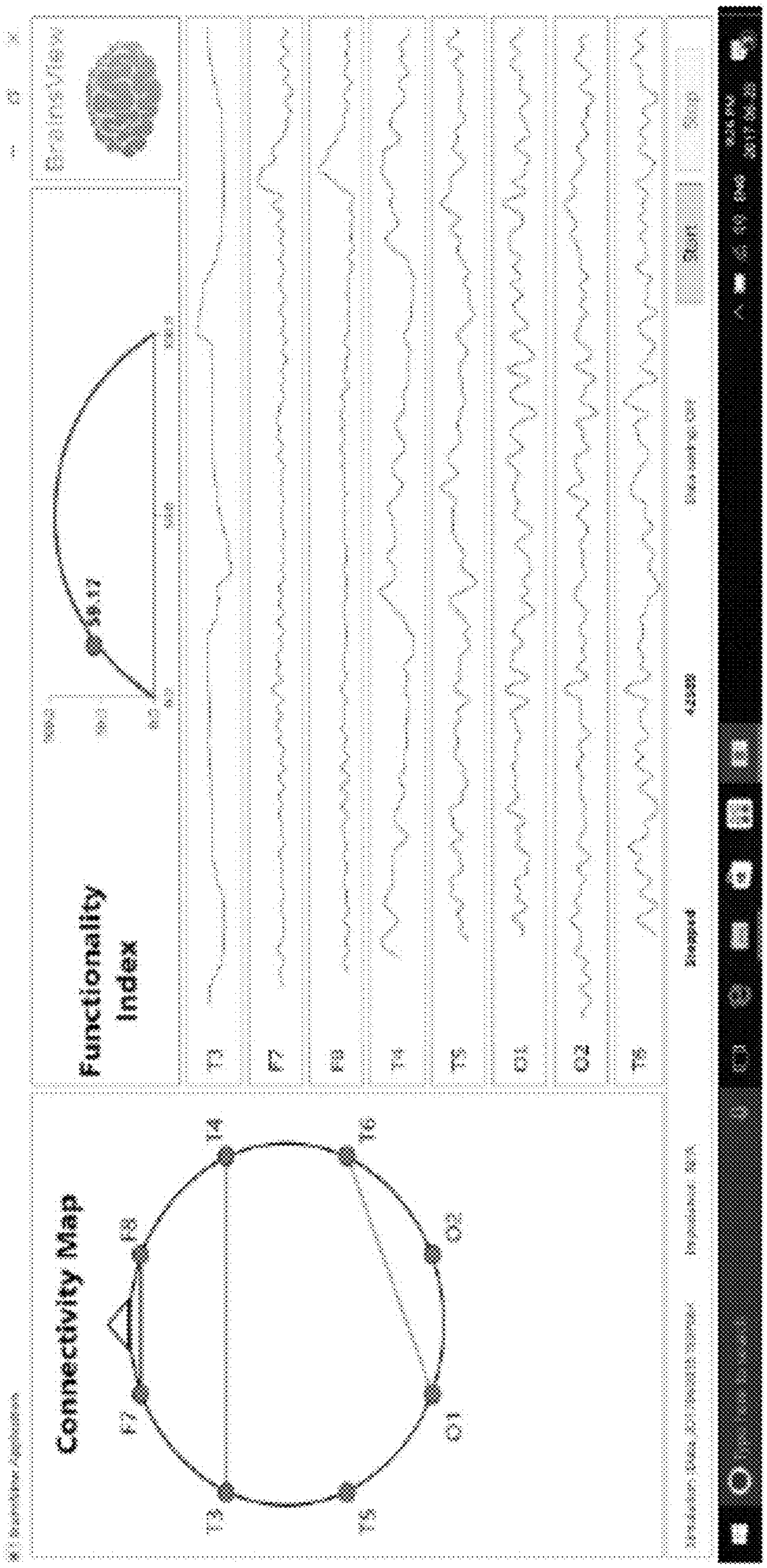
FIG. 32 shows an example interface with a visual representation of a connectivity map, connectivity map values, functionality index, and raw EEG data according to some embodiments.

FIG. 32 shows an interface with a graphical display of normal brain function and anxiety disorder. The interface depicts one time epoch in the 65 seconds of recording of a 53 year old woman, which is representative of her panic attack. The EEG wave forms (bottom right hand corner) are normal for age. The BVI or Functionality Index (top right hand corner) is 59.17 on the left of side of the curve for this example. A Connectivity Map (left hand side panel) shows some interhemispheric (between the hemispheres) connectivity to different degrees, between pairs of electrodes. For example, for F7 and F8, phase synchrony index>0.9; T3 and T4, phase synchrony index 0.47 to 0.6. An anxiety disorder can be associated with a threshold value or range of values configured for a patient. The values can be determined during a calibration stage when the patient is experiencing a panic or anxiety state, for example. The values can be determined relative to the baseline or "normal" (or not anxious) brain state for the patient, as another example. The computed brain value index can be compared with the threshold value or range of values to determine an anxiety disorder, for example.

Figure 33:
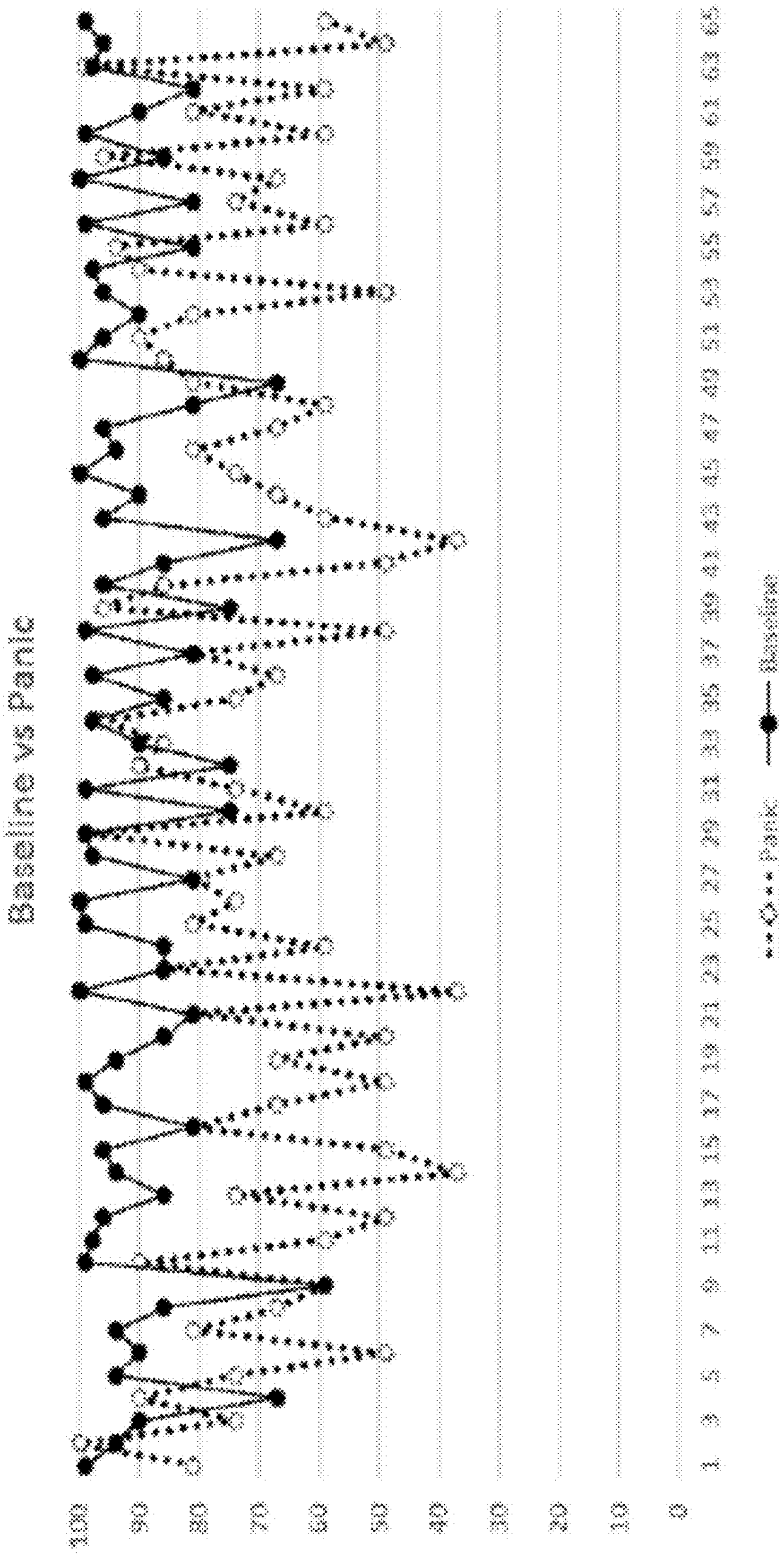
FIGS. 33 to 41 show example graphs for a patient with panic disorder.

FIG. 33 shows an example graph for a patient with panic disorder that can be referred to as a Functionality Index time series. The graph depicts the comparison in Functionality Indices (y axis) over the length of each 65 second recording (x axis). The patient experiencing the panic attack has predominantly lower Functionality Index values during the episode, than when she is not in a state of anxiety. The difference in mean Functionality Indices between the anxiety state (70.3) and baseline (90.0) is statistically significant with t-test $p<0.001$ as an example. These recorded values can be used to determine a threshold value or range of values configured for a patient. The computed brain value index can be compared with the threshold value or range of values to determine an anxiety disorder or anxiety state, for example.

Figure 34:
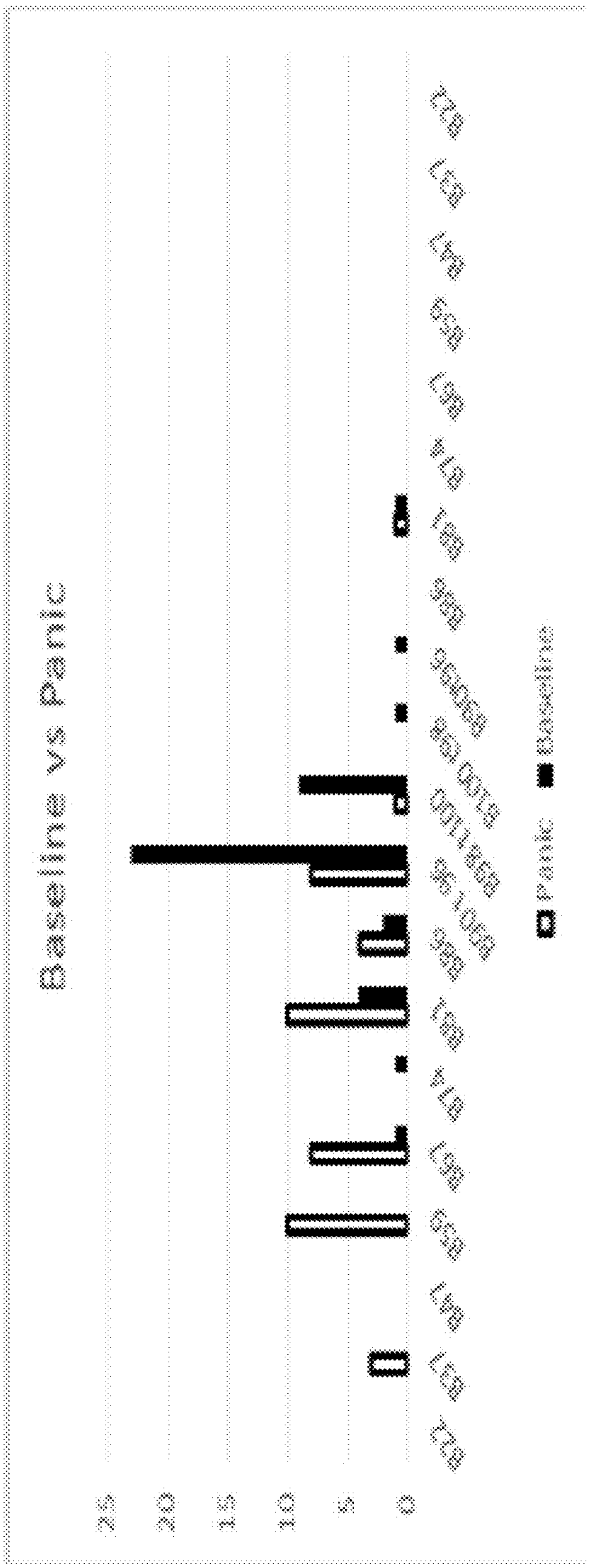

FIG. 34 shows an example graph for a patient with panic disorder that can be referred to as Functionality Index frequencies. The graph shows the frequency with which a value occurs in each of the possible 14 indices on each side of the 100. The Indices corresponding to 90, 94 and 96 are grouped together and those indices corresponding to 98,99, and 100 are grouped together on either side of the curve. In the subject's baseline (not anxious) state, the indices approach a normal distribution with the majority of the indices in the 90 to 96 range, just left of centre. In contrast, the frequency pattern during the panic attack is skewed to the left of the curve with the majority of indices at 59, 67 and 84. A lower brain value index range may indicate an anxiety state than the baseline brain value index range. Historical anxiety data can be used to configure the threshold values or range of values for the anxiety states of the patient.

Another example compares the brain function of the same 53 year old female from the previous example who was experiencing a panic attack with that of a gender and age matched control with no history of anxiety disorder. As in the previous example, the subject experiencing a self-described panic attack scored 70 on the PROMIS Emotional Distress-Anxiety—Short Form. This corresponds to severe anxiety. A threshold value or range of values can indicate this state of severe anxiety. The age and gender matched control subject scored 36.3 using the same instrument. This corresponds to none to slight anxiety.

Figure 35:
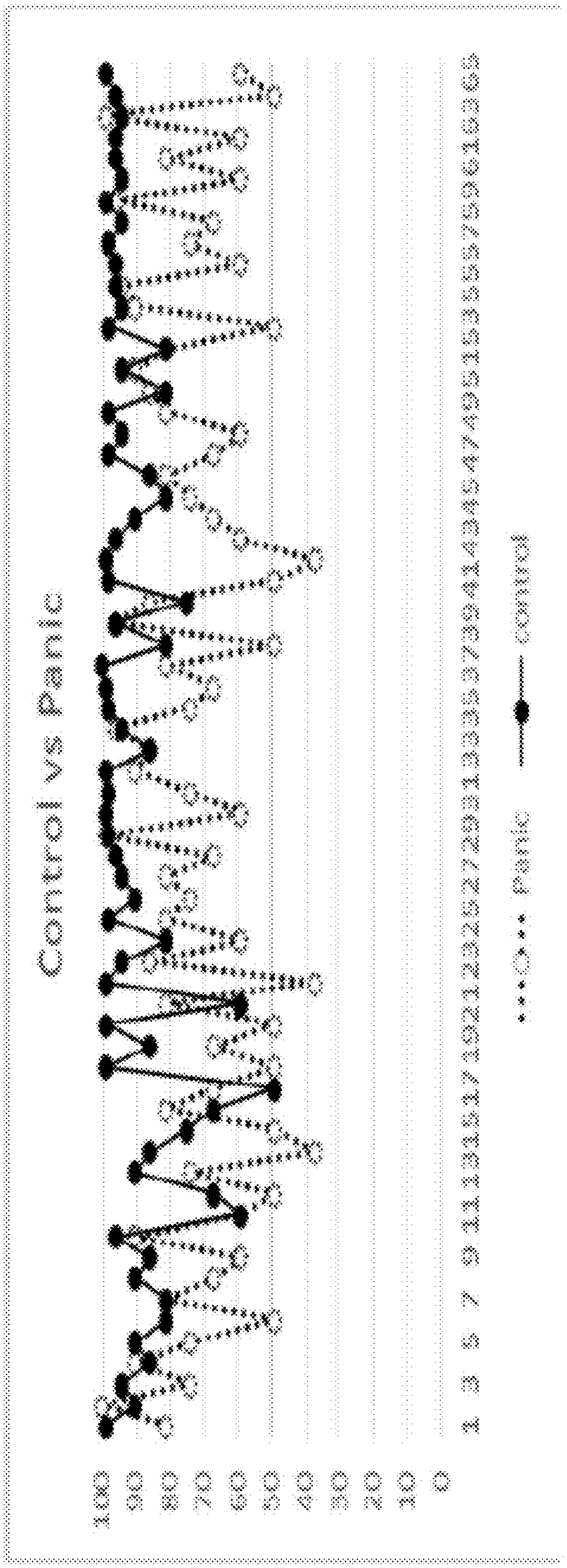

FIG. 35 shows an example graph for a patient with panic disorder that can be referred to as Functionality time series. The graph compares the Functionality Indices over 65 seconds (x axis) for an age and gender matched control subject (solid black line and marker) with that of the patient in example 1 during her panic attack (unfilled marker and dotted black line). The difference in mean Functionality Indices between the anxiety subject (70.3) and control subject (91.2) is statistically significant with t-test $p<0.001$.

Figure 36:
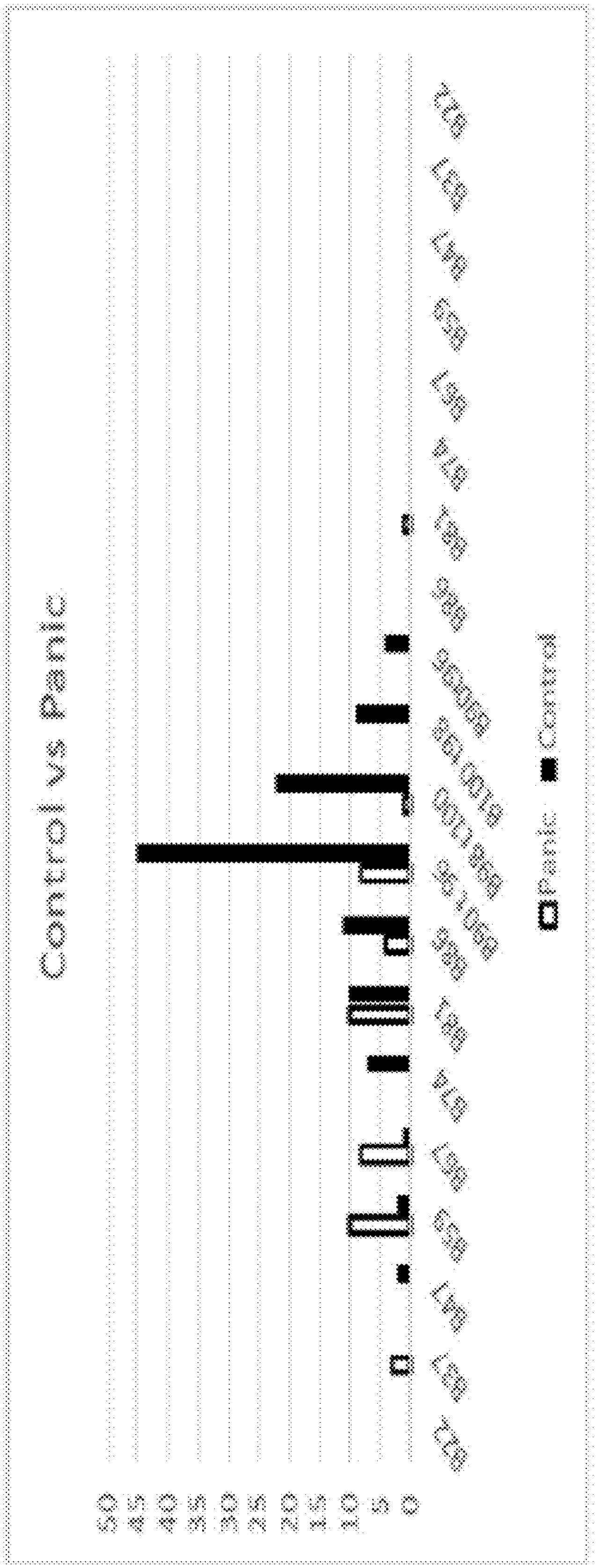

FIG. 36 shows an example graph for a patient with panic disorder that can be referred to as Functionality Index frequency. The graph shows another method of comparison of the patient with anxiety and the age and gender matched control with respect to Functionality Index value frequencies. The patient with anxiety has lower Functionality Index values and they are on the left hand side of the curve which corresponds to a "disconnected" brain. The lower Functionality Index values can correspond to the threshold values or range of values for the anxiety state of the patient.

Figure 37:
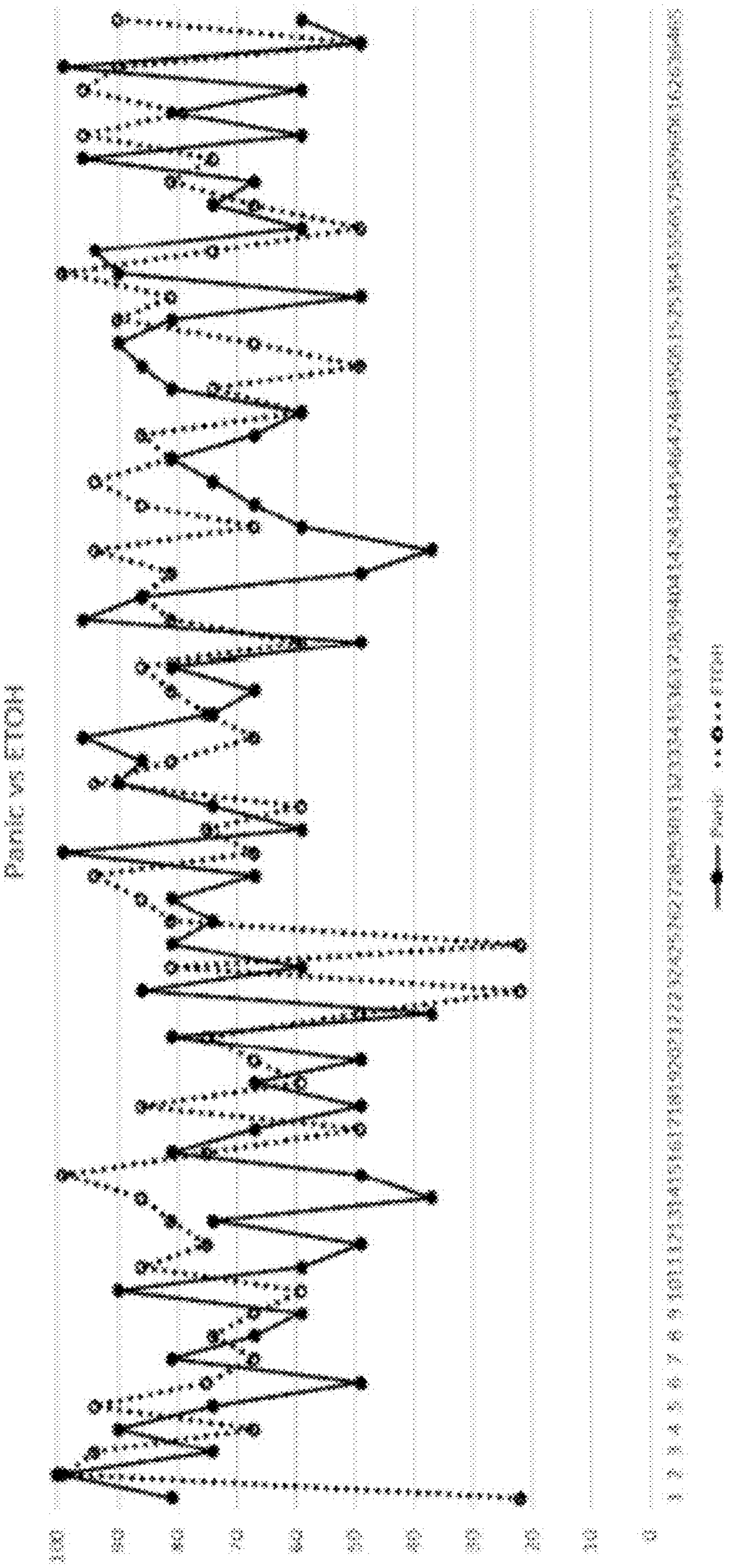

FIG. 37 shows an example graph for a patient with panic disorder that can be referred to as self-medication time series. The graph shows the difference in Functionality indices in the same subject during her panic attack (solid black marker and solid black line) and during self-medication with alcohol (ETOH-open marker with dotted black line). Blood alcohol level at the time of the recording, when the subject declared that the panic symptoms had resolved was estimated at 0.03, based on a weight of 116 lbs and 30 minutes following the equivalent of 1 drink. Functionality indices are both lower than baseline (no anxiety, no alcohol) at 70.3 for the panic and 74.2 for the ETOH). The captured anxiety data can be used to configure the threshold values or range of values for the anxiety states of the patient.

Figure 38:
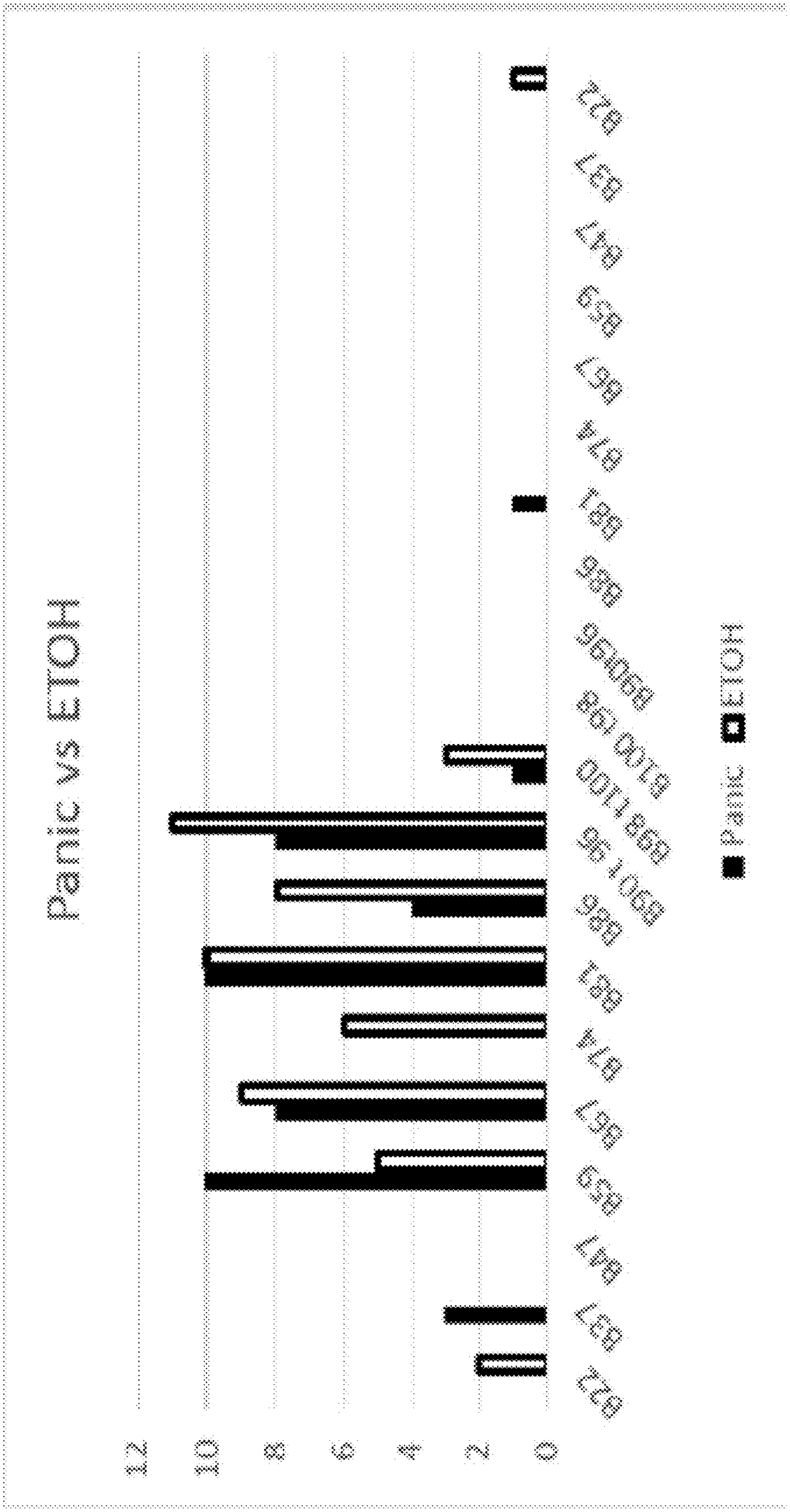

FIG. 38 shows an example graph for a patient with panic disorder that can be referred to as frequency comparison. The graph shows the frequency distribution of functionality indices for the panic state (solid black marker) and the ETOH treatment state (white filled marker). While similar in distribution, the majority of Functionality Indices are in the 67 to 96 range for the ETOH state, while those of the panic state are clustered in the 59 to 81 range. These patterns can be input for machine learning to differentiate panic from intoxication. The machine learning output can be used to configure the threshold values for the anxiety state.

The same subject had a second panic attack within 7 days of the first. It was described similarly with feelings of fear, gastrointestinal upset and muscle tension. The subject experiencing a self-described panic attack scored 67.7 on the PROMIS Emotional Distress—Anxiety—Short Form. This corresponds to moderate anxiety. The average Functionality Index was 74.3, which was not statistically significantly different from the first panic attack, but statistically significantly different ($P<0.01$) from the baseline.

Figure 39:
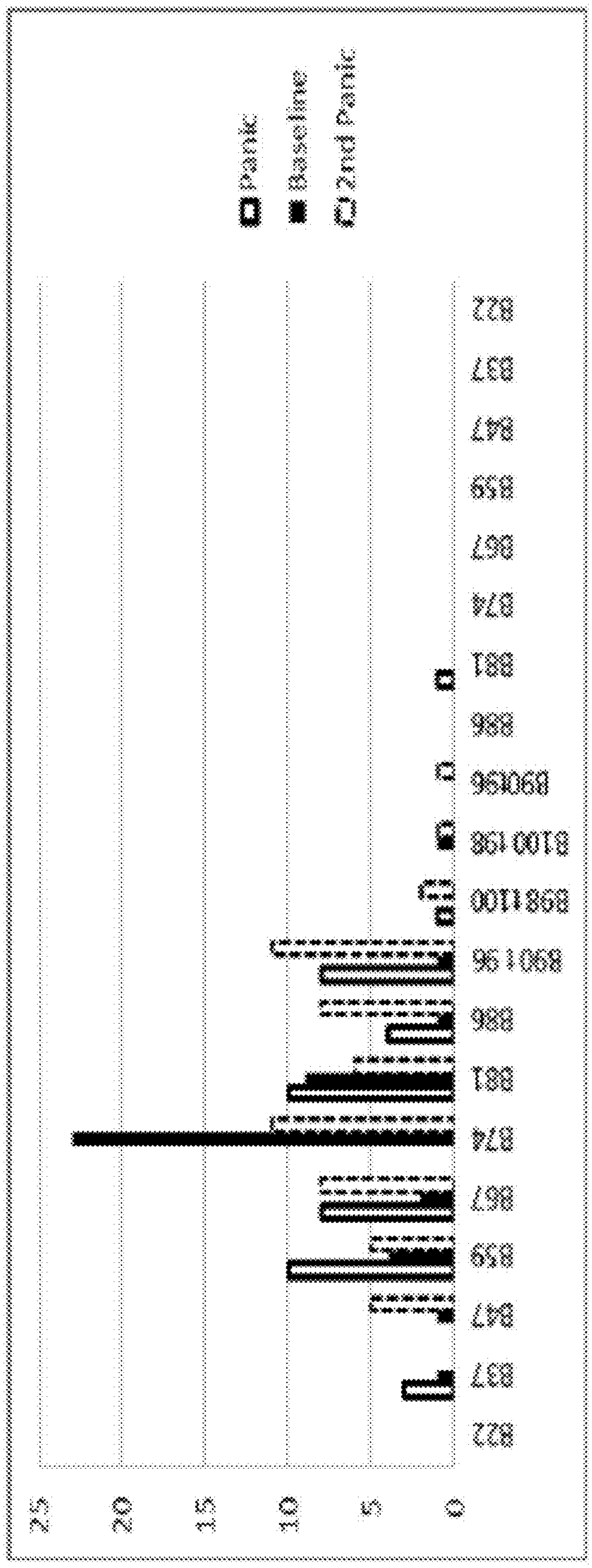

FIG. 39 shows an example graph for a patient with panic disorder. The graph compares the frequency of the Functionality Indices in the same subject during the initial panic attack, during baseline and the second panic event.

Figure 40:
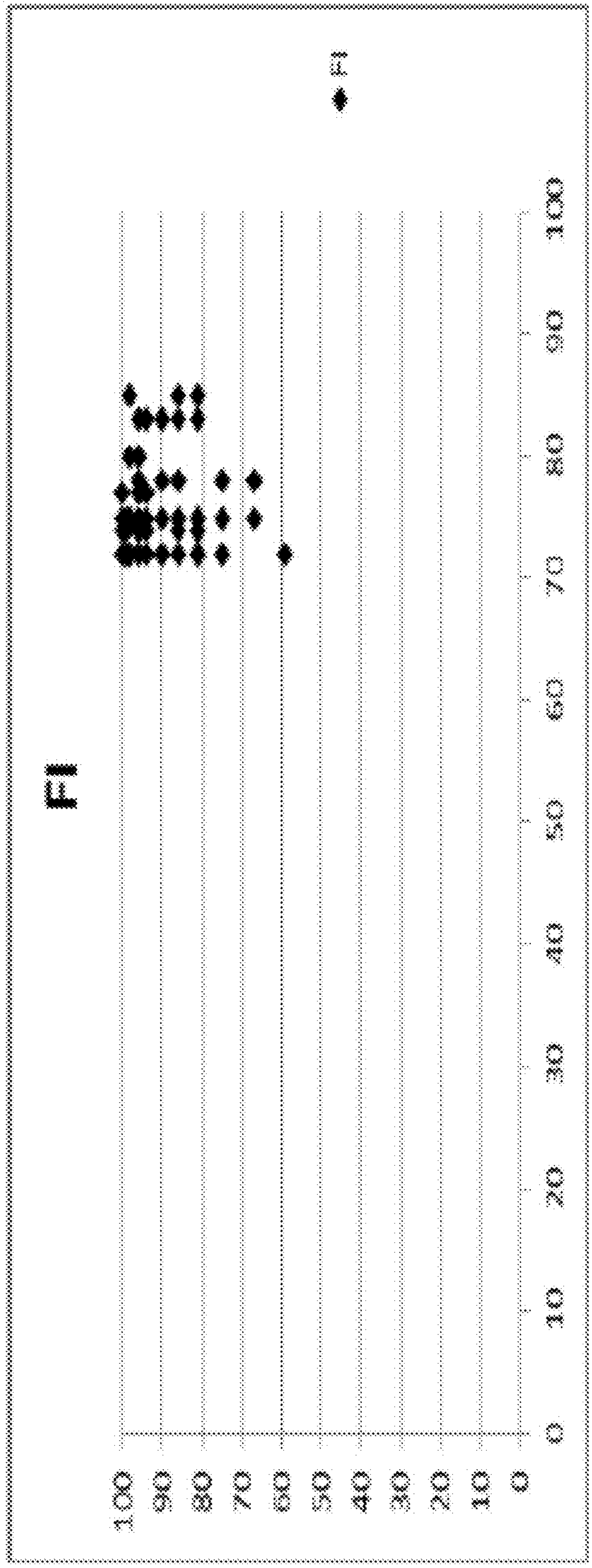

FIG. 40 shows an example graph for a patient with panic disorder. The captured anxiety data can be used to configure the threshold values or range of values for the anxiety states of the patient.

Figure 41:
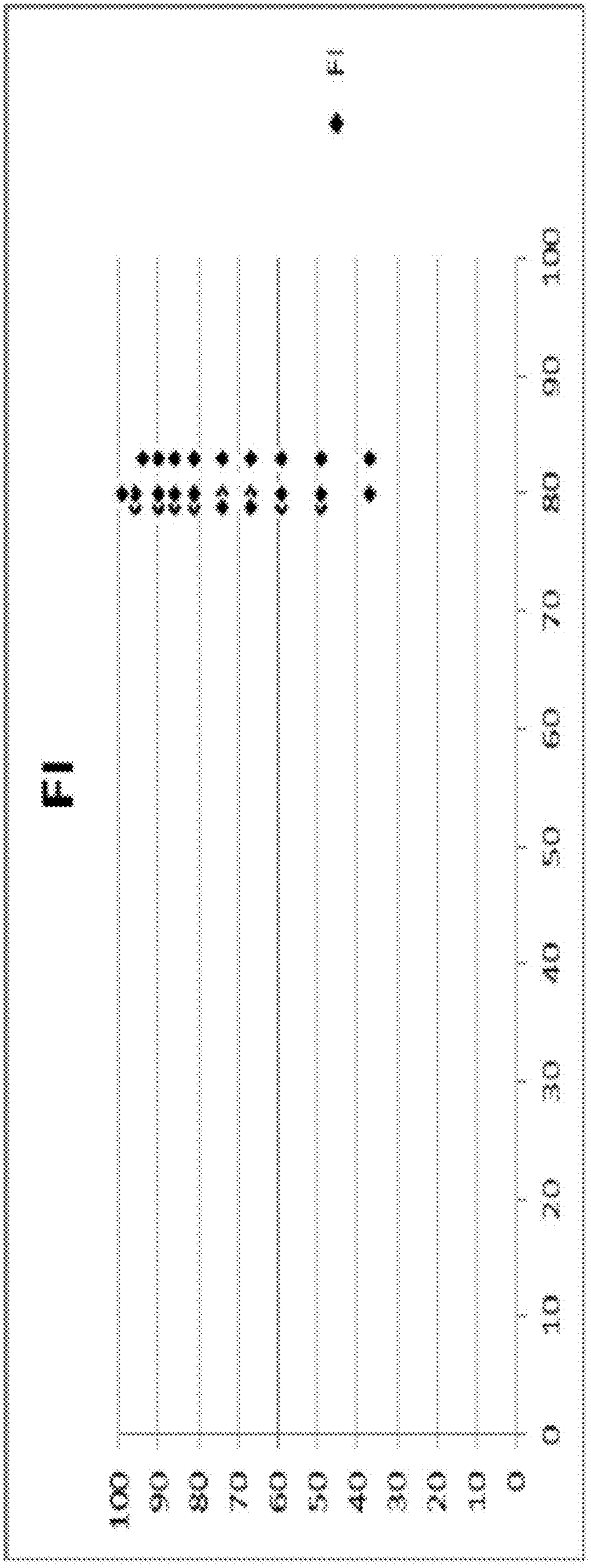

FIG. 41 shows an example graph for a patient with panic disorder. The captured anxiety data can be used to configure the threshold values or range of values for the anxiety states of the patient.

Epileptic Spasms

An example use case compares a normal brain function in an age and gender matched control to signals captured during an epileptic spasms and hypsarrhythmia. This example compares the brain function of a 6 month old female who was experiencing epileptic spasms and hypsarrhythmia with her baseline, non-epileptic spasms and hypsarrhythmia recording and that of a gender and age matched control with no history of epileptic spasms and hypsarrhythmia disorder.

Figure 42:
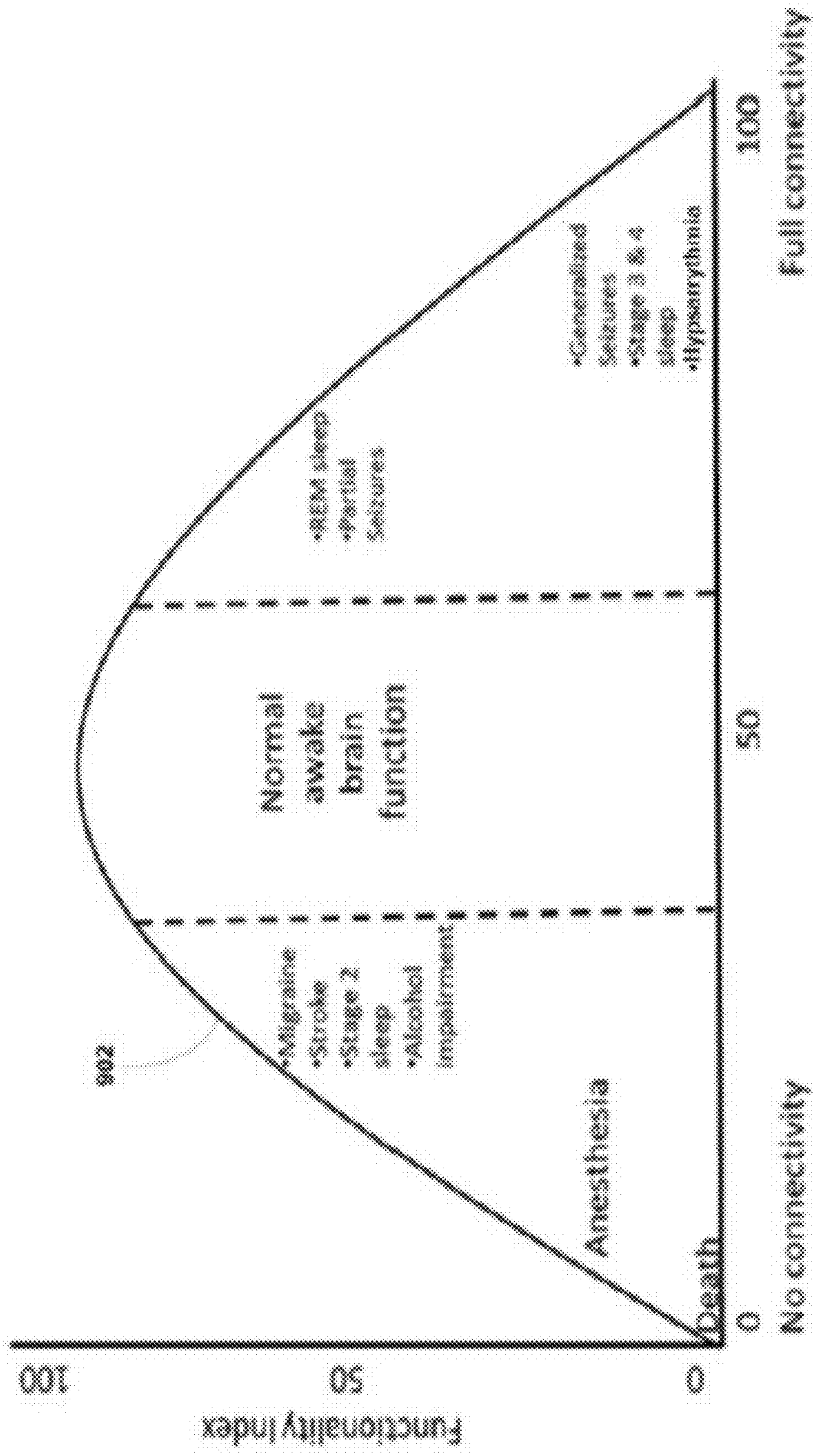
FIG. 42 is a graph with a visual representation for brain value index values for different brain states, including epileptic spasms and hypsarrhythmia (lower right hand corner with the generalized seizures and slow wave sleep) as described herein.

FIG. 42 is an example graph showing different normal and abnormal brain states and position on the brain value index curve, relative to the normal range represented between the vertical dashed lines. The hypsarrhythmia pattern, associated with epileptic spasms is found in the lower fight hand corner close to the 0 (zero) functionality index and near the 100 on the x-axis, representing maximum connectivity. It is similar to the abnormal condition of generalized seizures.

Figure 43:
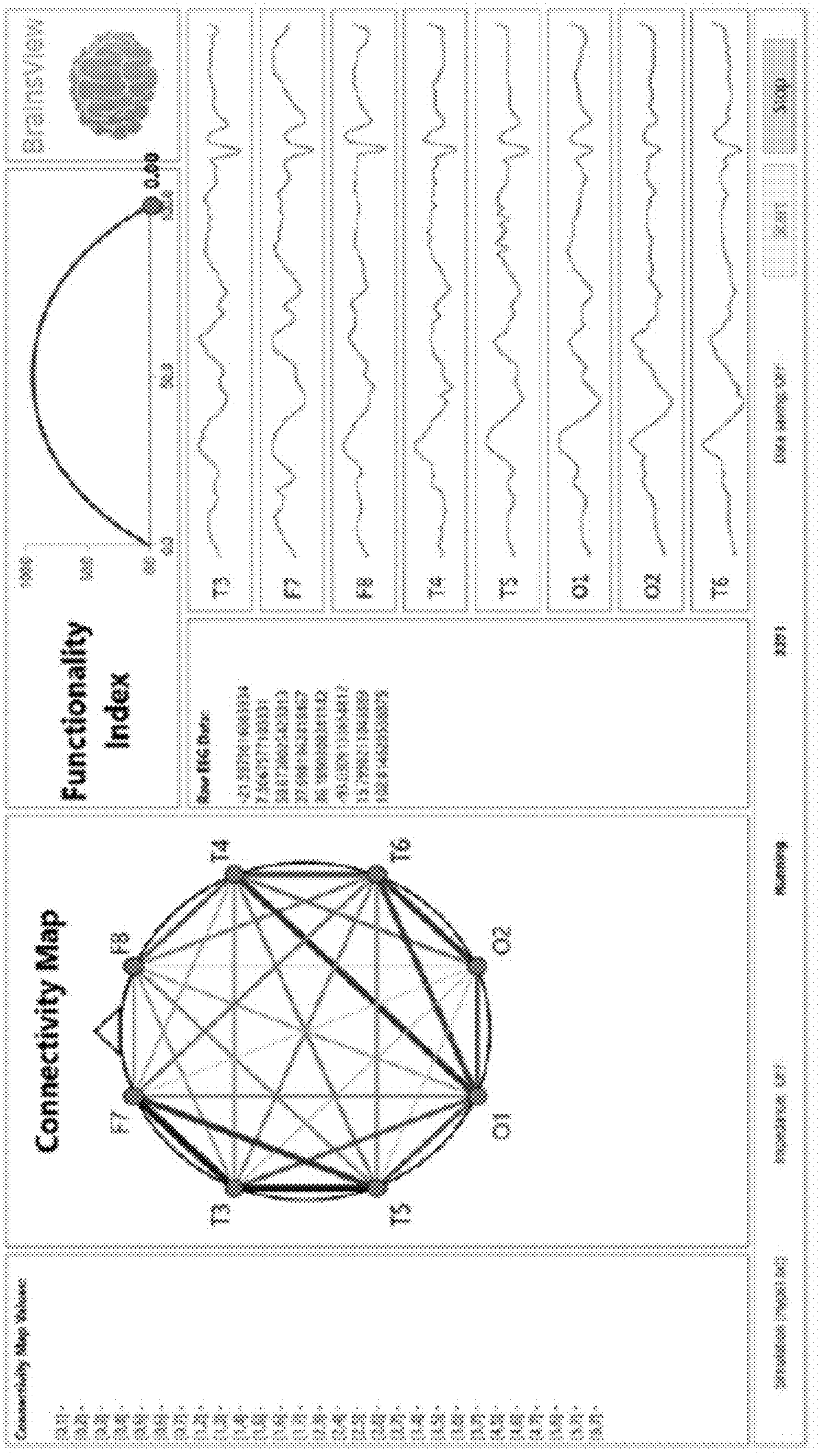
FIG. 43 shows an example interface with a visual representation of a connectivity map, connectivity map values, functionality index, and raw EEG data according to some embodiments.

FIG. 43 shows an interface with a graphical display of an example epileptic spasms and hypsarrhythmia disorder. In this case it represents the hypsarrhythmia pattern. The interface depicts 10 seconds of EEG recording an infant, which is representative of the hypsarrhythmia pattern. The EEG wave forms (bottom right hand corner) represent the characteristic high amplitude slow waves. The BVI or Functionality Index (top right hand corner) is "0" (zero) on the right side of the curve for this example. A Connectivity Map (left hand side panel) shows interhemispheric (between the hemispheres) connectivity to different degrees, between all pairs of electrodes. For example, for T4 and 01, phase synchrony index>0.9; F7 and 02, phase synchrony index 0.47 to 0.6. It also show intrahemispheric connectivity (within the same hemisphere. For example, F8 and 02, with a phase synchrony index 0.47 to 0.6. If the generalized connectivity and the functionality or brain value index of zero is prolonged (e.g. >10 seconds) it would trigger the resuscitation alarm.

Figure 44:
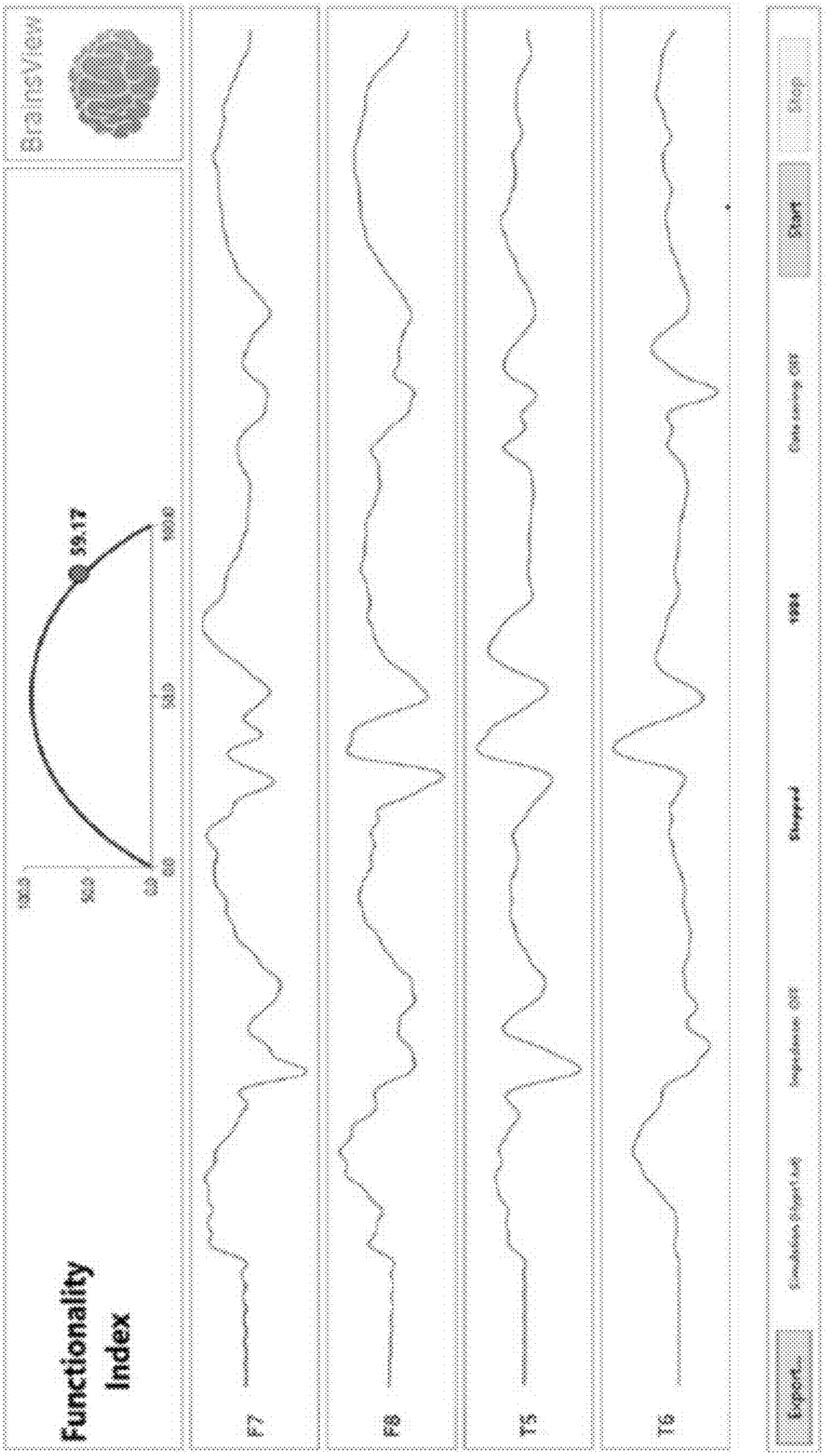
FIG. 44 shows an example interface with a visual representation of only 4 EEG channels and the functionality index (59.17) for a patient with epileptic spasms and characteristic hypsarrhythmia pattern.

FIG. 44 shows an alternate interface for brain monitoring in epileptic spasms. It represents only 4 EEG channels on the bottom portion of the display. In this example it represents channels F7, F8, T5 and T6, corresponding to left frontal, right frontal, left posterior temporal and right posterior temporal, respectively. The high amplitude, slow waves in the EEG channels are typical of the hypsarrhythmia pattern. The top portion displays the Functionality Index or Brain Value Index curve. In this example the associated value 59.17 or 59 and is on the right side of the curve, indicating low functionality and high connectivity.

Figure 45:
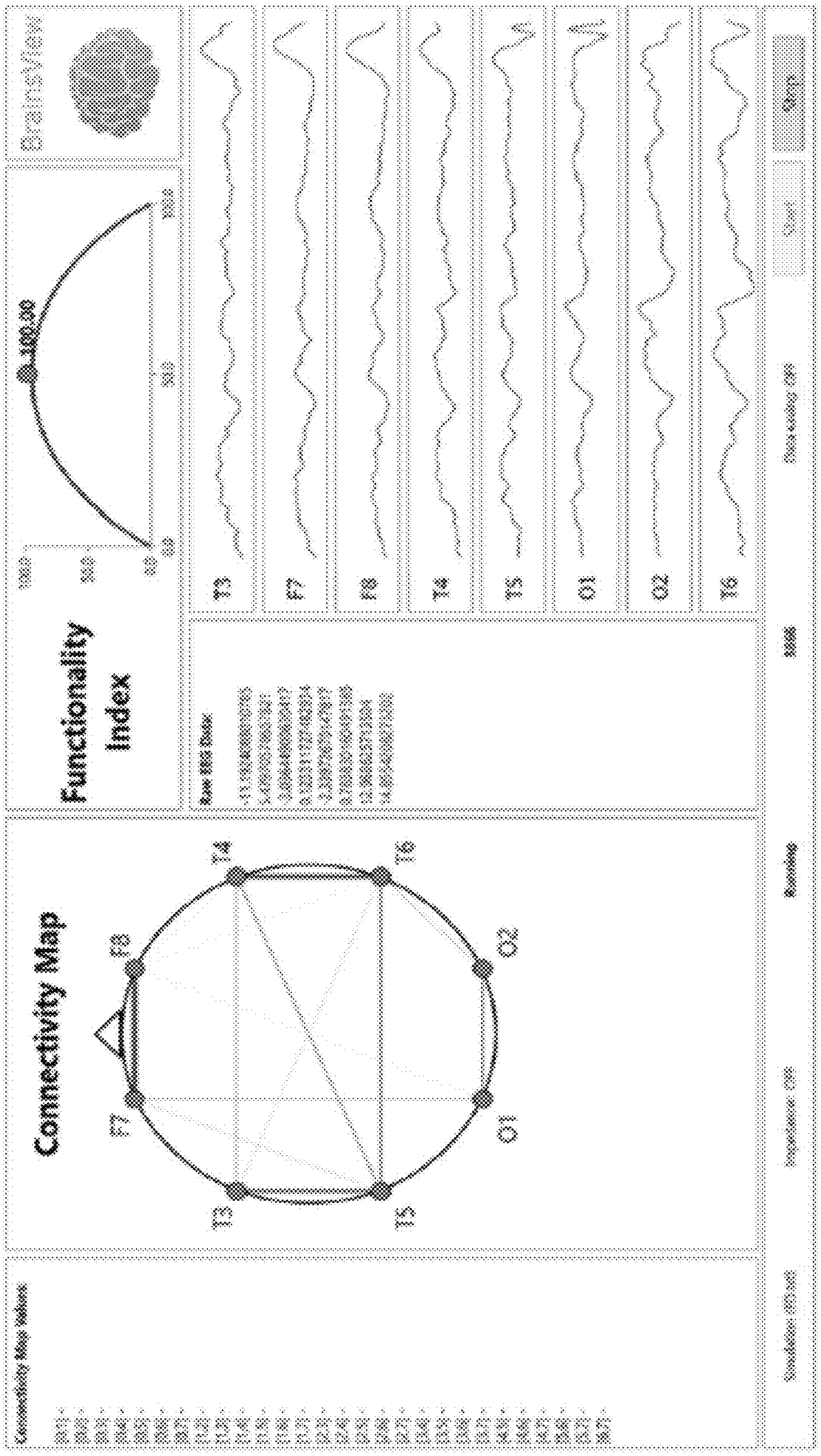
FIG. 45 shows an example interface with a visual representation of a connectivity map, connectivity map values, functionality index, and raw EEG data for the electrodecremental event (EDE) associated with the clinical manifestation of the spasm.
Figure 46:
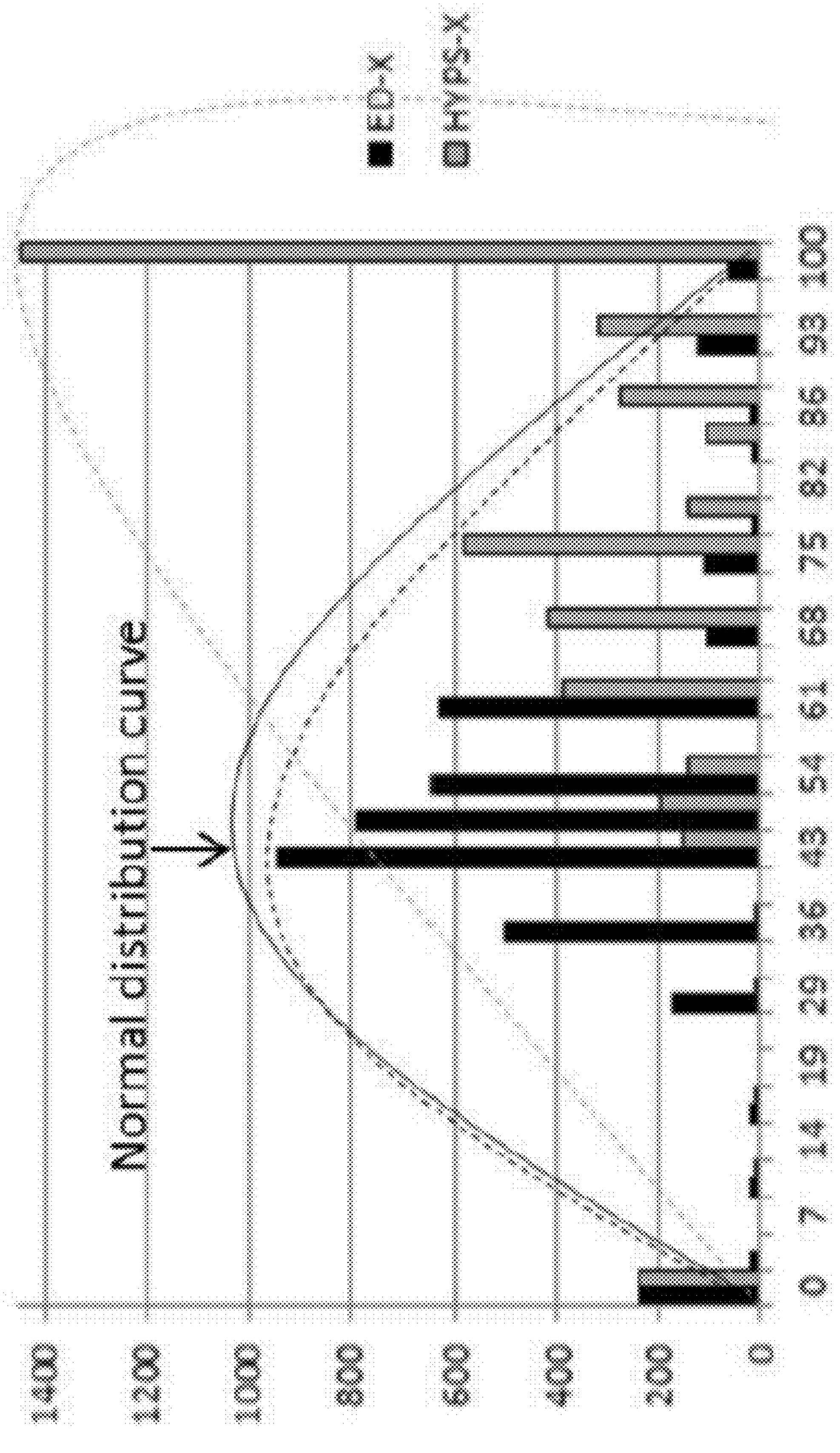
FIG. 46 shows an example graph of a 3-way comparison of the x axis component of the functionality index (degree of connectivity) for the: hypsarrhythmia pattern and the electrodecremental event in the same patient and the normal distribution of control subject values.

FIG. 45 shows the standard 8 EEG channel interface with connectivity map and values (left hand panel), raw EEG waveforms (bottom panel) and functionality index curve with corresponding value (top right hand panel). In this example the signal attenuation associated with the electrodecremental event is displayed in the 8 EEG channels. Clinically, this EEG pattern is associated with the physical spasm observed in the infant. The functionality or brain value index shows a maximum value of 100. FIG. 46 shows a graph of a 3-way comparison of the x axis component of the functionality index (degree of connectivity) for the: hypsarrhythmia pattern-Hyps (gray bars) and the electrodecremental event-ED (black bars) in the same patient and the normal distribution of control subject values (highlighted with arrow and text "normal distribution curve"). The ED bar distribution approaches the normal distribution curve with its maximum value at 43, where 50 is the middle of the connectivity axis. In contrast, the Hyps bar distribution is completely skewed to the right side of the curve.

Figure 47:
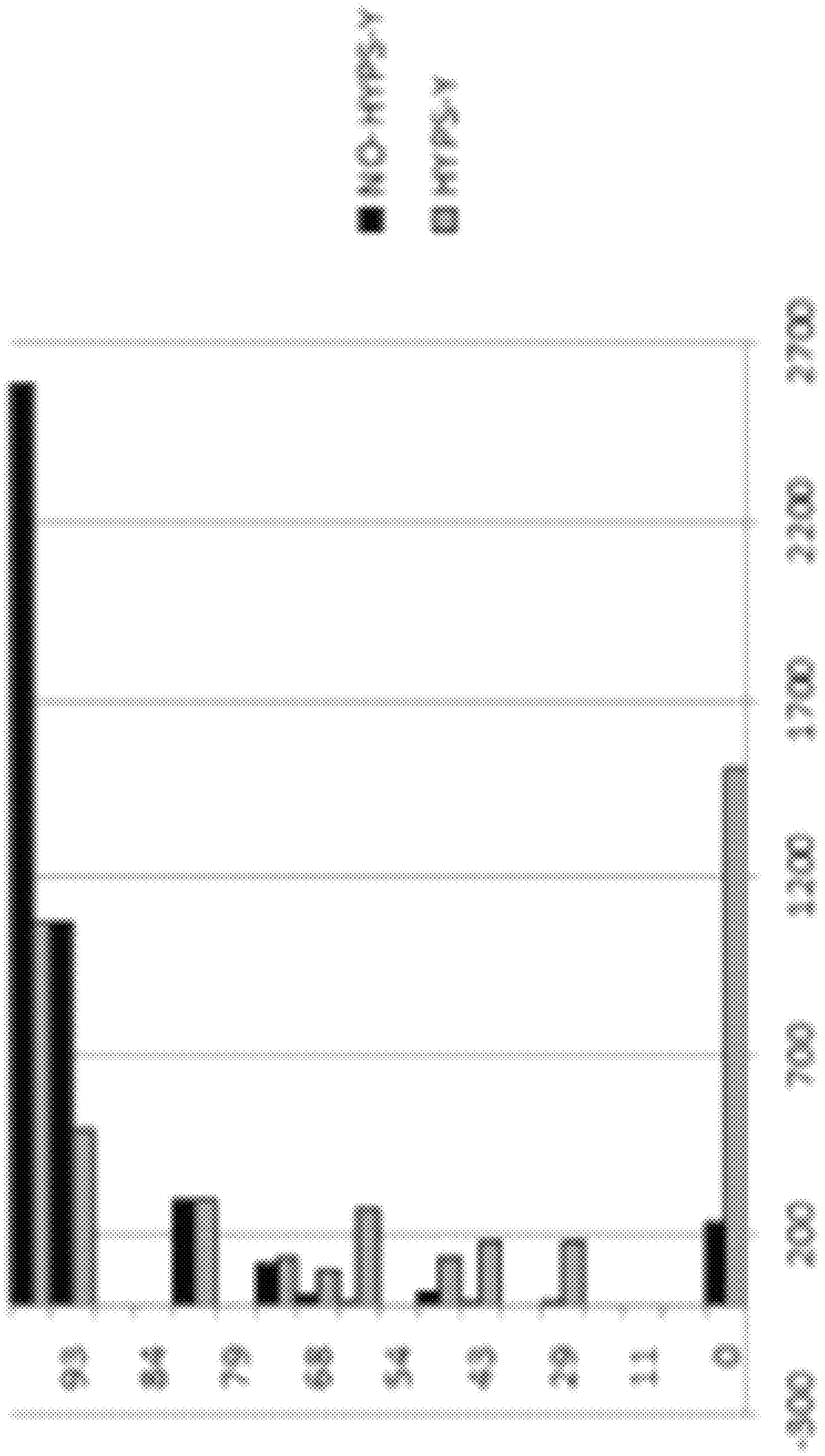
FIG. 47 shows an example graph comparing the y axis component of the functionality index of hypsarrhythmia EEG pattern and a normal infant EEG recording.

FIG. 47 shows an example graph comparing the y axis component of the functionality index of hypsarrhythmia EEG pattern and a normal infant EEG recording. The normal infant's bar distribution (black bars) shows that the maximum frequency is for the functionality or brain value index of 100. In contrast the patient with the hypsarrhythmia pattern's bar distribution (gray bars) shows that the maximum frequency is for the functionality or brain value index of 0.

Figure 48:
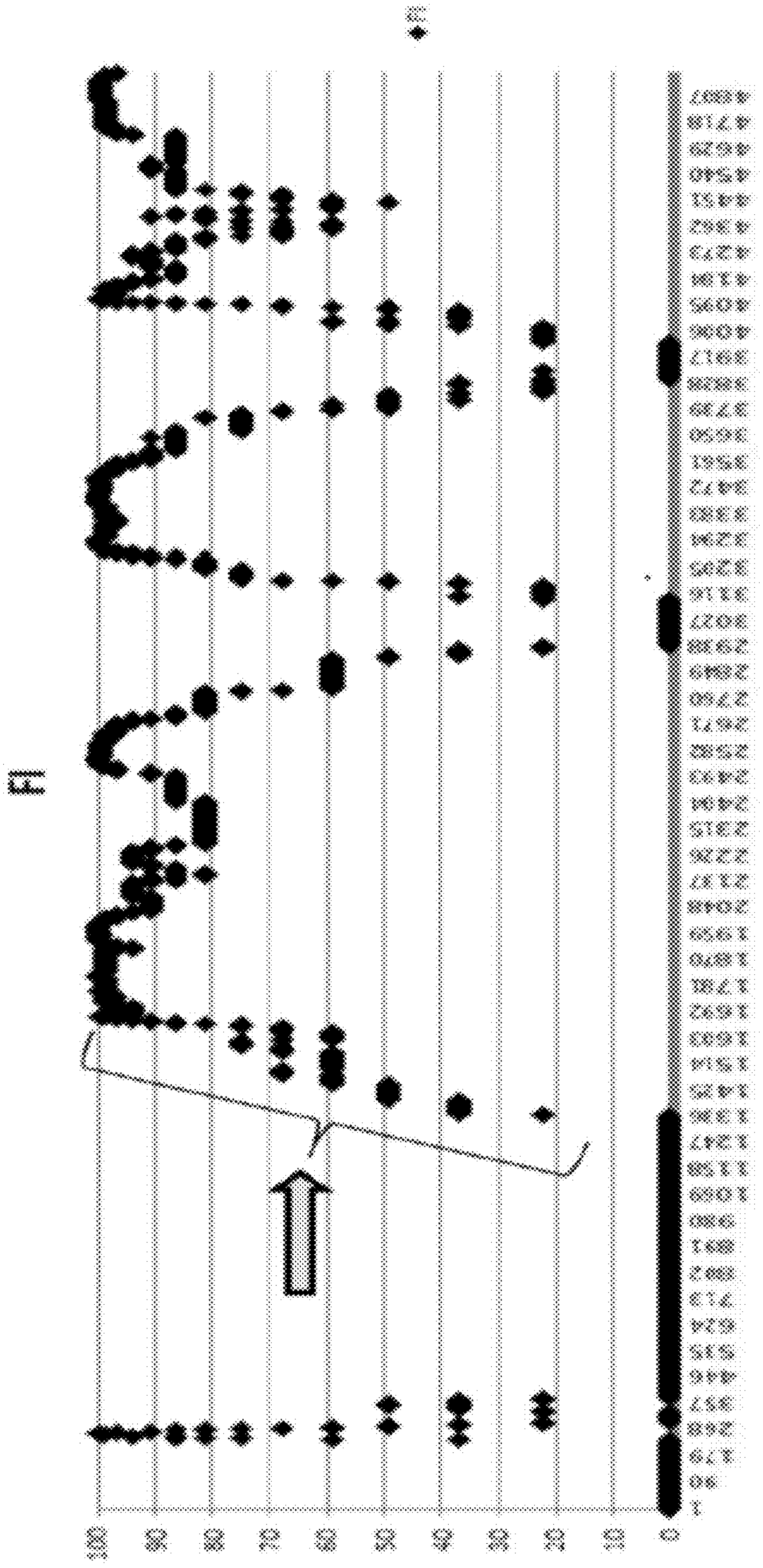
FIG. 48 shows an example graph for the time series of the functionality index during the electrodecremental event.
Figure 49:
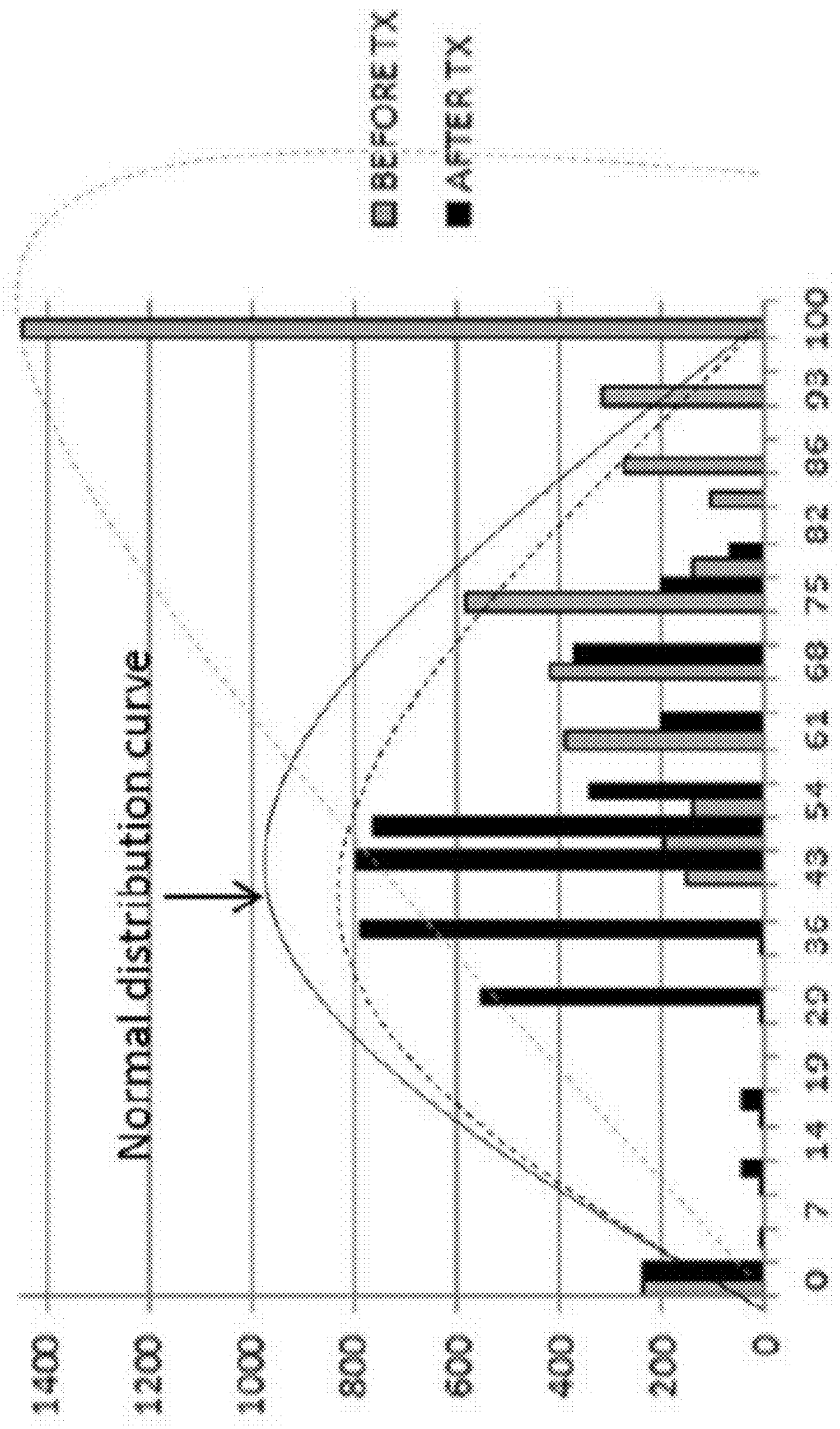
FIG. 49 shows an example graph comparing the x axis component of the functionality index (degree of connectivity) of the EEG patterns pre and post treatment with the drug vigabatrin.

FIG. 48 shows an example graph for the time series of the functionality index during the electrodecremental event. The values alternate between plateau at either the 0 or 100. Changes between these 2 main values are marked by steep inclines of increasing or decreasing values. FIG. 49 shows an example graph for the changes in the degree of connectivity (x axis component of the functionality or brain value index) when treatment is initiated. This graph shows a graph of a 3-way comparison of the degree of connectivity for the: same hypsarrhythmia pattern-Hyps (gray bars) as in FIG. 46 which is also the pre-treatment state and subsequent pattern (black bars) in the same patient after 2 weeks of treatment with vigabatrin. Again the normal distribution of control subject values (highlighted with arrow and text "normal distribution curve") is included. The pre-treatment Hyps bar distribution is completely skewed to the right side of the curve. In contrast, the post-treatment bar distribution again approaches the normal distribution curve with a cluster of maximum values between 36 and 43 on the x-axis.

These are examples to illustrate different use cases and functionality of the systems and processes described herein.

The embodiments of the devices, systems and methods described herein may be implemented in a combination of both hardware and software. These embodiments may be implemented on programmable computers, each computer including at least one processor, a data storage system (including volatile memory and non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

For simplicity only one server system 100 is shown but system may include more server systems 100 operable to access remote network resources and exchange data. The server system 100 has at least one processor, a data storage device (including volatile memory or non-volatile memory or other data storage elements or a combination thereof), and at least one communication interface. The server system 100 components may be connected in various ways including directly coupled, indirectly coupled via a network, and distributed over a wide geographic area and connected via a network (which may be referred to as "cloud computing").

For example, and without limitation, the server system 100 may be a server, network appliance, set-top box, embedded device, computer expansion module, computer or other computing device capable of being configured to carry out the processes described herein.

The server system 100, exemplary of an embodiment, may include at least one processor, memory, at least one I/O interface, and at least one network interface.

Each processor may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Memory may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface enables server system 100 to interconnect with one or more input devices, such as a keyboard, mouse, camera, touch screen and a microphone, or with one or more output devices such as a display screen and a speaker.

Each network interface enables server system 100 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

Server system 100 is operable to register and authenticate users (using a login, unique identifier, and password for example) prior to providing access to applications, a local network, network resources, other networks and network security devices. Server system 100 may serve one user or multiple users.

Further detail regarding epileptic spasms are provided in the manuscript (to be published) entitled "Hypsarrhythmia in epileptic spasms: Synchrony in Chaos" by the inventor, the entire contents of which is hereby incorporated by reference.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only.

Example Glossary of Terms

Functionality Index or Brain Value Index: Abbreviated as FI or BVI. Used interchangeably with "normalized entropy" and Functionality Index. It reflects the original term developed to represent normalized entropy both in value and its depiction on the right or left side of the curve in the graphical display. It was tested in market research with clinicians and changed to Functionality Index in current graphical output of the algorithms. Please see entropy definition.

Channel: Synonymous with electrode or sensor for gathering physiological information from a patient or control subject. Refers to either an EKG (heart rate) or EEG (brainwave).

Connectivity: Defined by the phase synchrony value, also known as the R index, and is an integer between 0 and 1. Please see phase synchronization definition.

Connectivity Map: Graphical depiction on a schematic of the 8 electrodes (channels), of the strength of the connectivity (phase synchronization) between each of the possible channel pairs. The threshold of a phase synchrony index=0.45, calculated from normal adult subjects in the awake state with eyes open. Four levels of connectivity strength are defined by the following ranges and illustrated with connecting lines of different colours and thicknesses. Light grey and 1 point thickness defines connectivity between a pair of electrodes with a phase synchrony value of 0.45 to <0.6; Medium grey and 1.5 point thickness for a phase synchrony value of 0.6 to <0.8; Dark grey and 2 point thickness for a phase synchrony value of 0.8 to <0.9; and black with a 3 point thickness for a phase synchrony value of 0.9 to 1.0<0.6.

Connectivity matrix: Step in the algorithm required for calculating entropy from the phase synchrony values for each electrode pair. Each electrode pair's phase synchrony is compared to the threshold (0.45) and assigned a "0" if it is below the threshold or "1" if it is above the threshold.

Electrode: Synonymous with channel or sensor for gathering physiological information from a patient or control subject. Refers to either an EKG (heart rate) or EEG (brainwave).

Entropy: In statistical thermodynamics, entropy is a measure of the number of microscopic configurations that a thermodynamic system can have when in a state as specified by certain macroscopic variables. In the case of brain function it is the number of connections between neuronal networks in a specific brain state, where the alert, awake state with eyes open represents the maximum connections and is the total information contained within functional neuronal networks.

Functionality Index. Used interchangeably with "normalized entropy". This term reflects market research with clinicians who preferred it over the normalized entropy. It is used in the current version graphical display of the device.

Montage: Refers to a specific arrangement of EEG electrodes on the scalp. Can be the international 10-20 montage of 10 to 20 electrodes or a subset of these.

Normalized entropy: The normalized entropy is the regular entropy that is calculated, divided by the maximum entropy (at the peak of the curve), and multiplied by 100. This gives the clinically useful 0 to 100 inverted U-shaped curve. It is synonymous with Functionality Index.

Phase synchrony (synchronization). Evaluates the connectivity between 2 oscillating signals, in our case, the EEG waveform output from 2 channels. It is an integer value between 0 and 1. It is calculated using the Hilbert as follows: where $\Delta\theta$ is the phase difference between two signals. It is dependent on the length of time specified for the calculation (1 second running window for our device) and the frequency of the signal (3 Hz for our device).

Sensor: Synonymous with channel or electrode for gathering physiological information from a patient or control subject. Refers to either an EKG (heart rate) or EEG (brainwave).

The invention claimed is:

1. A system for real-time brain monitoring for anxiety or epilepsy by processing real-time raw sensor data and continuously updating visual representations of a real-time brain state of a patient and corresponding treatment guidance, the system comprising:

at least one processor; and a memory comprising instructions which, when executed by the at least one processor, configure the at least one processor to:

receive sensor data obtained by a collector device coupled to a plurality of sensors for pre-processing real-time raw sensor data acquired from the plurality of sensors including a subset of sensors for monitoring a patient's brain, each sensor of the subset of sensors corresponding to a channel and a location relative to the patient's brain;

determine, using the sensor data, a connectivity matrix having connectivity values, a connectivity value for each pair of channels, and a real-time brain value index corresponding to a real-time brain state of the patient, the real-time brain state of the patient comprising a real-time anxiety state of the patient or a real-time epileptic spasm state of the patient, the brain value index determined based on a total number of possible pairs of channels given a specific channel montage N=Nc!/2!(Nc−p)!, Nc being a number of channels, p being a number of connected pairs of channels, p being calculated using a threshold value and the connectivity values of the connectivity matrix, wherein the processor implements machine learning to compute the brain value index based on historical data for the patient or other patients;

determine treatment data using the brain value index corresponding to the real-time brain state of the patient, wherein the treatment data provides one or more of a monitoring state to continue a current treatment for the patient, an intervention state to re-evaluate the patient and adjust the current treatment for the patient, and a resuscitate state to urgently intervene in the current treatment for the patient, wherein the treatment data is specific for a level of anxiety within a plurality of levels of anxiety, upon determining that the real-time brain state of the patient comprises the real-time anxiety state of the patient, wherein each of the plurality of levels of anxiety is associated with a threshold value or range of values configured for the patient, wherein the brain value index can be compared with the threshold value or range of values to determine the level of anxiety of the patient, wherein the treatment data is specific for an epileptic event of the patient within a plurality of epileptic events upon determining that the real-time brain state of the patient comprises the real-time epileptic spasm state of the patient, wherein each of the plurality of epileptic events is associated with a threshold value or range of values configured for the patient, wherein the brain value index can be compared with the threshold value or range of values to determine the epileptic event of the patient;

generate treatment guidance using the brain value index and the treatment data, wherein the processor implements machine learning to generate recommended treatments as part of the treatment guidance based on historical data for the patient or other patients, wherein the treatment guidance corresponds to the level of anxiety of the patient upon determining that the real-time brain state of the patient comprises the real-time anxiety state of the patient, wherein the treatment guidance corresponds to a number of epileptic spasms and hypsarrhythmia patterns of the patient upon determining that the real-time brain state of the patient comprises the real-time epileptic spasm state of the patient;

generate and update visual elements for an interface in real-time, the visual elements representing the real-time brain value index to depict the brain state of the patient, the treatment guidance with the recommended treatments, and a connectivity map for the connectivity matrix, the connectivity map visually indicating a head map for the patient with the arrangement of the channels of the subset of sensors and a connecting line between a pair of channels visually depicting a strength of connection between the pair of channels based on the respective connectivity value for the pair of channels, the at least one processor configured to issue control commands to continuously update the interface in real-time using the generated visual elements;

send signals to display the interface with the visual elements based on the issued control commands from the server to continuously update the interface in real-time with the visual elements; and automatically generate alerts based on the treatment data that provides one or more of the monitoring state, the intervention state and the resuscitate state, and transmit alert notifications in response to detecting specific real-time brain states.

2. The system of claim 1, wherein the brain value index corresponds to a functionality index within a range of numerical values, wherein upon determining that the real-time brain state of the patient comprises the real-time epileptic spasm state of the patient, the generated treatment guidance comprises:

valproic acid as medical treatment upon determining that the real-time epileptic spasm state of the patient is associated with the functionality index within a first range of the range of numerical values; and vigabatrin as medication treatment upon determining that the real-time epileptic spasm state of the patient is associated with the functionality index within a second range of the range of numerical values.

3. The system of claim 2, wherein real-time epileptic spasm state comprises one of:

a hypsarrhythmia state, or an electrodecremental state.

4. The system of claim 1, wherein the at least one processor is configured to:

determine, for each pair of channels, a phase synchronization value for an angle between the respective pair of channels using the sensor data for the respective pair of channels, wherein entries of the connectivity matrix are the phase synchronization values the pairs of channels;

generate a boolean connectivity matrix based on the connectivity matrix, such that an entry of the boolean connectivity matrix is 0 if a corresponding connectivity value is lower than a threshold value, and 1 if a corresponding connectivity value is higher than the threshold value, wherein the server determines the threshold value from sensor data for a normal adult with eyes open, wherein a connected channel is defined as an entry that is 1, wherein the server generates the brain value index using the boolean connectivity matrix;

receive feedback data to refine or update the determinations, the feedback data confirming the accuracy of the brain value index;

generate the interface to include visual elements depicting the channels, connections between the channels, and strengths of the connections; or generate the interface to include visual elements depicting a curve and a marker for the brain value index at a position along the curve at a point in time, the position indicating the brain state.

5. The system of claim 1, wherein at least one of:

the real-time raw sensor data is linked with a patient identifier and time indicia; or the interface comprises a graph of raw EEG signals per channel over time and a listing of the connectivity values.

6. A method of real-time brain monitoring for anxiety or epilepsy by processing real-time raw sensor data and continuously updating visual representations of a real-time brain state of a patient and corresponding treatment guidance, the method comprising:

receiving sensor data obtained by a collector device coupled to a plurality of sensors for pre-processing real-time raw sensor data acquired from the plurality of sensors including a subset of sensors for monitoring a patient's brain, each sensor of the subset of sensors corresponding to a channel and a location relative to the patient's brain;

determining, using the sensor data, a connectivity matrix having connectivity values, a connectivity value for each pair of channels, and a real-time brain value index corresponding to a real-time brain state of the patient, the real-time brain state of the patient comprising a real-time anxiety state of the patient or a real-time epileptic spasm state of the patient, the brain value index determined based on a total number of possible pairs of channels given a specific channel montage $N=Nc!/2!(Nc-p)!$, Nc being a number of channels, p being a number of connected pairs of channels, p being calculated using a threshold value and the connectivity values of the connectivity matrix, wherein the processor implements machine learning to compute the brain value index based on historical data for the patient or other patients;

determining treatment data using the brain value index corresponding to the real-time brain state of the patient, wherein the treatment data provides one or more of a monitoring state to continue a current treatment for the patient, an intervention state to re-evaluate the patient and adjust the current treatment for the patient, and a resuscitate state to urgently intervene in the current treatment for the patient, wherein the treatment data is specific for a level of anxiety within a plurality of levels of anxiety upon determining that the real-time brain state of the patient comprises the real-time anxiety state of the patient, wherein each of the plurality of levels of anxiety is associated with a threshold value or range of values configured for the patient, wherein the brain value index can be compared with the threshold value or range of values to determine the level of anxiety of the patient, wherein the treatment data is specific for an epileptic event of the patient of a plurality of epileptic events upon determining that the real-time brain state of the patient comprises the real-time epileptic spasm state of the patient, wherein each of the plurality of epileptic events is associated with a threshold value or range of values configured for the patient, wherein the brain value index can be compared with the threshold value or range of values to determine the epileptic event of the patient;

generating treatment guidance using the brain value index and the treatment data, wherein the processor implements machine learning to generate recommended treatments as part of the treatment guidance based on historical data for the patient or other patients, wherein the treatment guidance corresponds to the level of anxiety of the patient upon determining that the real-time brain state of the patient comprises the real-time anxiety state of the patient, wherein the treatment guidance corresponds to a number of epileptic spasms and hypsarrhythmia patterns of the patient upon determining that the real-time brain state of the patient comprises the real-time epileptic spasm state of the patient;

generating and updating visual elements for an interface in real-time, the visual elements representing the real-time brain value index to depict the brain state of the patient, the treatment guidance with the recommended treatments, and a connectivity map for the connectivity matrix, the connectivity map visually indicating a head map for the patient with the arrangement of the channels of the subset of sensors and a connecting line between a pair of channels visually depicting a strength of connection between the pair of channels based on the respective connectivity value for the pair of channels, the at least one processor configured to issue control commands to continuously update the interface in real-time using the generated visual elements;

sending signals to display the interface with the visual elements based on the issued control commands from the server to continuously update the interface in real-time with the visual elements; and automatically generating alerts based on the treatment data that provides one or more of the monitoring state, the intervention state and the resuscitate state, and transmitting alert notifications in response to detecting specific real-time brain states.

7. The method of claim 6, wherein the brain value index corresponds to a functionality index within a range of numerical values, wherein upon determining that the real-time brain state of the patient comprises the real-time epileptic spasm state of the patient, the generated treatment guidance comprises:

valproic acid as medical treatment upon determining that the real-time epileptic spasm state of the patient is associated with a functionality index within a first range of the range of numerical values; and vigabatrin as medication treatment upon determining that the real-time epileptic spasm state of the patient is associated with the functionality index within a second range of the range of numerical values.

8. The method of claim 6, wherein the real-time epileptic spasm state of the patient comprises one of:

a hypsarrhythmia state; or an electrodecremental state.

9. The method of claim 6, comprising at least one of:

determining, for each pair of channels, a phase synchronization value for an angle between the respective pair of channels using the sensor data for the respective pair of channels, wherein entries of the connectivity matrix are the phase synchronization values the pairs of channels;

generating a boolean connectivity matrix based on the connectivity matrix, such that an entry of the boolean connectivity matrix is 0 if a corresponding connectivity value is lower than a threshold value, and 1 if a corresponding connectivity value is higher than the threshold value, wherein the server determines the threshold value from sensor data for a normal adult with eyes open, wherein a connected channel is defined as an entry that is 1, wherein the server generates the brain value index using the boolean connectivity matrix;

receiving feedback data to refine or update the determinations, the feedback data confirming the accuracy of the brain value index;

generating the interface to include visual elements depicting the channels, connections between the channels, and strengths of the connections; or generating the interface to include visual elements depicting a curve and a marker for the brain value index at a position along the curve at a point in time, the position indicating the brain state.

10. The method of claim 6, wherein at least one of:

the real-time raw sensor data is linked with a patient identifier and time indicia; or the interface comprises a graph of raw EEG signals per channel over time and a listing of the connectivity values.

11. A system for real-time brain monitoring for anxiety or epilepsy by processing real-time raw sensor data and continuously updating visual representations of a real-time brain state of a patient and corresponding treatment guidance, the system comprising:

at least one processor; and a memory comprising instructions which, when executed by the at least one processor, configure the at least one processor to:

receive sensor data obtained by a collector device coupled to a plurality of sensors for pre-processing real-time raw sensor data acquired from the plurality of sensors including a subset of sensors for monitoring a patient's brain, each sensor of the subset of sensors corresponding to a channel and a location relative to the patient's brain;

determine a connectivity matrix having connectivity values, a connectivity value for each pair of channels, a real-time brain value index and treatment data using the sensor data, the real-time brain value index corresponding to a real-time brain state of the patient, the real-time brain state of the patient comprising a real-time anxiety state of the patient or a real-time epileptic spasm state of the patient, the brain value index determined based on a total number of possible pairs of channels given a specific channel montage $N=Nc!/2!(Nc-p)!$, Nc being a number of channels, p being a number of connected pairs of channels, p being calculated using a threshold value and the connectivity values of the connectivity matrix, wherein the processor implements machine learning to compute the brain value index based on historical data for the patient or other patients;

determine treatment data using the brain value index corresponding to the real-time brain state of the patient, wherein the treatment data provides one or more of a monitoring state to continue a current treatment for the patient, an intervention state to re-evaluate the patient and adjust the current treatment for the patient, and a resuscitate state to urgently intervene in the current treatment for the patient, wherein the treatment data is specific for a level of anxiety of a plurality of levels of anxiety upon determining that the real-time brain state of the patient comprises the real-time anxiety state of the patient, wherein each of the plurality of levels of anxiety is associated with a threshold value or range of values configured for the patient, wherein the brain value index can be compared with the threshold value or range of values to determine the level of anxiety of the patient, wherein the treatment data is specific for an epileptic event of the patient of a plurality of epileptic events upon determining that the real-time brain state of the patient comprises the real-time epileptic spasm state of the patient, wherein each of the plurality of epileptic events is associated with a threshold value or range of values configured for the patient, wherein the brain value index can be compared with the threshold value or range of values to determine the epileptic event of the patient;

generate treatment guidance using the brain value index and the treatment data, wherein the processor implements machine learning to generate recommended treatments as part of the treatment guidance based on historical data for the patient or other patients, wherein the treatment guidance corresponds to the level of anxiety of the patient upon determining that the real-time brain state of the patient comprises the real-time anxiety state of the patient, wherein the treatment guidance corresponds to a number of epileptic spasms and hypsarrhythmia patterns of the patient upon determining that the real-time brain state of the patient comprises the real-time epileptic spasm state of the patient;

generate and update visual elements for an interface in real-time, the visual elements representing a connectivity map for the connectivity matrix, the treatment guidance with the recommended treatments, the real-time brain value index and the treatment data, the visual elements depict the channels, connections between the channels, and strengths of the connections, the at least one processor configured to issue control commands to continuously update the interface in real-time;

send signals to display the interface the interface with the visual elements based on the issued control commands from the server to continuously update the interface in real-time with the visual elements; and automatically generate alerts based on the treatment data that provides one or more of the monitoring state, the intervention state and the resuscitate state, and transmit alert notifications in response to detecting specific real-time brain states.

12. The system of claim 11, wherein the brain value index corresponds to a functionality index within a range of numerical values, wherein upon determining that the real-time brain state of the patient comprises the real-time epileptic spasm state of the patient, the generated treatment guidance comprises:

valproic acid as medical treatment upon determining that the real-time epileptic spasm state of the patient is associated with a functionality index within a first range of the range of numerical values; and vigabatrin as medication treatment upon determining that the real-time epileptic spasm state of the patient is associated with the functionality index within a second range of the range of numerical values.

13. The system of claim 11, wherein real-time epileptic spasm state comprises one of:

a hypsarrhythmia state, or an electrodecremental state.

14. The system of claim 11, wherein the at least one processor is configured to at least one of:

receive feedback data to refine or update the determinations, the feedback data confirming the accuracy of the brain value index;

generate the connectivity map using the connectivity matrix, the connectivity map visually indicating a head map for the patient with the arrangement of the channels of the subset of sensors and a connecting line between a pair of channels visually depicting a strength of connection between the pair of channels based on the respective connectivity value for the pair of channels;

generate, for each pair of channels, a phase synchronization value for an angle between the respective pair of channels using the sensor data, wherein entries of the connectivity matrix are the phase synchronization values the pairs of channels;

generate a boolean connectivity matrix based on the connectivity matrix, such that an entry of the boolean connectivity matrix is 0 if a corresponding connectivity value is lower than a threshold value, and 1 if a corresponding connectivity value is higher than the threshold value, wherein the server determines the threshold value from sensor data for a normal adult with eyes open, wherein a connected channel is defined as an entry that is 1, wherein the server generates the brain value index using the boolean connectivity matrix; or generate the interface to include visual elements depicting a curve and a marker for the brain value index at a position along the curve at a point in time, the position indicating the brain state.

15. The system of claim 11, wherein at least one of:

the visual representation comprises a graph structure indicating connectivity between channels over time or at a point in time based on the connectivity matrix, wherein the graph structure indicating brain connectivity indicates a strength of brain connectivity between channel pairs; or the interface comprises a graph of raw EEG signals per channel over time and a listing of the connectivity values.

16. A method of real-time brain monitoring for anxiety or epilepsy by processing real-time raw sensor data and continuously updating visual representations of a real-time brain state of a patient and corresponding treatment guidance, the method comprising:

receiving sensor data obtained by a collector device coupled to a plurality of sensors for pre-processing real-time raw sensor data acquired from the plurality of sensors including a subset of sensors for monitoring a patient's brain, each sensor of the subset of sensors corresponding to a channel and a location relative to the patient's brain;

determining a connectivity matrix having connectivity values, a connectivity value for each pair of channels, a real-time brain value index and treatment data using the sensor data, the real-time brain value index corresponding to a real-time brain state of the patient, the real-time brain state of the patient comprising a real-time anxiety state of the patient or a real-time epileptic spasm state of the patient, the brain value index determined based on a total number of possible pairs of channels given a specific channel montage $N=Nc!/2!(Nc-p)!$, Nc being a number of channels, p being a number of connected pairs of channels, p being calculated using a threshold value and the connectivity values of the connectivity matrix, wherein the processor implements machine learning to compute the brain value index based on historical data for the patient or other patients;

determining treatment data using the brain value index corresponding to the real-time brain state of the patient, wherein the treatment data provides one or more of a monitoring state to continue a current treatment for the patient, an intervention state to re-evaluate the patient and adjust the current treatment for the patient, and a resuscitate state to urgently intervene in the current treatment for the patient, wherein the treatment data is specific for a level of anxiety of a plurality of levels of anxiety upon determining that the real-time brain state of the patient comprises the real-time anxiety state of the patient, wherein each of the plurality of levels of anxiety is associated with a threshold value or range of values configured for the patient, wherein the brain value index can be compared with the threshold value or range of values to determine the level of anxiety of the patient, wherein the treatment data is specific for an epileptic event of the patient of a plurality of epileptic events upon determining that the real-time brain state of the patient comprises the real-time epileptic spasm state of the patient, wherein each of the plurality of epileptic events is associated with a threshold value or range of values configured for the patient, wherein the brain value index can be compared with the threshold value or range of values to determine the epileptic event of the patient;

generating treatment guidance using the brain value index and the treatment data, wherein the processor implements machine learning to generate recommended treatments as part of the treatment guidance based on historical data for the patient or other patients, wherein the treatment guidance corresponds to the level of anxiety of the patient upon determining that the real-time brain state of the patient comprises the real-time anxiety state of the patient, wherein the treatment guidance corresponds to a number of epileptic spasms and hypsarrhythmia patterns of the patient upon determining that the real-time brain state of the patient comprises the real-time epileptic spasm state of the patient;

generating and updating visual elements for an interface in real-time, the visual elements representing a connectivity map for the connectivity matrix, the treatment guidance with the recommended treatments, the real-time brain value index and the treatment data, the visual elements depict the channels, connections between the channels, and strengths of the connections, the at least one processor configured to issue control commands to continuously update the interface in real-time;

sending signals to display the interface the interface with the visual elements based on the issued control commands from the server to continuously update the interface in real-time with the visual elements; and automatically generating alerts based on the treatment data that provides one or more of the monitoring state, the intervention state and the resuscitate state, and transmitting alert notifications in response to detecting specific real-time brain states.

17. The method of claim 16, wherein the brain value index corresponds to a functionality index within a range of numerical values, wherein upon determining that the real-time brain state of the patient comprises the real-time epileptic spasm state of the patient, the generated treatment guidance comprises:

valproic acid as medical treatment upon determining that the real-time epileptic spasm state of the patient is associated with a functionality index within a first range of the range of numerical values; and vigabatrin as medication treatment upon determining that the real-time epileptic spasm state of the patient is associated with the functionality index within a second range of the range of numerical values.

18. The method of claim 17, wherein real-time epileptic spasm state comprises one of:

a hypsarrhythmia state, or an electrodecremental state.

19. The method of claim 16, comprising at least one of:

receive feedback data to refine or update the determinations, the feedback data confirming the accuracy of the brain value index;

generate the connectivity map using the connectivity matrix, the connectivity map visually indicating a head map for the patient with the arrangement of the channels of the subset of sensors and a connecting line between a pair of channels visually depicting a strength of connection between the pair of channels based on the respective connectivity value for the pair of channels;

generate, for each pair of channels, a phase synchronization value for an angle between the respective pair of channels using the sensor data, wherein entries of the connectivity matrix are the phase synchronization values the pairs of channels;

generate a boolean connectivity matrix based on the connectivity matrix, such that an entry of the boolean connectivity matrix is 0 if a corresponding connectivity value is lower than a threshold value, and 1 if a corresponding connectivity value is higher than the threshold value, wherein the server determines the threshold value from sensor data for a normal adult with eyes open, wherein a connected channel is defined as an entry that is 1, wherein the server generates the brain value index using the boolean connectivity matrix; or generate the interface to include visual elements depicting a curve and a marker for the brain value index at a position along the curve at a point in time, the position indicating the brain state.

20. The method of claim 16, wherein at least one of:

the visual representation comprises a graph structure indicating connectivity between channels over time or at a point in time based on the connectivity matrix, wherein the graph structure indicating brain connectivity indicates a strength of brain connectivity between channel pairs; or the interface comprises a graph of raw EEG signals per channel over time and a listing of the connectivity values.

* * * * *